US005840554A

United States Patent [19]
Thompson et al.

[11] Patent Number: 5,840,554
[45] Date of Patent: Nov. 24, 1998

[54] β-ENDOTOXIN EXPRESSION IN *PSEUDOMONAS FLUORESCENS*

[75] Inventors: Mark Thompson, Del Mar; George E. Schwab, La Jolla, both of Calif.

[73] Assignee: Mycogen Corporation, San Diego, Calif.

[21] Appl. No.: 639,923

[22] Filed: Apr. 24, 1996

Related U.S. Application Data

[62] Division of Ser. No. 239,476, May 6, 1994, Pat. No. 5,527,883.

[51] Int. Cl.$^6$ .......................... C12N 15/11; C12N 15/32; C12N 15/78; A01N 63/00
[52] U.S. Cl. .............. 435/172.3; 435/69.7; 435/752.34; 435/32.01; 424/405; 424/538; 514/2; 530/350; 536/23.4; 536/23.71
[58] Field of Search .................... 435/69.7, 172.3, 435/252.34, 320.1; 536/23.4, 23.71, 350; 424/405, 538; 514/2

[56] References Cited

U.S. PATENT DOCUMENTS

| | | | |
|---|---|---|---|
| 4,448,885 | 5/1984 | Schnepf et al. | 435/252.3 |
| 4,467,036 | 8/1984 | Schnepf et al. | 435/320.1 |
| 4,797,276 | 1/1989 | Hernstadt et al. | 424/84 |
| 4,849,217 | 7/1989 | Soares et al. | 424/93.461 |
| 4,853,331 | 8/1989 | Hernstadt et al. | 435/252.3 |
| 4,918,006 | 4/1990 | Ellar et al. | 435/69.1 |
| 4,948,734 | 8/1990 | Edwards et al. | 514/2 |
| 5,055,294 | 10/1991 | Gilroy | 424/93.2 |
| 5,128,130 | 7/1992 | Gilroy et al. | 424/93.2 |
| 5,151,363 | 9/1992 | Payne | 435/252.31 |
| 5,208,077 | 5/1993 | Proctor et al. | 427/461 |
| 5,350,576 | 9/1994 | Payne et al. | 424/93.461 |
| 5,382,429 | 1/1995 | Donovan et al. | 424/93.461 |
| 5,436,002 | 7/1995 | Payne et al. | 424/93.461 |
| 5,441,884 | 8/1995 | Baum | 435/252.31 |
| 5,527,883 | 6/1996 | Thompson et al. | 530/350 |

FOREIGN PATENT DOCUMENTS

| | | |
|---|---|---|
| 0331470 | 9/1989 | European Pat. Off. . |
| 0410655 | 1/1991 | European Pat. Off. . |
| 0471564 | 2/1992 | European Pat. Off. . |

OTHER PUBLICATIONS

Chambers, J.A. et al. (1991) "Isolation and Characterization of a Novel Insecticidal Crystal Protein Gene from *Bacillus thuringiensis* subsp. aizawai" Journal of Bacteriology 173(13):3966–3976.

Nakamura, K. et al. (1990) "Construction of Chimeric Insecticidal Proteins between the 130–kDa and 135–kDa Proteins of *Bacillus thuringiensis* subsp. aizawai for Analysis of Structure—Function Relationship" Agricultural and Biological Chemistry 54(3):715–724.

Gaertner, F.H., L. Kim (1988) "Current Applied Recombinant DNA Projects" TIBTECH 6:S4–S7.

Gaertner, F.H. (1989) Cellular delivery systems for insecticidal proteins: living and non–living microorganisms in Controlled Deliver of Crop–Protection Agents, pp. 245–255.

Couch, T.L. (1980) "Mosquito Pathogenicity of *Bacillus thuringiensis* var. israelensis" Developments in Industrial Microbiology 22:61–76.

(List continued on next page.)

Primary Examiner—Robert A. Wax
Assistant Examiner—William W. Moore
Attorney, Agent, or Firm—Saliwanchik, Lloyd & Saliwanchik

[57] ABSTRACT

*Bacillus thuringiensis* endotoxin expression in Pseudomonads can be improved by modifying the gene encoding the *Bacillus thuringiensis* endotoxin. Chimeric genes are created by replacing the segment of the *Bacillus thuringiensis* gene encoding a native protoxin with a segment encoding a different protoxin. Exemplified herein is the cryIF/cryI(b) chimera wherein the native cryIF protoxin segment has been substituted by the cryIA(b) protoxin segment, to yield improved expression of the cryIF toxin in Pseudomonads. The invention also concerns novel genes and plasmids.

21 Claims, 10 Drawing Sheets

OTHER PUBLICATIONS

Beegle, C.C. (1978) "Use of Entomogenous Bacteria in AGroecosystems" in Developments in Industrial Microbiology 20:97–104.

Krieg, A. et al. (1983) "*Bacillus thuringiensis* var. tenebrionis: ein neuer, gegenuber Larven von Coleopteren Wirksamer Pathotyp" Z. ang. Ent. 96:500–508.

Hofte, H., H.R. Whieley (1989) "Insecticidal Crystal Proteins of *Bacillus thuringiensis*" Microbiological Reviews 52(2):242–255.

Feitelson, J.S. et al. (1992) "*Bacillus thuringiensis*: Insects and Beyond" Bio/Technology 10:271–275.

Schnepf, H.E., H.R. Whiteley (1981) "Cloning and expression of the *Bacillus Thuringiensis* crystal protein gene in *Escheerichia coli*" Proc. Natl. Acad. Sci. USA 78(5):2893–2897.

Li, J., J. Carroll, D.J. Ellar (1991) "Crystal structure of insecticidal δ–endotoxin from *Bacillus thuringiensis* at 2.5 A resolution" Nature 353:815–821.

Arvidson, H. et al. (1989) "Specificity of *Bacillus thuringiensis* for lepidopteran larvae: factors involved in vivo and in the structure of a purified protoxin" Molecular Microbiology 3(11):1533–1543.

Choma, C.T. et al. (1990) "Unusual proteolysis of the protoxin and toxin from *Bacillus thuringiensis*" Eur. J. Biochem. 189:523–527.

Haider, M.Z. et al. (1986) "Specificity of *Bacillus thuringiensis* var. colmeri insecticidal δ–endotoxin is determined by differential proteolytic processing of the protoxin" Eur. J. Biochem. 156:531–540.

Aronson, A.I. et al. (1991) "The Solubility of Inclusion Proteins from *Bacillus thuringiensis* Is Dependent upon Protoxin Composition and Is a Factor in Toxicity to Insects" Appl. Enrivon. Microbiol. 57(4):981–986.

Honee, G. et al. (1991) "The C–terminal domain of the toxic fragment of a *Bacillus thuringiensis* crystal protein determines receptor binding" Molecular Microbiology 5(11):2799–2806.

Honee, G. et al. (1990) "A Translation Fusion Product of Two Different Insecticidal Crystal Protein Genes of *Bacillus thuringiensis* Exhibits an Enlarged Insecticidal Spectrum" Appl. Environ. Microbiol. 56(3):823–825.

```
        1
Cons    MENNIQNQCV PYNCLNNPEV EILNEERSTG RLPLDISLSL TRFLLSEFVP GVGVAFGLFD LIWGFITPSD WSLFFLLQIEQ LIEQRIETLE    90
        91
Cons    RNRAITTLRG LADSYEIYIE ALREWEANPN NAQLREDVRI RFANTDDALI TAINNFTLTS FEIPLLSVYV QAANLHLSLL RDAVSFGQGW   180
        181
Cons    GLDIATVNNH YNRLINLIHR YTKHCLDTYN QGLENLRGTN TRQWARFNQF RRDLTLTVLD IVALFPNYDV RTYPIQTSSQ LTREIYTSSV   270
        271
Cons    IEDSPVSANI PNGFNRAEFG VRPPHLMDFM NSLFVTAETV RSQTVWGGHL VSSRNTAGNR INFPSYGVFN PGGAIWIADE DPRPFYRTLS   360
        361
Cons    DPVFVRGGFG NPHYVLGLRG VAFQQTGTNH TRTFRNSGTI DSLDEIPPQD NSGAPWNDYS HVLNHVTFVR WPGEISGSDS WRAPMFSWTH   450
        451
Cons    RSATPTNTID PERITQIPLV KAHTLQSGTT VVRGPGFTGG DILRRTSGGP FAYTIVNING QLPQRYRARI RYASTTNLRI YVTVAGERIF   540
        541                                                                       t
Alt                                              e                             i
Alt                                              r                             p       l   i
Cons    AGQFNKTMDT GDPLTFQSFS YATINTAFTF PMSQSSFTVG ADTFSSGNEV YIDRFELIPV TATFEAEYdL ERAQKAVNEL FTSSNQIGLK   630
        631                      e                    s             s kd    p          r
Alt           n       Q     t                                 ng
Alt     TDVTDYHIDr VSNLVECLSD EFCLDEKKEL SEKVKHAKRL SDERNLLQDP NFRGINRQLD RGWRGSTDIT IQGGDDVFKE NYVTLLGTFD   720
        721                 p       e                                         vq
Alt        l                                                            l       r
Cons    ECYPTYLYQK IDESKLKAYT RYQLRGYIED SQDLEIYLIR YNAKHETVNV PGTGSLWPLS APSPIG----    fe  s rKCGE PNRCAPHLEW NPDLDCSCRD   810
```

Fig. 9B

```
                                                                                                          900
                                                                  e   i   gra               ql
Alt                      d                                                                       
     811
Cons --KCAHHSHH FSLDIDVGCT DLNEDLGVWV IFKIKTQDGH ARLGNLEFLE EK-PLVGEAL ARVKRAEKKW RDKREKLEWE TNIVYKEAKE
                                                                                                          990
                          d
Alt               q          t      r q                vg  k              f
     901
Cons SVDALFVNSQ YDRLQADTNI AMIHAADKRV HSIREAYLPE LSVIPGVNAA IFEELEGRIF TAFSLYDARN VIKNGDFNNG LSCWNVKGHV
                                                                                                          1080
                                                         t                            n   g
Alt       q                                                                 f
     991
Cons DVEEQNNHRS VLVVPEWEAE VSQEVRVCPG RGYILRVTAY KEGYGEGCVT IHEIENNTDE LKFSNCVEEE VYPNNTVTCN DYTATQEEYE
                                                                                                          1170
Alt  a    c     et g  y                  v                              q
     1081
Cons GTYTSRNRGY DGAYESNSSV PADYASAYEE KAYTDGRRDN PCESNRGYGD YTPLPAGYVT KELEYFPETD KVWIEIGETE GTFIVDSVEL 1171
Cons LLMEE
```

β-ENDOTOXIN EXPRESSION IN PSEUDOMONAS FLUORESCENS

This is a division of application Ser. No. 08/239,476, filed May 6, 1994 and issued as U.S. Pat. No. 5,527,883.

BACKGROUND OF THE INVENTION

The soil microbe *Bacillus thuringiensis* (*B.t.*) is a Gram-positive, spore-forming bacterium characterized by parasporal crystalline protein inclusions. These inclusions often appear microscopically as distinctively shaped crystals. The proteins can be highly toxic to pests and specific in their toxic activity. Certain *B.t.* toxin genes have been isolated and sequenced, and recombinant DNA-based *B.t.* products have been produced and approved for use. In addition, with the use of genetic engineering techniques, new approaches for delivering these *B.t.* endotoxins to agricultural environments are under development, including the use of plants genetically engineered with endotoxin genes for insect resistance and the use of stabilized intact microbial cells as *B.t.* endotoxin delivery vehicles (Gaertner, F. H., L. Kim [1988] TIBTECH 6:S4–S7). Thus, isolated *B.t.* endotoxin genes are becoming commercially valuable.

Until the last ten years, commercial use of *B.t.* pesticides has been largely restricted to a narrow range of lepidopteran (caterpillar) pests. Preparations of the spores and crystals of *B. thuringiensis* subsp. kurstaki have been used for many years as commercial insecticides for lepidopteran pests. For example, *B. thuringiensis* var. kurstaki HD-1 produces a crystalline δ-endotoxin which is toxic to the larvae of a number of lepidopteran insects.

In recent years, however, investigators have discovered *B.t.* pesticides with specificities for a much broader range of pests. For example, other species of *B.t.*, namely israelensis and tenebrionis (a.k.a. *B.t.* M-7, a.k.a. *B.t.* san diego), have been used commercially to control insects of the orders Diptera and Coleoptera, respectively (Gaertner, F. H. [1989] "Cellular Delivery Systems for Insecticidal Proteins: Living and Non-Living Microorganisms," in *Controlled Delivery of Crop Protection Agents*, R. M. Wilkins, ed., Taylor and Francis, New York and London, 1990, pp. 245–255). See also Couch, T. L. (1980) "Mosquito Pathogenicity of *Bacillus thuringiensis* var. israelensis," *Developments in Industrial Microbiology* 22:61–76; Beegle, C. C., (1978) "Use of Entomogenous Bacteria in Agroecosystems," *Developments in Industrial Microbiology* 20:97–104. Krieg, A., A. M. Huger, G. A. Langenbruch, W. Schnetter (1983) Z. ang. Ent. 96:500–508, describe *Bacillus thuringiensis* var. tenebrionis, which is reportedly active against two beetles in the order Coleoptera. These are the Colorado potato beetle, *Leptinotarsa decemlineata*, and *Agelastica alni*.

Recently, new subspecies of *B.t.* have been identified, and genes responsible for encoding active δ-endotoxin proteins have been isolated (Höfte, H., H. R. Whiteley [1989] *Microbiological Reviews* 52(2):242–255). Höfte and Whiteley classified *B.t.* crystal protein genes into 4 major classes. The classes were CryI (Lepidoptera-specific), CryII (Lepidoptera- and Diptera-specific), CryIII (Coleoptera-specific), and CryIV (Diptera-specific). The discovery of strains specifically toxic to other pests has been reported. (Feitelson, J. S., J. Payne, L. Kim [1992] *Bio/Technology* 10:271–275).

The cloning and expression of a *B.t.* crystal protein gene in *Escherichia coli* has been described in the published literature (Schnepf, H. E., H. R. Whiteley [1981] *Proc. Natl. Acad. Sci. USA* 78:2893–2897). U.S. Pat. No. 4,448,885 and U.S. Pat. No. 4,467,036 both disclose the expression of *B.t.* crystal protein in *E. coli*. Hybrid *B.t.* crystal proteins have been constructed that exhibit increased toxicity and display an expanded host range to a target pest. See U.S. Pat. Nos. 5,128,130 and 5,055,294. U.S. Pat. Nos. 4,797,276 and 4,853,331 disclose *B. thuringiensis* strain tenebrionis (a.k.a. M-7, a.k.a. *B.t.* san diego) which can be used to control coleopteran pests in various environments. U.S. Pat. No. 4,918,006 discloses *B.t.* toxins having activity against dipterans. U.S. Pat. No. 4,849,217 discloses *B.t.* isolates which have activity against the alfalfa weevil. U.S. Pat. No. 5,208,077 discloses coleopteran-active *Bacillus thuringiensis* isolates. U.S. Pat. No. 5,151,363 and U.S. Pat. No. 4,948,734 disclose certain isolates of *B.t.* which have activity against nematodes. As a result of extensive research and investment of resources, other patents have issued for new *B.t.* isolates and new uses of *B.t.* isolates. However, the discovery of new *B.t.* isolates and new uses of known *B.t.* isolates remains an empirical, unpredictable art.

A majority of *Bacillus thuringiensis* δ-endotoxin crystal protein molecules are composed of two functional segments. The protease-resistant core toxin is the first segment and corresponds to about the first half of the protein molecule. The three-dimensional structure of a core segment of a cryIIIA *B.t.* δ-endotoxin is known and it is proposed that all related toxins have that same overall structure (Li, J., J. Carroll, D. J. Ellar [1991] *Nature* 353:815–821). The second half of the molecule is the second segment. For purposes of this application, this second segment will be referred to herein as the "protoxin segment." The protoxin segment is believed to participate in toxin crystal formation (Arvidson, H., P. E. Dunn, S. Strand, A. I. Aronson [1989] *Molecular Microbiology* 3:1533–1534; Choma, C. T., W. K. Surewicz, P. R. Carey, M. Pozsgay, T. Raynor, H. Kaplan [1990] *Eur. J. Biochem.* 189:523–527). The full 130 kDa toxin molecule is rapidly processed to the resistant core segment by protease in the insect gut. The protoxin segment may thus convey a partial insect specificity for the toxin by limiting the accessibility of the core to the insect by reducing the protease processing of the toxin molecule (Haider, M. Z., B. H. Knowles, D. J. Ellar [1986] *Eur. J. Biochem.* 156:531–540) or by reducing toxin solubility (Aronson, A. I., E. S. Han, W. McGaughey, D. Johnson [1991] *Appl. Environ. Microbiol.* 57:981–986).

Chimeric proteins joined within the toxin domains have been reported between CryIC and CryIA(b) (Honee, G., D. Convents, J. Van Rie, S. Jansens, M. Perferoen, B. Visser [1991] *Mol. Microbiol.* 5:2799–2806); however, the activity of these chimeric proteins was either much less, or undetectable, when compared to CryIC on a relevant insect.

Honee et al (Honee, G., W. Vriezen, B. Visser [1990] *Appl. Environ. Microbiol.* 56:823–825) also reported making a chimeric fusion protein by linking tandem toxin domains of CryIC and CryIA(b). The resulting protein had an increased spectrum of activity equivalent to the combined activities of the individual toxins; however, the activity of the chimeric was not increased toward any one of the target insects.

BRIEF SUMMARY OF THE INVENTION

The subject invention concerns the discovery that expression of *Bacillus thuringiensis* (*B.t.*) δ-endotoxin in Pseudomonas can be substantially improved by modifying the gene which encodes the *B.t.* toxin. Specifically, *B.t.* endotoxin expression in *P. fluorescens* can be improved by reconstructing the gene so as to replace the native protoxin-encoding segment with an alternate protoxin segment, yielding a chimeric gene.

In specific embodiments of the subject invention, chimeric genes can be assembled that substitute a heterologous protoxin segment for a native cryIF protoxin segment. In particular, all or part of the protoxin-encoding region of a cryIA(b) gene can be used in place of all or part of the region which encodes the protoxin for a native cryIF toxin. Similarly, a chimeric gene can be constructed wherein the region encoding all or part of the protoxin of a cryIF toxin is replaced by DNA encoding all or part of the protoxin of a cryIA(c)/cryIA(b) chimeric gene. In a specific embodiment, the cryIA(c)/cryIA(b) chimeric gene is that which has been denoted 436 and which is described in U.S. Pat. No. 5,128,130. This gene can be obtained from the plasmid in *P. fluorescens* MR436.

The subject invention also includes use of the chimeric gene encoding the claimed toxin. The chimeric gene can be introduced into a wide variety of microbial or plant hosts. A transformed host expressing the chimeric gene can be used to produce the lepidopteran-active toxin of the subject invention. Transformed hosts can be used to produce the insecticidal toxin or, in the case of a plant cell transformed to produce the toxin, the plant will become resistant to insect attack. The subject invention further pertains to the use of the chimeric toxin, or hosts containing the gene encoding the chimeric toxin, in methods for controlling lepidopteran pests.

Still further, the invention includes the treatment of substantially intact recombinant cells producing the chimeric toxin of the invention. The cells are treated to prolong the lepidopteran activity when the substantially intact cells are applied to the environment of a target pest. Such treatment can be by chemical or physical means, or a combination of chemical and physical means, so long as the chosen means do not deleteriously affect the properties of the pesticide, nor diminish the cell's capability of protecting the pesticide. The treated cell acts as a protective coating for the pesticidal toxin. The toxin becomes active upon ingestion by a target insect.

BRIEF DESCRIPTION OF THE DRAWINGS

Figure 3:
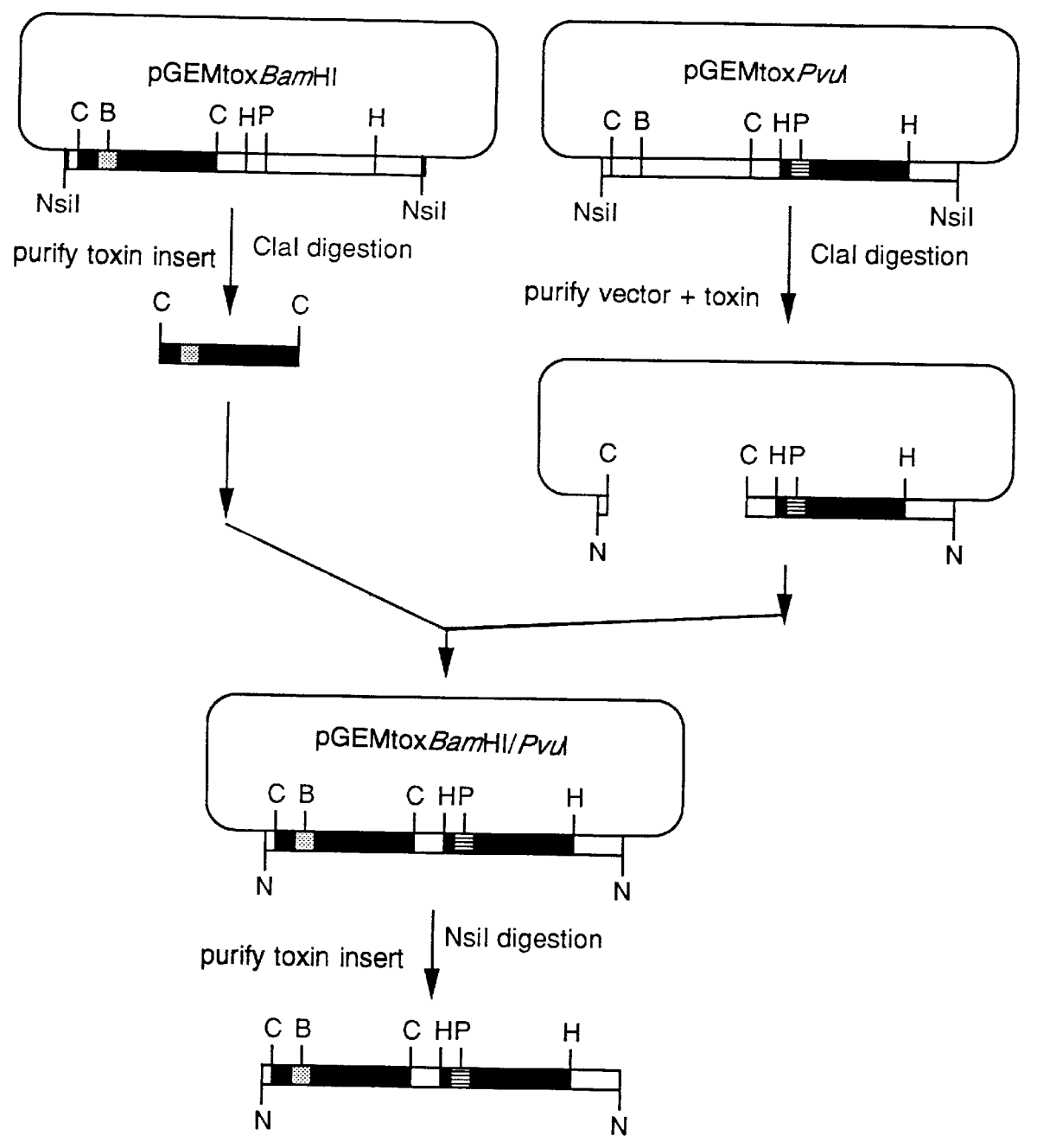

FIG. 3—The DNA fragment containing the BamHI mutation is used to replace the homologous fragment in pGEMtoxPvuI. The resulting plasmid which contains both cloning sites is pGEMtoxBamHI/PvuI. To construct an expression plasmid, the toxin-containing NsiI fragment is excised for cloning into the pTJS260 broad host-range vector. B=BamHI, C=ClaI, H=HindIII, P=PvuI.

FIG. 9—A CryIF/CryIA(b) chimeric protein sequence and residue-by-residue substitutions. The 'Cons' line shows a CryIF/CryIA(b) chimeric sequence. The 'Alt' lines show residue-by-residue substitutions found in the 436 protein, CryIA(b) variant proteins and CryIF protoxins.

BRIEF DESCRIPTION OF THE SEQUENCES

Figure 1:
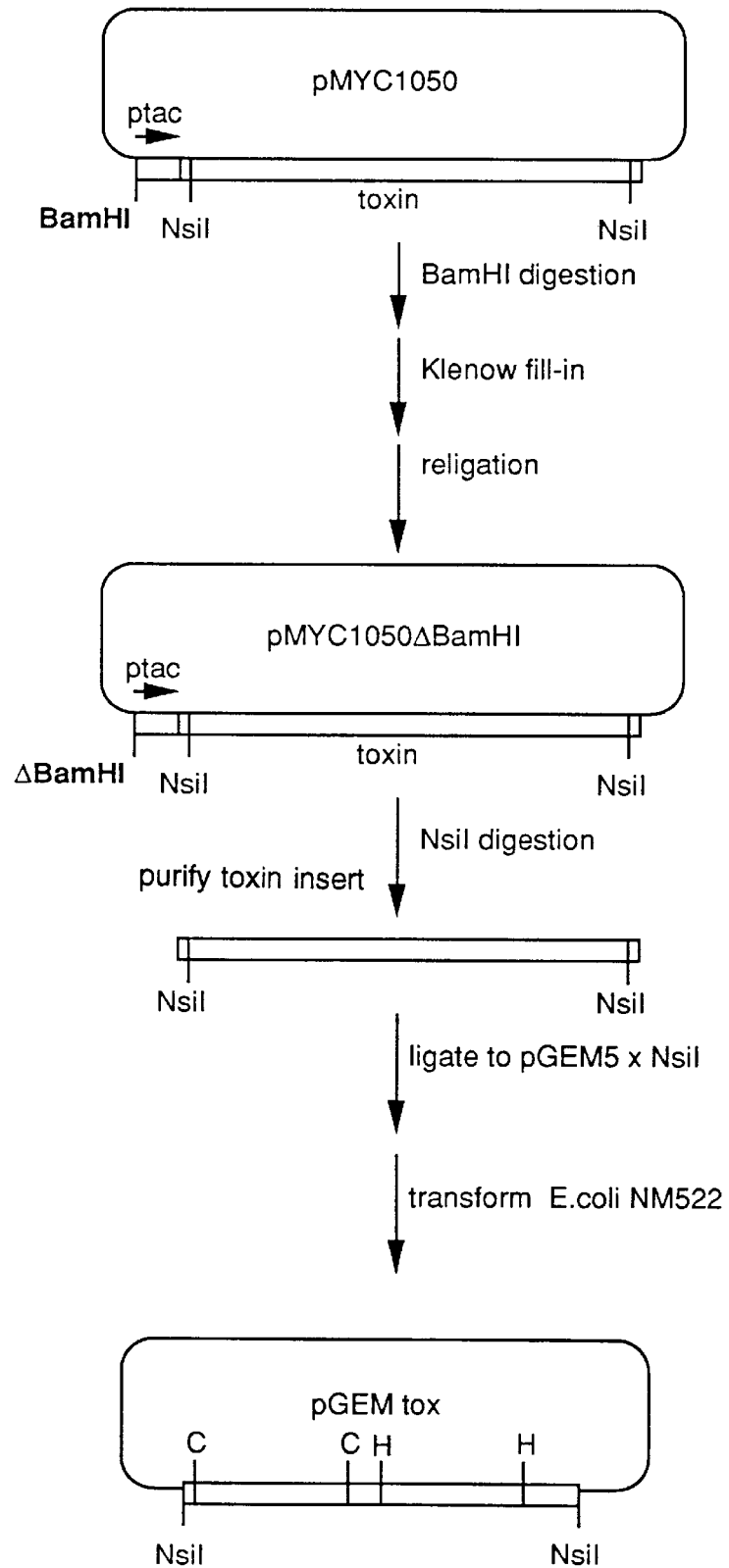
FIG. 1—The BamHI site is removed from pMYC1050 by a fill-in reaction with Klenow polymerase to give plasmid pMYC1050ΔBamHI. To facilitate cloning, an NsiI DNA fragment that contains most of the toxin open reading frame is cloned into pGEM5. The resulting plasmid is called pGEMtox. C=ClaI, H=HindIII.

SEQ ID NO. 1 is oligonucleotide primer "A"
SEQ ID NO. 2 is oligonucleotide primer "B"
SEQ ID NO. 3 is oligonucleotide primer "C"
SEQ ID NO. 4 is oligonucleotide primer "D"
SEQ ID NO. 5 is oligonucleotide primer "E"
SEQ ID NO. 6 is oligonucleotide primer "F"
SEQ ID NO. 7 is oligonucleotide primer "G"
SEQ ID NO. 8 is oligonucleotide primer "L"
SEQ ID NO. 9 is oligonucleotide primer "N"
SEQ ID NO. 10 is oligonucleotide primer "O"
SEQ ID NO. 11 is oligonucleotide primer "H"
SEQ ID NO. 12 is oligonucleotide primer "I"
SEQ ID NO. 13 is oligonucleotide primer "J"
SEQ ID NO. 14 is oligonucleotide primer "K"
SEQ ID NO. 15 is oligonucleotide primer "P"
SEQ ID NO. 16 is oligonucleotide primer "Q"
SEQ ID NO. 17 is oligonucleotide primer "M"
SEQ ID NO. 18 shows the toxin-encoding DNA sequence of pMYC2224.
SEQ ID NO. 19 shows the predicted amino acid sequence of the toxin encoded by pMYC2224.
SEQ ID NO. 20 shows the toxin-encoding DNA sequence of pMYC2239.
SEQ ID NO. 21 shows the predicted amino acid sequence of the toxin encoded by pMYC2239.
SEQ ID NO. 22 shows the toxin-encoding DNA sequence of pMYC2244, which encodes a cryIF/cryIA(b) chimeric toxin.
SEQ ID NO. 23 shows the predicted amino acid sequence of the cryIF/cryIA(b) chimeric toxin encoded by pMYC2244.
SEQ ID NO. 24 shows the toxin-encoding DNA sequence of pMYC2243.
SEQ ID NO. 25 shows the predicted amino acid sequence of the toxin encoded by pMYC2243.

SEQ ID NO. 26 shows the toxin-encoding DNA sequence of pMYC2523, which encodes a cryIF/cryIA(b) chimeric toxin with codon rework.

SEQ ID NO. 27 shows the predicted amino acid sequence of the toxin encoded by pMYC2523.

SEQ ID NO. 28 shows the toxin-encoding DNA sequence of pMYC2254, which encodes a cryIF/436 chimeric toxin.

SEQ ID NO. 29 shows the predicted amino acid sequence of the toxin encoded by pMYC2254.

SEQ ID NO. 30 is a characteristic sequence of cryI toxins. This sequence ends at residue 601 of SEQ ID NO. 30.

SEQ ID NO. 31 is the eight amino acids preceding amino acid 1043 in SEQ ID NO. 23.

SEQ ID NO. 32 shows the amino acid sequence of a native cryIF toxin.

SEQ ID NO. 33 shows the amino acid sequence of a native cryIa(b) toxin.

SEQ ID NO. 34 shows the amino acid sequence of a cryIA(c)/cryIA(b) toxin.

SEQ ID NO. 35 shows the amino acid sequence of a CryIF/CryIA(b) chimeric toxin of the subject invention that corresponds to the "Cons" sequence shown in FIG. 9.

SEQ ID NO. 36 shows the amino acid sequence of a chimeric toxin of the subject invention that incorporates the alternative amino acids as shown in the first "Alt" sequence listed above the "Cons" sequence shown in FIG. 9.

SEQ ID NO. 37 shows the amino acid sequence of a chimeric toxin of the subject invention that incorporates the alternative amino acids as shown in the second "Alt" sequence listed above the first "Alt" sequence shown in FIG. 9.

SEQ ID NO. 38 shows the amino acid sequence of a chimeric toxin of the subject invention that incorporates the alternative amino acids as shown in the third "Alt" sequence listed above the second "Alt" sequence shown in FIG. 9.

DETAILED DISCLOSURE OF THE INVENTION

The subject invention concerns the discovery that certain chimeric genes encoding *B.t.* toxins have improved expression in recombinant *Pseudomonas fluorescens*. The chimeric genes encode toxins wherein all or part of the native protoxin portion has been replaced with all or part of the protoxin from another *B.t.* toxin. Specifically exemplified herein are genes which encode a *B.t.* toxin which consists essentially of a cryIF core N-terminal toxin portion attached to a protoxin segment which is derived from either a cryIA(b) toxin or a cryIA(c)/cryIA(b) toxin as described herein. As used herein, reference to a "core" toxin portion refers to the portion of the full length *B.t.* toxin, other than the protoxin, which is responsible for the pesticidal activity of the toxin.

Bacteria harboring plasmids useful according to the subject invention are the following:

| Culture | Repository No. | U.S. Pat. No. |
| --- | --- | --- |
| *P. fluorescens* (pM3,130-7) | NRRL B-18332 | 5,055,294 |
| *P. fluorescens* MR436 (pM2,16-11, aka pMYC436) | NRRL B-18292 | 5,128,130 |
| *E. coli* NM522 (pMYC1603) | NRRL B-18517 | 5,188,960 |

It should be understood that the availability of a deposit does not constitute a license to practice the subject invention in derogation of patent rights granted by governmental action.

The flow charts of FIGS. 1–8 provide a general overview of vector construction that can be carried out according to the subject invention. BamHI and PvuI cloning sites can be introduced into a cryIA(c)/cryIA(b) chimeric toxin gene by mutagenesis using the PCR technique of Splice Overlap Extension (SOE) (Horton, R. M., H. D. Hunt, S. N. Ho, J. K. Pullen, L. R. Pease [1989] *Gene* 77:61–68) to give plasmid pMYC2224. A region of the cryIF gene from a cryIF-containing plasmid such as pMYC1260 can be generated by PCR and substituted for the BamHI-PvuI cryIA (c)/cryIA(b) gene fragment of pMYC2224. The new plasmid, which we designated pMYC2239, consisted of a short segment of cryIA(c) followed by cryIF to the toxin/protoxin segment junction. Thus, the protoxin segment was now derived from cryIA(b) (pMYC1050). An ApaI fragment derived from the cryIF clone (pMYC2047) was substituted for the ApaI fragment in pMYC2239. The resulting clone (pMYC2244) consisted of cryIF from the initiator methionine to the toxin/protoxin segment junction and cryIA(b) to the end of the coding region. Clone pMYC2243 was constructed by SOE to introduce silent codon changes in a limited region. The ApaI fragment from pMYC2243 that contained the silent changes was substituted for the ApaI fragment in pMYC2244 to give clone pMYC2523. The chimeric pMYC2523 showed an expression improvement over pMYC2243, which contains unchanged cryIF protein sequence.

A cryIF/436 chimera can be assembled by substituting the PvuI-BstEII protein segment-containing fragment of pMYC2523 with an equivalent fragment generated by PCR from a plasmid containing a cryIA(c)/cryIA(b) gene. One such gene is the 436 gene (e.g., pMYC467, as disclosed in U.S. Pat. Nos. 5,128,130 and 5,169,760). This construction also results in improved expression compared to the native cryIF protein sequence.

The chimeric toxins of the subject invention comprise a full core N-terminal toxin portion of a *B.t.* toxin and, at some point past the end of the toxin portion, the protein has a transition to a heterologous protoxin sequence. The transition to the heterologous protoxin segment can occur at approximately the toxin/protoxin junction or, in the alternative, a portion of the native protoxin (extending past the toxin portion) can be retained with the transition to the heterologous protoxin occurring downstream. As an example, one chimeric toxin of the subject invention has the full toxin portion of cryIF (amino acids 1–601) and a heterologous protoxin (amino acids 602 to the C-terminus). In a preferred embodiment, the heterologous portion of the protoxin is derived from a cryIA(b) or 436 toxin.

A person skilled in this art will appreciate that *B.t.* toxins, even within a certain class such as cryIF, will vary to some extent in length and the precise location of the transition from toxin portion to protoxin portion. Typically, the cryIA (b) and cryIF toxins are about 1150 to about 1200 amino acids in length. The transition from toxin portion to protoxin portion will typically occur at between about 50% to about 60% of the full length toxin. The chimeric toxin of the subject invention will include the full expanse of this core N-terminal toxin portion. Thus, the chimeric toxin will comprise at least about 50% of the full length cryIF *B.t.* toxin. This will typically be at least about 590 amino acids. With regard to the protoxin portion, the full expanse of the cryIA(b) protoxin portion extends from the end of the toxin portion to the C-terminus of the molecule. It is the last about 100 to 150 amino acids of this portion which are most critical to include in the chimeric toxin of the subject invention. In a chimeric toxin specifically exemplified herein, at least amino acids 1043 (of SEQ ID NO. 23) to the C-terminus of the cryIA(b) molecule are utilized. Amino acid 1043 in SEQ ID NO. 23 is preceded by the sequence Tyr Pro Asn Asn Thr Val Thr Cys (SEQ ID NO. 31). This amino acid sequence marks the location in the protoxin segment of the molecule beyond which heterologous amino acids will always occur in the chimeric toxin. In another example, the peptide shown as SEQ ID NO. 31 occurs at amino acids 1061 to 1068. In this case, amino acids 1069 to the C-terminus are preferably heterologous (SEQ ID NO. 29). The peptide shown in SEQ ID NO. 31 can be found at positions 1061 to 1068 in FIG. 9. Thus, it is at least the last approximately 5 to 10% of the overall B.t. protein which should comprise heterologous DNA (compared to the cryIF core N-terminal toxin portion) in the chimeric toxin of the subject invention. In the specific examples contained herein, heterologous protoxin sequences occur from amino acid 640 to the C-terminus.

Thus, a preferred embodiment of the subject invention is a chimeric B.t. toxin of about 1150 to about 1200 amino acids in length, wherein the chimeric toxin comprises a cryIF core N-terminal toxin portion of at least about 50 to 60% of a full cryIF molecule, but no more than about 90 to 95% of the full molecule. The chimeric toxin further comprises a cryIA(b) or a 436 protoxin C-terminal portion which comprises at least about 5 to 10% of the cryIA(b) or 436 molecule. The transition from cryIF to cryIA(b) or 436 sequence thus occurs within the protoxin segment (or at the junction of the toxin and protoxin segments) between about 50% and about 95% of the way through the molecule. In the specific examples provided herein, the transitions from the cryIF sequence to the heterologous protoxin sequences occur prior to the end of the peptide sequence shown in SEQ ID NO. 31.

A specific embodiment of the subject invention is the chimeric toxin shown in FIG. 9. Other constructs may be made and used by those skilled in this art having the benefit of the teachings provided herein. The core toxin segment of cryI proteins characteristically ends with the sequence: Val/Leu Tyr/Ile Ile Asp Arg/Lys Ile/Phe Glu Ile/Phe/Leu Ile/Leu/Val Pro/Leu Ala/Val Glu/Thr/Asp (SEQ ID NO. 30), which ends at residue 601 of SEQ ID NO. 23. Additionally, the protoxin segments of the cryI toxins (which follow residue 601) bear more sequence similarity than the toxin segments. Because of this sequence similarity, the transition point in the protoxin segment for making a chimeric protein between the cryIF sequence and the cryIA(b) or 436 sequence can be readily determined by one skilled in the art. From studies of data regarding the partial proteolysis of CryI genes, the heterogeneity and least-conserved amino acid regions are found after the conserved cryI protoxin sequence, positions 1061–1068 of FIG. 9.

Therefore a chimeric toxin of the subject invention can comprise the full cryIF toxin and a portion of the cryIF protoxin, transitioning to the corresponding cryIA(b) or 436 sequence at any position between the end of the toxin segment (as defined above) and the end of the peptide sequence shown in SEQ ID NO. 31. Preferably, the amino acid sequence of the C-terminus of the chimeric toxin comprises a cryIA(b) sequence or a sequence from the 436 gene or an equivalent of one of these sequences.

CryIF toxins, and genes which encode these toxins, are well known in the art. CryIF genes and toxins have been described in, for example, Chambers el al. (1991) *J. Bacteriol.* 173:3966. CryIA(b) genes and toxins have been described in, for example, Höfte et al. (1986) *Eur. J. Biochem.* 161:273; Geiser et al (1986) *Gene* 48:109; and Haider et al. (1988) *Nucleic Acids Res.* 16:10927. The skilled artisan having the benefit of the teachings contained herein could readily identify and use DNA which encodes the toxin N-terminal portion of a cryIF molecule and the C-terminal protoxin portion of the cryIA(b) toxins.

FIG. 9 provides examples of amino acid substitutions which can be used in the toxins of the subject invention. SEQ ID NO. 35 shows the amino acid sequence of a CryIF/CryIA(b) chimeric toxin of the subject invention that corresponds to the "Cons" sequence shown in FIG. 9. SEQ ID NO. 36 shows the amino acid sequence of a chimeric toxin of the subject invention that incorporates the alternative amino acids as shown in the first "Alt" sequence listed above the "Cons" sequence shown in FIG. 9. SEQ ID NO. 37 shows the amino acid sequence of a chimeric toxin of the subject invention that incorporates the alternative amino acids as shown in the second "Alt" sequence listed above the first "Alt" sequence shown in FIG. 9. SEQ ID NO. 38 shows the amino acid sequence of a chimeric toxin of the subject invention that incorporates the alternative amino acids as shown in the third "Alt" sequence listed above the second "Alt" sequence shown in FIG. 9. It is also well known in the art that various mutations can be made in a toxin sequence without changing the activity of a toxin. Furthermore, due to the degeneracy of the genetic code, a variety of DNA sequences can be used to encode a particular toxin. These alternative DNA and amino acid sequences can be used according to the subject invention by a person skilled in this art.

The protoxin substitution techniques of the subject invention can be used with other classes of B.t. endotoxins to enhance expression of the toxin. The technique would be most applicable to other B.t. toxins which have the characteristic sequence shown in SEQ ID NO. 30.

The subject invention not only includes the novel chimeric toxins and the genes encoding these toxins but also includes uses of these novel toxins and genes. For example, a gene of the subject invention may be used to transform host cells. These host cells expressing the gene and producing the chimeric toxin may be used in insecticidal compositions or, in the case of a transformed plant cell, in conferring insect resistance to the transformed cell itself.

Genes and toxins

The genes and toxins useful according to the subject invention include not only the full length sequences disclosed but also fragments of these sequences, variants, and mutants which retain the characteristic pesticidal activity of the toxins specifically exemplified herein. As used herein, the terms "variants" or "variations" of genes refer to nucleotide sequences which encode the same toxins or which encode equivalent toxins having pesticidal activity. As used herein, the term "equivalent toxins" refers to toxins having the same or essentially the same biological activity against the target pests as the claimed toxins.

It should be apparent to a person skilled in this art that genes encoding active toxins can be identified and obtained through several means. The specific genes (or portions thereof which encode toxin or protoxin domains) useful according to the subject invention may be obtained from the recombinant isolates deposited at a culture depository as described above. These genes, or portions or variants thereof, may also be constructed synthetically, for example, by use of a gene synthesizer. Variations of genes may be readily constructed using standard techniques for making point mutations. Also, fragments of these genes can be made using commercially available exonucleases or endonucleases according to standard procedures. For example, enzymes such as Bal31 can be used to systematically cut off nucleotides from the ends of these genes. Alternatively, site-directed mutagenesis can be used. Also, genes which encode active fragments may be obtained using a variety of restriction enzymes. Proteases may be used to directly obtain active fragments of these toxins.

Fragments and equivalents which retain the pesticidal activity of the exemplified toxins would be within the scope of the subject invention. Also, because of the redundancy of the genetic code, a variety of different DNA sequences can encode the amino acid sequence disclosed herein. It is well within the skill of a person trained in the art to create these alternative DNA sequences encoding the same, or essentially the same, toxin. These variant DNA sequences are within the scope of the subject invention. As used herein, reference to "essentially the same" sequence refers to sequences which have amino acid substitutions, deletions, additions, or insertions which do not materially affect pesticidal activity or expression level. Fragments retaining pesticidal activity are also included in this definition.

A further method for identifying the toxins and genes of the subject invention is through the use of oligonucleotide probes. These probes are detectable nucleotide sequences. These sequences may be detectable by virtue of an appropriate label or may be made inherently fluorescent as described in International Application No. WO93/16094. As is well known in the art, if the probe molecule and nucleic acid sample hybridize by forming a strong bond between the two molecules, it can be reasonably assumed that the probe and sample have substantial homology. Preferably, hybridization is conducted under stringent conditions by techniques well-known in the art, as described, for example, in Keller, G. H., M. M. Manak (1987) *DNA Probes*, Stockton Press, New York, N.Y., pp. 169–170. Detection of the probe provides a means for determining in a known manner whether hybridization has occurred. Such a probe analysis provides a rapid method for identifying toxin-encoding genes of the subject invention. Preferably, such genes would be cryIF genes whose core toxin-encoding portions can then be used with a cryIA(b) or 436 protoxin-encoding portion to create a chimeric gene according to the subject invention. The nucleotide segments which are used as probes according to the invention can be synthesized using DNA synthesizer and standard procedures. These nucleotide sequences can also be used as PCR primers to amplify genes of the subject invention.

Certain chimeric toxins of the subject invention have been specifically exemplified herein. It should be readily apparent that the subject invention comprises variant or equivalent toxins (and nucleotide sequences encoding equivalent toxins) having the same or similar pesticidal activity of the exemplified toxin. Equivalent toxins will have amino acid homology with the exemplified toxin. This amino acid homology will typically be greater than 75%, preferably be greater than 90%, and most preferably be greater than 95%. The amino acid homology will be highest in critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: nonpolar, uncharged polar, basic, and acidic. Conservative substitutions whereby an amino acid of one class is replaced with another amino acid of the same class fall within the scope of the subject invention so long as the substitution does not materially alter the biological activity of the compound. Table 1 provides a listing of examples of amino acids belonging to each class.

TABLE 1

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin.

Recombinant hosts

A gene encoding a chimeric toxin of the subject invention can be introduced into a wide variety of microbial or plant hosts. Expression of the toxin gene results, directly or indirectly, in the intracellular production and maintenance of the pesticidal chimeric toxin. With suitable microbial hosts, e.g., Pseudomonas, the microbes can be applied to the situs of the pest, where they will proliferate and be ingested. The result is control of the pest. Alternatively, the microbe hosting the toxin gene can be treated under conditions that prolong the activity of the toxin and stabilize the cell. The treated cell, which retains the toxic activity, then can be applied to the environment of the target pest.

Where the gene encoding the chimeric toxin is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Kiebsiella, Xanthomonas, Streptomyces, Rhizobium, Rhodopseudomonas, Methylophilius, Agrobactenium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syningae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus, and Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus,*

*S. odorus, Ktuyveromyces veronae*, and *Aureobasidium pollulans*. Of particular interest are the pigmented microorganisms.

A wide variety of ways are available for introducing a gene encoding a chimeric toxin into a microorganism host under conditions which allow for the stable maintenance and expression of the gene. These methods are well known to those skilled in the art and are described, for example, in U.S. Pat. No. 5,135,867, which is incorporated herein by reference.

Treatment of cells

As mentioned above, recombinant cells producing the chimeric toxin of the subject invention can be treated to prolong the toxic activity and stabilize the cell. The pesticide microcapsule that is formed comprises the *B.t.* toxin within a cellular structure that has been stabilized and will protect the toxin when the microcapsule is applied to the environment of the target pest. Suitable host cells may include either prokaryotes or eukaryotes, normally being limited to those cells which do not produce substances toxic to higher organisms, such as mammals. However, organisms which produce substances toxic to higher organisms could be used, where the toxic substances are unstable or the level of application sufficiently low as to avoid any possibility of toxicity to a mammalian host. As hosts, of particular interest will be the prokaryotes and the lower eukaryotes, such as fungi.

The cell will usually be intact and be substantially in the proliferative form when treated, rather than in a spore form, although in some instances spores may be employed.

Treatment of the microbial cell, e.g., a microbe containing the gene encoding a chimeric toxin of the subject invention, can be by chemical or physical means, or by a combination of chemical and/or physical means, so long as the technique does not deleteriously affect the properties of the toxin, nor diminish the cellular capability of protecting the toxin. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as glutaraldehyde; anti-infectives, such as zephiran chloride and cetylpyridinium chloride; alcohols, such as isopropyl and ethanol; various histologic fixatives, such as Lugol iodine, Bouin's fixative, various acids and Helly's fixative (See: Humason, Gretchen L., *Animal Tissue Techniques*, W. H. Freeman and Company, 1967); or a combination of physical (heat) and chemical agents that preserve and prolong the activity of the toxin produced in the cell when the cell is administered to the host environment. Examples of physical means are short wavelength radiation such as gamma-radiation and X-radiation, freezing, UV irradiation, lyophilization, and the like. Methods for treatment of microbial cells are disclosed in U.S. Pat. Nos. 4,695,455 and 4,695,462, which are incorporated herein by reference.

The cells generally will have enhanced structural stability which will enhance resistance to environmental conditions. Since the pesticide is in a proform, the method of cell treatment should be selected so as not to inhibit processing of the proform to the mature form of the pesticide by the target pest pathogen. For example, formaldehyde will crosslink proteins and could inhibit processing of the proform of a polypeptide pesticide. The method of treatment should retain at least a substantial portion of the bioavailability or bioactivity of the toxin.

Characteristics of particular interest in selecting a host cell for purposes of production include ease of introducing the gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; survival in aqueous environments; lack of mammalian toxicity; attractiveness to pests for ingestion; ease of killing and fixing without damage to the toxin; and the like. Other considerations include ease of formulation and handling, economics, storage stability, and the like.

Growth of cells

The cellular host containing the gene encoding a chimeric toxin of the subject invention may be grown in any convenient nutrient medium, where the DNA construct provides a selective advantage, providing for a selective medium so that substantially all or all of the cells retain the recombinant gene. These cells may then be harvested in accordance with conventional methods. Alternatively, the cells can be treated prior to harvesting.

Formulations

Recombinant microbes comprising a gene encoding a chimeric toxin disclosed herein, can be formulated into bait granules and applied to the soil. Formulated product can also be applied as a seed-coating or root treatment or total plant treatment at later stages of the crop cycle. Plant and soil treatments may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the pest, e.g., soil and foliage, by spraying, dusting, sprinkling, or the like.

MATERIALS AND METHODS

NACS (Bethesda Research Labs, Gaithersburg, Md.) column chromatography was used for purification of electroeluted DNA. It was performed according to the manufacturer's directions, except that the buffers were modified to 0.5× TBE/0.2M NaCl for binding, and 0.5× TBE/2.0M NaCl for elution.

Random priming labeling of DNA with α-[$^{32}$P]dATP was done with a kit (Boehringer-Mannheim Biochemicals, Indianapolis, Ind.) according to the manufacturer's directions.

Gel purification refers to sequential application of agarose-TBE gel electrophoresis, electroelution, and NACS column chromatography for purification of selected DNA fragments, methods which are well known in the art.

Polymerase chain reaction (PCR) amplification of DNA was done for 25 cycles on a Perkin Elmer (Norwalk, Conn.) thermal cycler with the following cycle parameters: 94° C. for 1 minute, 37° C. for 2 minutes, 72° C. for 3 minutes (each 72° C. has a 5 second extension time). PCR DNA products were proteinase K treated to improve cloning efficiency (Crowe, J. S., Cooper, H. J., Smith, M. A., Sims, M. J., Parker, D., Gewert, D. [1991] *Nucl. Acids Res.* 19:184).

Oligodeoxyribonucleotides (oligonucleotides) were synthesized on an Applied Biosystems (Foster City, Calif.) model 381A DNA synthesizer. Purification was done with Nensorb columns (New England Nuclear-Dupont, Wilmington, Del.), if necessary, according to the manufacturer's instructions.

Electroporation of *Pseudomonas fluorescens* was done with log-phase cells grown in L-broth (LB) at 30° C. on a rotary shaker. Cells were washed 2 to 3 times with ice-cold sterile distilled water and concentrated to 0.03× starting volume in distilled water. DNA in 1–20 µl was mixed with 50–300 µl of cells. Parameters selected for the Biorad Gene Pulser (Bio-Rad, Richmond, Calif.) were 200 ohms, 25 microfarads, and 2.25 kilovolts in a cuvette with a 0.2 cm electrode gap. Following electroporation, one milliliter of LB was added and cells were held on ice for at least 2 minutes. Cells were then incubated for 2 hours to overnight at 30° C. without shaking.

*B.t.* toxin expression in *P. fluorescens* was done in the recommended medium found in the *Manual of Methods for General Bacteriology* (P. Gerhardt et al, 1981, American Society for Microbiology, Washington, D.C.). Glycerol was substituted for glucose. The recipe was made with tap water and the pH adjusted to 7.2. Seed flasks were made from L-broth. The following recipes apply:

| Base Medium (for 1 liter) | |
|---|---|
| glycerol | 65 g |
| $(NH_4)_2SO_4$ | 1.0 g |
| $NA_2HPO_4$ | 5.24 g |
| $KH_2PO_4$ | 2.77 g |
| Yeast extract | 5.0 g |
| Casamino acids | 1.0 g |
| Metals 44 (for 100 ml) | |
| EDTA | 250 mg |
| $ZnSO_4.7H_2O$ | 1095 mg |
| $FeSO_4.7H_2O$ | 560 mg |
| $MnSO_4.H_2O$ | 154 mg |
| $CuSO_4.5H_2O$ | 39.2 mg |
| $Co(NO_3)_2.6H_2O$ | 24.8 mg |
| $Na_2B_4O_7.10H_2O$ | 17.7 mg |

| Huntner's Mineral Mix (for 1 liter) | |
|---|---|
| Nitriloacetic acid (dissolved and neutralized with KOH) | 10 g |
| $MgSO_4.7H_2O$ | 14.45 g |
| $CaCl_2.2H_2O$ | 3.33 g |
| $(NH_4)_6Mo_7O_{24}.4H_2O$ | 9.25 g |
| $FeSO_4.7H_2O$ | 99 mg |
| Metals 44 | 50 ml |
| pH adjusted to 6.6–6.8 | |

At inoculation for analysis of *B.t.* toxin expression, 4 ml of Huntner's Mineral Mix was added per 200 ml of broth. Flasks were then given a 2% inoculum, by volume, of an overnight culture. Cultures were allowed to grow for 24 hours at 32° C. at ≧200 rpm. At this point, they were induced with 0.75 mM IPTG and supplemented with 2 g yeast extract. Protein gels were run on samples pulled at 48 and 72 hours. The approximately 130 kDa protein was quantified by laser densitometry.

Following are examples which illustrate procedures, including the best mode, for practicing the invention. These examples should not be construed as limiting. All percentages are by weight and all solvent mixture proportions are by volume unless otherwise noted.

EXAMPLE 1

Expression Vector Modification by Splice Overlap Extension (SOE)

A cloning vector can be constructed based on pTJS260, a broad host-range plasmid derived from RSF1010 (pTJS260 can be obtained from Dr. Donald Helinski, U.C. San Diego). An example of the system used in the vector construction can be found in EPO patent application 0 471 564. A cryIA(c)/cryIA(b) gene, referred to herein as the 436 gene and toxin, are described in U.S. Pat. No. 5,055,294. A plasmid designated pMYC1050 contains a cryIA(c)/cryIA (b) chimeric gene known as the 420 gene. pMYC1050 was constructed by re-cloning the toxin gene and promoter of pM3,130-7 (disclosed in U.S. Pat. No. 5,055,294) into a pTJS260-based vector such as pMYC467 (disclosed in U.S. Pat. No. 5,169,760) by methods well known in the art. In particular, the pM3,130-7 promoter and toxin gene can be obtained as a BamHI to NdeI fragment and placed into the pMYC467 plasmid replacing a fragment bounded by the same sites (BamHI near base 12100 and NdeI near base 8000).

The improved vector ideally contains a unique BamHI cloning site. The plasmid BamHI site, located upstream from the tac promoter (Ptac), can be removed by blunting with Klenow and religating (FIG. 1). Absence of the site can be confirmed by restriction digestion. A plasmid produced according to this procedure was called pMYC1050ΔBamHI. The construct can now have a BamHI site added to the plasmid by SOE mutagenesis. SOE mutagenesis can be facilitated by subcloning an NsiI toxin-containing DNA fragment into the smaller pGEM5 (Promega Corp., Madison, Wis.) vector which uses the ampicillin resistance (bla) gene as a selectable marker (FIG. 1). The fragment can be oriented by restriction digestion. A plasmid produced according to this procedure was called pGEMtox.

Figure 2:
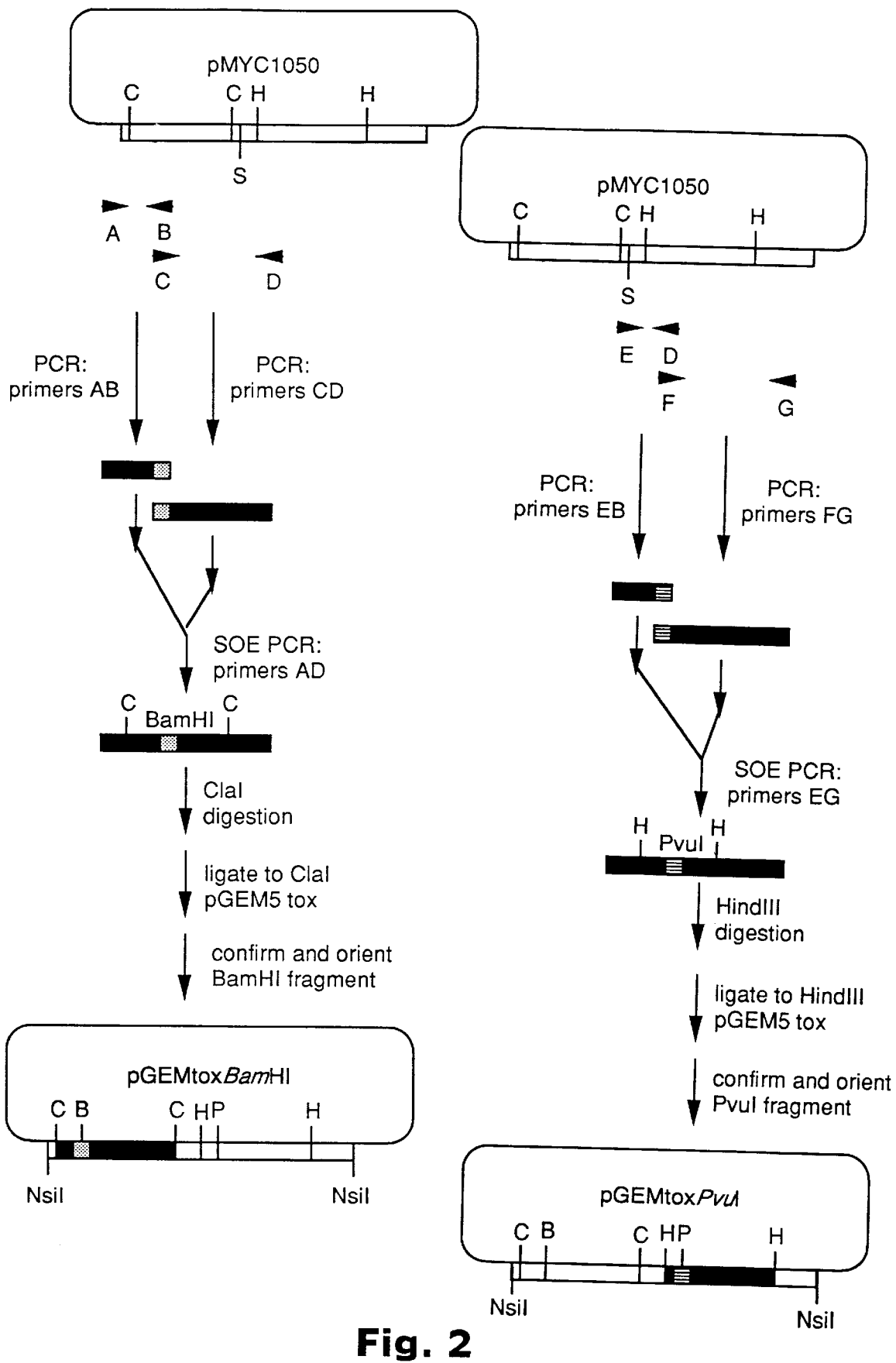
FIG. 2—BamHI or PvuI cloning sites were introduced into toxin DNA by the technique of Splice Overlap Extension (SOE). DNA fragments with the new sites are used to replace homologous DNA fragments in pGEMtox. The resulting plasmids are pGEMtoxBamHI or pGEMtoxPvuI. The letters A through G below the arrows correspond to oligonucleotide primers in the text. Letters above vertical lines correspond to restriction enzyme sites. B=BamHI, C=ClaI, H=HindIII, P=PvuI, S=SacI.
Figure 4:
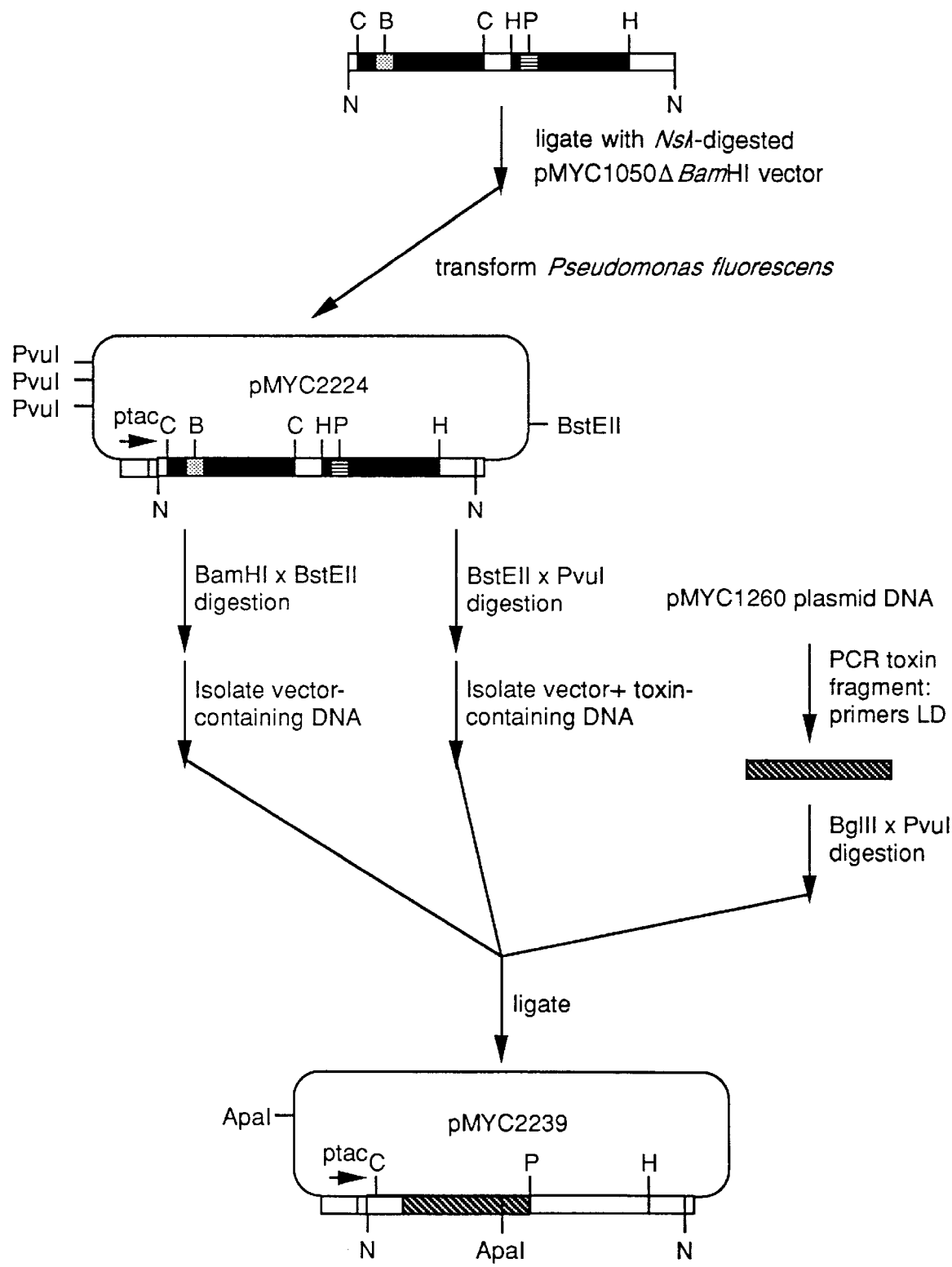
FIG. 4—The NsiI toxin-containing fragment with the new restriction sites is ligated to the vector-containing DNA from pMYC1050ΔBamHI to give pMYC2224. A BamHI-PvuI PCR-derived DNA fragment containing the cryIF toxin is exchanged for the equivalent fragment in pMYC2224. The resulting chimera is called pMYC2239. B=BamHI, C=ClaI, H=HindIII, N=NsiI, P=PvuI.

DNA in the toxin coding region can be mutated by the PCR-mediated technique of SOE to introduce restriction enzyme cloning sites as shown in FIG. 2. Oligonucleotides useful as primers are shown below:

"A" (SEQ ID NO. 1)

5' GCATACTAGTAGGAGATTTCCATGGATAACAATCCGAAC 3'

"B" (SEQ ID NO. 2)

5' GGATCCGCTTCCCAGTCT 3'

"C" (SEQ ID NO. 3)

5' AGAGAGTGGGAAGCGGATCCTACTAATCC 3'

"D" (SEQ ID NO. 4)

5' TGGATACTCGATCGATATGATAATCCGT 3'

"E" (SEQ ID NO. 5)

5' TAATAAGAGCTCCTATGT 3'

"F" (SEQ ID NO. 6)

5' TATCATATCGATCGAGTATCCAATTTAG 3'

"G" (SEQ ID NO. 7)

5' GTCACATAGCCAGCTGGT 3' pMYC1050 DNA was used as the template for PCR amplification using primer sets A/B, C/D, E/D, and F/G. Amplified DNA fragments were named AB, CD, ED, and FG. Amplified DNAs were purified by agarose-TBE gel electrophoresis, electroelution, and NACS column chromatography, methods all well-known in the art. Purified template DNAs were used in a second set of PCR reactions. Fragments AB and CD were mixed and amplified with primers A and D. In a separate reaction, fragments ED and FG were mixed and amplified with primers E and G. Amplified DNA was resolved by agarose-TBE gel electrophoresis and the fragments with the corresponding increase in size were excised, electroeluted, and purified over NACS columns by means well known in the art. Amplified DNA fragments are called AD or EG for reference.

DNA fragments AD or EG with the new restriction enzyme sites were incorporated into the toxin-containing DNA by several subcloning procedures (FIGS. 2 and 3). pGEMtox was digested with ClaI or HindIII. Vector-containing DNA was gel-purified. Fragment AD was digested with ClaI and ligated to ClaI-digested pGEMtox vector DNA. Fragment EG was digested with HindIII and ligated to HindIII-digested pGEMtox vector DNA. *E. coli* strain NM522 was transformed with ligation mixes. Correctly assembled constructs were identified by restriction enzyme digestion of plasmid DNA from isolated colonies. The plasmid with the new BamHI site was called pGEMtox BamHI. The plasmid with the new PvuI site was called pGEMtox PvuI. The ClaI fragment containing the BamHI site from plasmid pGEMtox BamHI was ligated to the phosphatased ClaI vector-containing fragment from pGEMtox PvuI. *E. coli* strain NM522 was transformed with ligation mixes. Correctly assembled constructs were identified by PCR analysis with primer set C/D, and by restriction digestion. The plasmid with both new restriction enzyme sites was called pGEMtox BamHI/PvuI.

A completed expression vector was assembled with insert from pGEMtox BamHI/PvuI and vector from pMYC1050ΔBamHI (FIGS. 3 and 4). Gel-purified insert was prepared from pGEMtoxBamHI/PvuI by NsiI digestion, and ScaI digestion (to remove contaminating vector). It was ligated to gel-purified NsiI-digested vector-containing pMYC1050ΔBamHI DNA. *E. coli* strain NM522 was transformed with the ligation mixes, and transformation mixes were plated on LB agar containing tetracycline at 12 μg/ml. Colonies containing the NsiI insert were identified by colony hybridization and autoradiography. Inserts were oriented by PCR, using primer set A/D, which bridges an NsiI cloning site, and agarose-TBE gel electrophoresis. The correctly assembled plasmid is called pMYC2224. DNA and protein sequences of the toxin are found in SEQ ID NOS. 18 and 19, respectively. A lactose-inducible *P. fluorescens* strain was electroporated with correctly assembled plasmid DNA. Transformation mixes were plated on LB agar containing tetracycline at 20 μg/ml. Plasmid DNA was prepared from *P. fluorescens* for use in subsequent cloning experiments.

EXAMPLE 2

Subcloning the cryIF Hypervariable Region into pMYC2224

A DNA fragment containing the hypervariable region from cryIF (pMYC1260) was exchanged for the BamHI- PvuI toxin-containing DNA fragment from pMYC2224 (FIG. 4). Since the coding sequence contains a preexisting BamHI site, BglII was chosen for cloning. The 4-base overhangs of BamHI and BglII are compatible, permitting ligation while eliminating both sites from the junction. It was necessary to synthesize a new primer for PCR:

"L" (SEQ ID NO. 8)

5' GAGTGGGAAGCAGATCTTAATAATGCACAATTAAGG 3'

A toxin-containing DNA fragment was generated by PCR with primers L/D on template pMYC1260. The DNA was digested with BglII and PvuI for subcloning. Since the tetAR locus contains multiple PvuI sites, it was necessary to isolate the vector-containing DNA on two separate fragments. To obtain the first fragment, pMYC2224 was digested with BamHI×BstEII, and the large DNA fragment containing the Ptac-tetAR locus-rep functions was gel-purified. To obtain the second fragment, pMYC2224 was digested with BstEII× PvuI, and the DNA fragment containing the vector-protoxin module was gel-purified. A three-piece ligation was set up and used for *E. coli* strain NM522 transformation. Grossly correct plasmids were identified by PCR analysis and agarose-TBE gel electrophoresis using the primer set N/O, which bridges the BamHI/BglII fusion junction.

"N" (tac promoter) (SEQ ID NO. 9)

5' TTAATCATCGGCTCGTA 3'

"O" (SEQ ID NO. 10)

5' ACTCGATCGATATGATA(GA)TCCGT 3'

The correct plasmid was named pMYC2239. It consists of cryIA(c) at the amino-terminus, cryIF up to the toxin/protoxin junction, and cryIA(b) through the protoxin segment. The toxin DNA and protein sequences are in SEQ ID NOS. 20 and 21, respectively.

EXAMPLE 3

Construction of the *P. fluorescens* Expression Plasmids pMYC1260 and pMYC2047

The cloned toxin gene cryIF can be modified for expression in *P. fluorescens* in the following way:

1. A plasmid containing the pKK223-3 rrnB termination sequences in the pTJS260-derived vector (Dr. Donald Helinski, U.C. San Diego) can be made by ligating the BamHI-ScaI fragment containing the Ptac promoter and rrnB terminator from pKK223-3 (Pharmacia *E. coli* vector) into the BamHI to blunted KpnI vector fragment of pMYC1197 (described in EP 0 417 564). The assembled plasmid is recovered following transformation of *E. coli* and growth under tetracycline selection.

2. A plasmid containing the Ptac-promoted cryIF toxin gene can be made by ligating toxin gene-containing NdeI-Nde-I fragment (with ends blunted using DNA polymerase and dNTPs) of about 3800 bp from pMYC1603 (from NRRL B-18517) into the blunted EcoRI and HindIII sites of pKK223-3. The Ptac-promoted cryIF toxin plasmid can be recovered following transformation of *E. coli*, grown under ampicillin selection, and screening for plasmids with inserts in the proper orientation for expression from the Ptac promoter by techniques well known in the art.

3. The Ptac-promoted cryIF toxin can be assembled into the pTJS260-derived vector in a three-piece ligation using the 2.4 kb DNA fragment having BamHI and ApaI ends from the plasmid pTJS260, ApaI to HindIII fragment of 8.5 kb containing the replication region of the plasmnid from step 1 above, and a HindIII to partial BamHI fragment containing the Ptac promoter and cryIF toxin gene from step 2 above.

The resulting pTJS260-derived cryIF toxin expression plasmid (pMYC1260) can be introduced into *P. fluorescens* by electroporation.

4. pMYC2047 can be constructed by ligating an SpeI to KpnI fragment obtained through PCR of a suitable cryIF template with primers H and K followed by digestion with SpeI and KpnI and gel purification, an ApaI to KpnI fragment of ca. 10 kb from the plasmid of step 3, and the ApaI to SpeI fragment of ca. 2600 bp from pMYC1197 containing the Ptac promoter. The correct cryIF toxin expression plasmids are determined by restriction enzyme digestion of plasmids following electroporation into *Pseudomonas fluorescens*.

EXAMPLE 4
Construction of a cryIF/cryIA(b) Chimera

Figure 5:
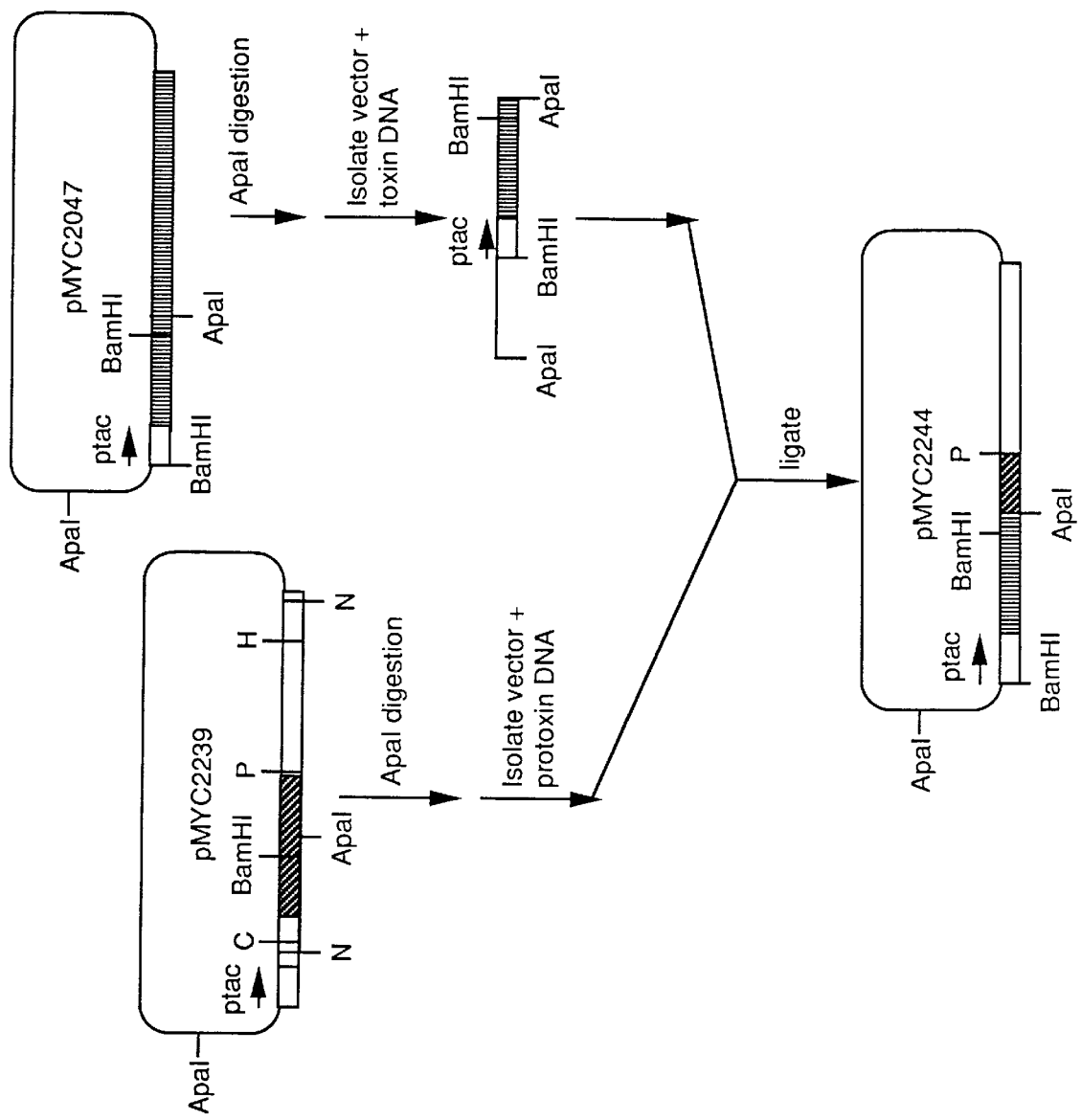
FIG. 5—The small ApaI DNA fragment of pMYC2047 is substituted for the homologous region of pMYC2239 to give plasmid pMYC2244. This chimera consists of cryIF in the toxin region and cryIA(b) in the protoxin. C=ClaI, H=HindIII, N=NsiI, P=PvuI.

The cryIa(c) segment at the amino-terminus can be replaced by the cryIF coding sequence by a simple, straightforward swap (FIG. 5). Both the tetAR locus and cryIF coding sequence contain an ApaI site. A small ApaI fragment containing a portion of the tetAR genes and the amino-terminus of cryIF can be isolated from pMYC2047 and ligated to the large ApaI vector-containing fragment from pMYC2239. A *P. fluorescens* lactose-inducible strain can be electroporated with the ligation mix and plated on LB agar containing tetracycline at 20 μg/ml. Lactose-inducible strains are known to those skilled in the art and are described, for example, in U.S. Pat. No. 5,169,760. Correct orientation of the ApaI fragment reconstitutes tetracycline resistance. A clone produced in this manner was shown to be grossly correct by restriction enzyme digestion, and it was named pMYC2244. The toxin DNA sequence is shown in SEQ ID NO. 22, and the predicted protein sequence is shown in SEQ ID NO. 23.

EXAMPLE 5
Construction of a Limited Codon Rework of cryIF

Figure 6:
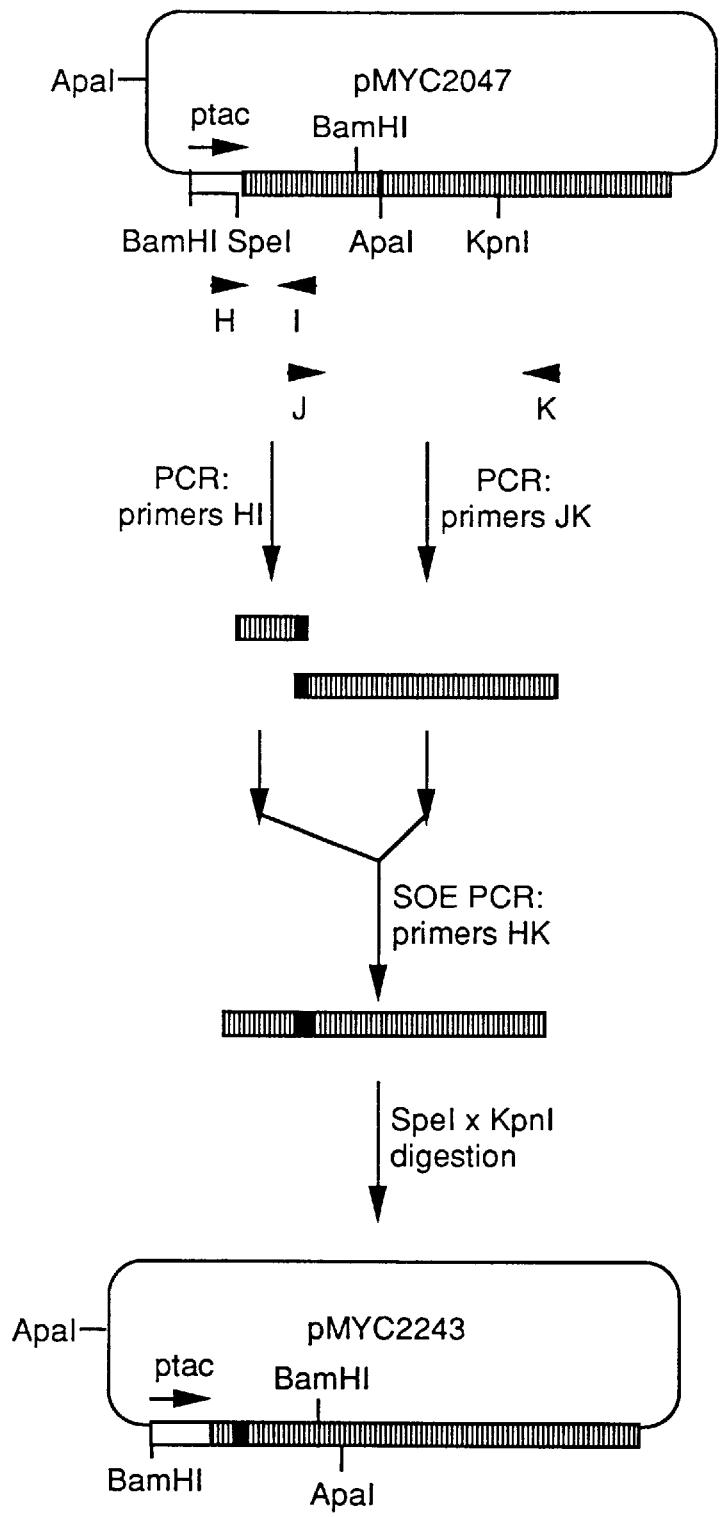
FIG. 6—Silent codon changes are introduced into the cryIF toxin by SOE. The SpeI-KpnI PCR DNA fragment with the changes is substituted for the homologous toxin-containing fragment in pMYC2047. The resulting plasmid is pMYC2243. Letters H through K below the arrows correspond to oligonucleotide primers in the text.
Figure 7:
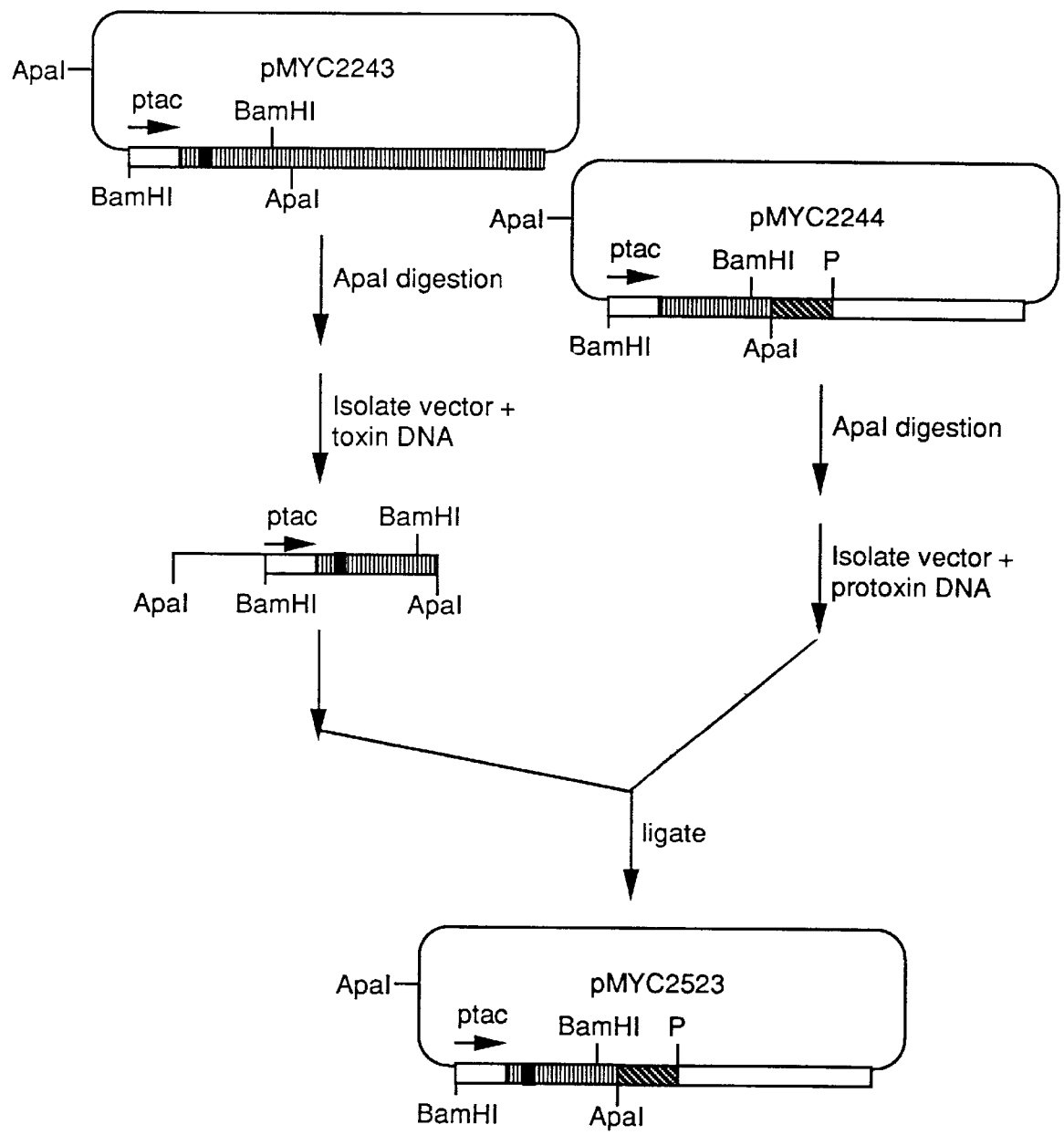
FIG. 7—Silent codon changes are introduced into pMYC2244 by substitution of the homologous fragment with the small ApaI DNA fragment of pMYC2243. The final plasmid is pMYC2523. P=PvuI.

Codon usage in Pseudomonas spp. favors G or C in the wobble position of triplet codons, as determined by analysis of genes in the GenBank/EMBL sequence libraries. A limited region of the cryIF gene was reworked by SOE to incorporate favored wobble position changes that were silent (FIG. 6). Oligos used are shown below:

"H" (SEQ ID NO. 11)

5' GGACTAGTAAAAAGGAGATAACCATG-
GAAAATAATATTCAAAATC 3'

"I" (SEQ ID NO. 12)
5' TCCAGCGGCAGGCGGCCGGTGCTGCGT-
TCTTCGTTCAGTATTTCTACT TCAGGATTATTTAAAC 3'

"J" (SEQ ID NO. 13)

5' AACGCAGCACCGGCCGCCTGCCGCTGGA-
CATCAGCCTGAGCCTTACAC GTTTCCTTTGAGTGAA 3'

"K" (SEQ ID NO. 14)

5' CATCAAAGGTACCTGGT 3'

Two separate PCR reactions were done on pMYC2047 template with primer sets H/I or J/K. Amplified DNA fragments were called HI or JK. A second PCR reaction was set up by mixing fragments HI and JK and PCR amplifing with primer set H/K. The larger SOE DNA was gel-purified and digested with SpeI×KpnI. A three-piece ligation was set up with SpeI-ApaI Ptac-tetAR locus DNA, ApaI-KpnI vector-protoxin module DNA, and SpeI-KpnI PCR DNA. A *P. fluorescens* lactose-inducible strain can be electroporated with the ligation mix. Grossly correct clones can be identified by PCR analysis using the primer set P/Q and agarose-TBE gel electrophoresis. Oligo P (SEQ ID NO. 15) was designed to discriminate between the wild-type and codon-reworked gene.

"P" (SEQ ID NO. 15)

5' TGCCGCTGGACATCAGCCTGAG 3'

"Q" (SEQ ID NO. 16)

5' TCTAGAGCGGCCGCTTATAC(CT)CGATC-
GATATGATA(GA)TCCGT 3'

The complete plasmid was named pMYC2243. The toxin DNA sequence is shown in SEQ ID NO. 24. The toxin protein sequence is predicted to be unchanged, and is shown in SEQ ID NO. 25.

EXAMPLE 6
Construction of the cryIF/cryIA(b) Chimera Containing the Limited Codon Rework The construct was assembled (FIG. 7) using the same ApaI fragment exchange strategy as for pMYC2244 (cryIF/cryIA(b)) above. The small, toxin-tetAR locus ApaI DNA fragment was gel-purified from pMYC2243. The larger vector-protoxin module ApaI DNA fragment was gel-purified from pMYC2244. The completed plasmid was named pMYC2523. Predicted DNA and protein sequences are in SEQ ID NOS. 26 and 27, respectively.

EXAMPLE 7
Comparative Expression of Toxins from pMYC2243 and pMYC2523

Toxin expression in *P. fluorescens* was analyzed as described above. At 24 and 48 hours post-induction, the pMYC2523-containing strain produced more toxin than the pMYC2243-containing strain. Toxin specific activity on *Spodoptera exigua* was statistically unchanged.

Figure 8:
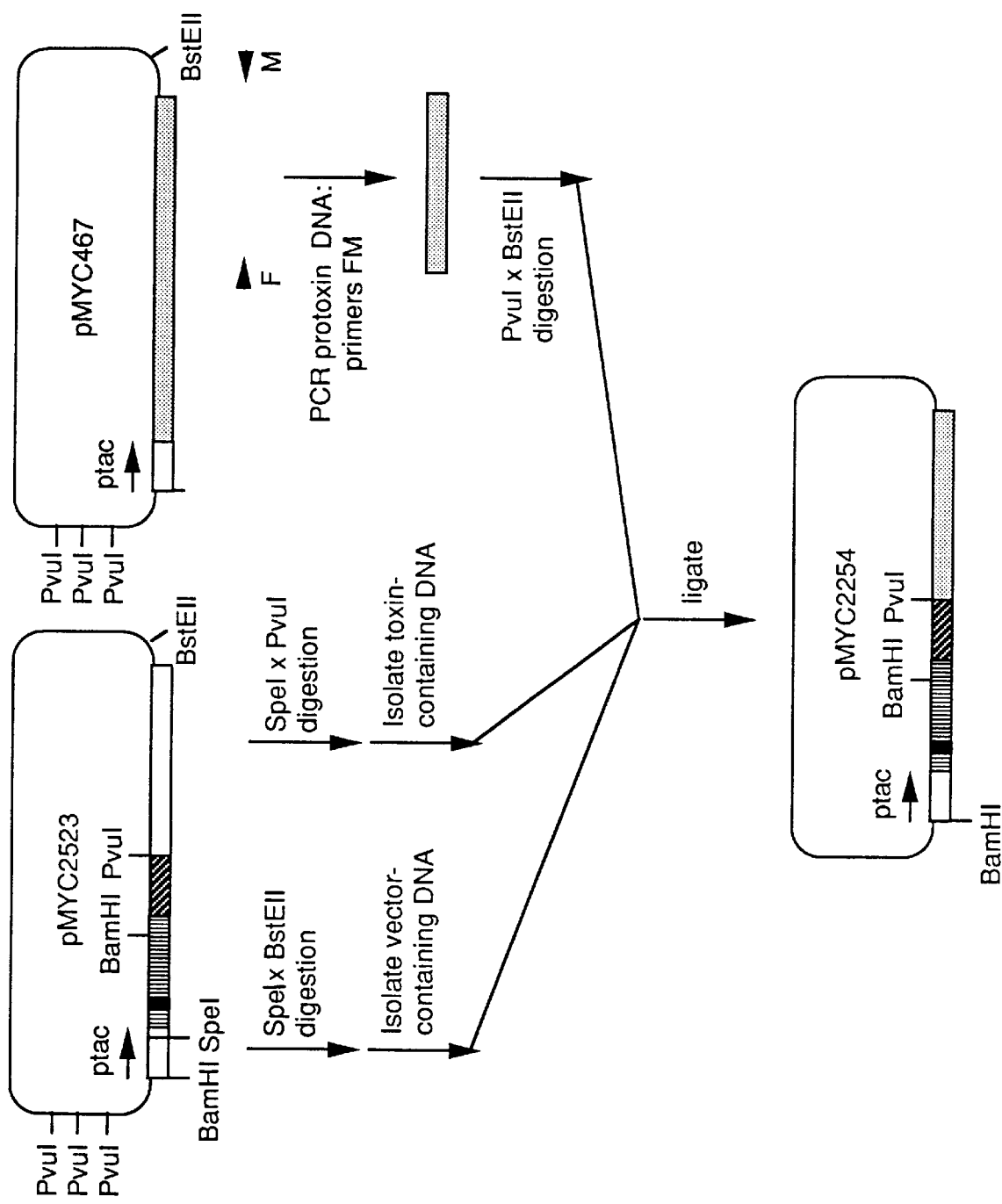
FIG. 8—A chimeric toxin containing the 436 protoxin is constructed by substituting a PCR-generated PvuI-BstEII protoxin DNA for the homologous fragment in pMYC2523. The final plasmid is pMYC2254. Letters F and M below the arrows correspond to oligonucleotide primers in the text.

EXAMPLE 8
Construction of the cryIF/436 Chimera Containing the Limited Codon Rework A second type of chimeric toxin was assembled by substituting the 436 protoxin module for the cryIA(b) protoxin in pMYC2523 (FIG. 8). The 436 protoxin sequence consists of cryIA(c) sequence except at the very C-terminus (See U.S. Pat. Nos. 5,128,130 and 5,169,760, incorporated herein by reference in their entirety). Protoxin DNA for cloning was generated by PCR with the primer set F/M using a plasmid such as pMYC467 (U.S. Pat. No. 5,169,760) as a template.

"M" (SEQ ID NO. 17)

5' AGGCTTCCATAGATACCTTGTGCG 3'

PCR DNA was digested with PvuI×BstEII. A three-piece ligation was set up with SpeI-PvuI toxin DNA from pMYC2523, SpeI-BstEII vector DNA from pMYC2523, and PvuI-BstEII PCR protoxin module DNA. A lactose-inducible *P. fluorescens* strain was electroporated with the ligation mix. Grossly correct plasmids were identified by PCR with primer set F/G and screening for slight size increase by agarose-TBE gel electrophoresis. The construct was named pMYC2254. Predicted DNA and protein sequences are found in SEQ ID NOS. 28 and 29, respectively.

EXAMPLE 9
Comparative Expression of Toxins from pMYC2243 and pMYC2254

Toxin expression in *P. fluorescens* was analyzed as described above. Toxin expression from pMYC2254 was improved over pMYC2243 expression.

EXAMPLE 10
Insertion of the Gene Encoding the Chimeric Toxin Into Plants

One aspect of the subject invention is the transformation of plants with genes encoding the insecticidal toxin. The transformed plants are resistant to attack by the target pest.

The gene encoding the chimeric toxin, as disclosed herein, can be inserted into plant cells using a variety of techniques which are well known in the art. For example, a large number of cloning vectors comprising a replication system in *E. coli* and a marker that permits selection of the transformed cells are available for preparation for the insertion of foreign genes into higher plants. The vectors comprise, for example, pBR322, pUC series, M13mp series, pACYC184, etc. Accordingly, the sequence encoding the *B.t.* toxin can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted.

The use of T-DNA for the transformation of plant cells has been intensively researched and sufficiently described in EP 0 120 516; Hoekema (1985) In: *The Binary Plant Vector System*, Offset-durkkerij Kanters B. V., Alblasserdam, Chapter 5; Fraley et al., *Crit. Rev. Plant Sci.* 4:1–46; and An et al (1985) *EMBO J.* 4:277–287.

Once the inserted DNA has been integrated in the genome, it is relatively stable there and, as a rule, does not come out again. It normally contains a selection marker that confers on the transformed plant cells resistance to a biocide or an antibiotic, such as kanamycin, G 418, bleomycin, hygromycin, or chloramphenicol, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformation agent, fusion, injection, or electroporation as well as other possible methods. If agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in agrobacteria. The intermediate vector can be transferred into *Agrobacterium tumefaciens* by means of a helper plasmid (conjugation). Binary vectors can replicate themselves both in *E. coli* and in agrobacteria. They comprise a selection marker gene and a linker or polylinker which are framed by the right and left T-DNA border regions. They can be transformed directly into agrobacteria (Holsters et al [1978] *Mol. Gen. Genet.* 163:181–187). The agrobacterium used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed traits to progeny plants. Such plants can be grown in the normal manner and crossed with plants that have the same transformed hereditary factors or other hereditary factors. The resulting hybrid individuals have the corresponding phenotypic properties.

In a preferred embodiment of the subject invention, plants will be transformed with genes wherein the codon usage has been optimized for plants. Also, advantageously, plants encoding a truncated toxin will be used. The truncated toxin typically will encode about 55% to about 80% of the full length toxin. Methods for creating synthetic genes for use in plants are known in the art.

EXAMPLE 11

Cloning of the Gene Encoding the Chimeric Toxin Into Insect Viruses

A number of viruses are known to infect insects. These viruses include, for example, baculoviruses and entomopoxviruses. In one embodiment of the subject invention, genes encoding the insecticidal toxins, as described herein, can be placed within the genome of the insect virus, thus enhancing the pathogenicity of the virus. Methods for constructing insect viruses which comprise the chimeric toxin gene are well known and readily practiced by those skilled in the art. These procedures are described, for example, in Merryweather et al (Merryweather, A. T., U. Weyer, M. P .G. Harris, M. Hirst, T. Booth, R. D. Possee (1990) *J. Gen. Virol.* 71:1535–1544) and Martens et al. (Martens, J. W. M., G. Honee, D. Zuidema, J. W. M. van Lent, B. Visser, J. M. Vlak (1990) *Appl. Environmental Microbiol.* 56(9):2764–2770).

It should be understood that the examples and embodiments described herein are for illustrative purposes only and that various modifications or changes in light thereof will be suggested to persons skilled in the art and are to be included within the spirit and purview of this application and the scope of the appended claims.

SEQUENCE LISTING ( 1 ) GENERAL INFORMATION:

( i i i ) NUMBER OF SEQUENCES: 38

( 2 ) INFORMATION FOR SEQ ID NO:1:

( i ) SEQUENCE CHARACTERISTICS:
        ( A ) LENGTH: 39 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:1:

GCATACTAGT AGGAGATTTC CATGGATAAC AATCCGAAC        39

( 2 ) INFORMATION FOR SEQ ID NO:2:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:2:

GGATCCGCTT CCCAGTCT        18

( 2 ) INFORMATION FOR SEQ ID NO:3:

( i ) SEQUENCE CHARACTERISTICS:
        ( A ) LENGTH: 29 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:3:

AGAGAGTGGG AAGCGGATCC TACTAATCC        29

( 2 ) INFORMATION FOR SEQ ID NO:4:

( i ) SEQUENCE CHARACTERISTICS:
        ( A ) LENGTH: 28 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:4:

TGGATACTCG ATCGATATGA TAATCCGT        28

( 2 ) INFORMATION FOR SEQ ID NO:5:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:5:

TAATAAGAGC TCCTATGT					18

( 2 ) INFORMATION FOR SEQ ID NO:6:

( i ) SEQUENCE CHARACTERISTICS:
        ( A ) LENGTH: 28 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:6:

TATCATATCG ATCGAGTATC CAATTTAG					28

( 2 ) INFORMATION FOR SEQ ID NO:7:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:7:

GTCACATAGC CAGCTGGT					18

( 2 ) INFORMATION FOR SEQ ID NO:8:

( i ) SEQUENCE CHARACTERISTICS:
        ( A ) LENGTH: 36 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:8:

GAGTGGGAAG CAGATCTTAA TAATGCACAA TTAAGG					36

( 2 ) INFORMATION FOR SEQ ID NO:9:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:9:

TTAATCATCG GCTCGTA					17

( 2 ) INFORMATION FOR SEQ ID NO:10:

( i ) SEQUENCE CHARACTERISTICS:
        ( A ) LENGTH: 23 bases
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:10:

ACTCGATCGA TATGATARTC CGT					23

( 2 ) INFORMATION FOR SEQ ID NO:11:

( i ) SEQUENCE CHARACTERISTICS:
    ( A ) LENGTH: 45 bases
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:11:

GGACTAGTAA AAAGGAGATA ACCATGGAAA ATAATATTCA AAATC    45

( 2 ) INFORMATION FOR SEQ ID NO:12:

( i ) SEQUENCE CHARACTERISTICS:
    ( A ) LENGTH: 64 bases
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:12:

TCCAGCGGCA GGCGGCCGGT GCTGCGTTCT TCGTTCAGTA TTTCTACTTC AGGATTATTT    60

AAAC    64

( 2 ) INFORMATION FOR SEQ ID NO:13:

( i ) SEQUENCE CHARACTERISTICS:
    ( A ) LENGTH: 65 bases
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:13:

AACGCAGCAC CGGCCGCCTG CCGCTGGACA TCAGCCTGAG CCTTACACGT TTCCTTTTGA    60

GTGAA    65

( 2 ) INFORMATION FOR SEQ ID NO:14:

( i ) SEQUENCE CHARACTERISTICS:
    ( A ) LENGTH: 17 bases
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:14:

CATCAAAGGT ACCTGGT    17

( 2 ) INFORMATION FOR SEQ ID NO:15:

( i ) SEQUENCE CHARACTERISTICS:
    ( A ) LENGTH: 22 bases
    ( B ) TYPE: nucleic acid
    ( C ) STRANDEDNESS: single
    ( D ) TOPOLOGY: linear ( i i ) MOLECULE TYPE: DNA (synthetic)

( x i ) SEQUENCE DESCRIPTION: SEQ ID NO:15:

TGCCGCTGGA CATCAGCCTG AG    22

( 2 ) INFORMATION FOR SEQ ID NO:16:

( i ) SEQUENCE CHARACTERISTICS:

(A) LENGTH: 41 bases
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO:16:

TCTAGAGCGG CCGCTTATAC YCGATCGATA TGATARTCCG T                              41

(2) INFORMATION FOR SEQ ID NO:17:

(i) SEQUENCE CHARACTERISTICS:
(A) LENGTH: 24 bases
(B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO:17:

AGGCTTCCAT AGATACCTTG TGCG                                                 24

(2) INFORMATION FOR SEQ ID NO:18:

(i) SEQUENCE CHARACTERISTICS:
(A) LENGTH: 3465 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:18:

ATGGATAACA ATCCGAACAT CAATGAATGC ATTCCTTATA ATTGTTTAAG TAACCCTGAA            60
GTAGAAGTAT TAGGTGGAGA AAGAATAGAA ACTGGTTACA CCCCAATCGA TATTTCCTTG           120
TCGCTAACGC AATTTCTTTT GAGTGAATTT GTTCCCGGTG CTGGATTTGT GTTAGGACTA           180
GTTGATATAA TATGGGGAAT TTTTGGTCCC TCTCAATGGG ACGCATTTCT TGTACAAATT           240
GAACAGTTAA TTAACCAAAG AATAGAAGAA TTCGCTAGGA ACCAAGCCAT TTCTAGATTA           300
GAAGGACTAA GCAATCTTTA TCAAATTTAC GCAGAATCTT TTAGAGAGTG GAAGCGGAT            360
CCTACTAATC CAGCATTAAG AGAAGAGATG CGTATTCAAT TCAATGACAT GAACAGTGCC           420
CTTACAACCG CTATTCCTCT TTTTGCAGTT CAAAATTATC AAGTTCCTCT TTTATCAGTA           480
TATGTTCAAG CTGCAAATTT ACATTATCA GTTTTGAGAG ATGTTTCAGT GTTTGGACAA            540
AGGTGGGGAT TTGATGCCGC GACTATCAAT AGTCGTTATA ATGATTTAAC TAGGCTTATT           600
GGCAACTATA CAGATTATGC TGTACGCTGG TACAATACGG GATTAGAACG TGTATGGGA            660
CCGGATTCTA GAGATTGGGT AAGGTATAAT CAATTTAGAA GAGAATTAAC ACTAACTGTA           720
TTAGATATCG TTGCTCTGTT CCCGAATTAT GATAGTAGAA GATATCCAAT TCGAACAGTT           780
TCCCAATTAA CAAGAGAAAT TTATACAAAC CCAGTATTAG AAAATTTTGA TGGTAGTTTT           840
CGAGGCTCGG CTCAGGGCAT AGAAAGAAGT ATTAGGAGTC CACATTTGAT GGATATACTT           900
AACAGTATAA CCATCTATAC GGATGCTCAT AGGGGTTATT ATTATTGGTC AGGGCATCAA           960
ATAATGGCTT CTCCTGTAGG GTTTTCGGGG CCAGAATTCA CTTTTCCGCT ATATGGAACT          1020
ATGGGAAATG CAGCTCCACA ACAACGTATT GTTGCTCAAC TAGGTCAGGG CGTGTATAGA          1080
ACATTATCGT CCACTTTATA TAGAAGACCT TTTAATATAG GGATAAATAA TCAACAACTA          1140
TCTGTTCTTG ACGGGACAGA ATTTGCTTAT GGAACCTCCT CAAATTTGCC ATCCGCTGTA          1200
TACAGAAAAA GCGGAACGGT AGATTCGCTG GATGAAATAC CGCCACAGAA TAACAACGTG          1260

| | | | | | |
|---|---|---|---|---|---|
| CCACCTAGGC | AAGGATTTAG | TCATCGATTA | AGCCATGTTT | CAATGTTTCG | TTCAGGCTTT | 1320
| AGTAATAGTA | GTGTAAGTAT | AATAAGAGCT | CCTATGTTCT | CTTGGATACA | TCGTAGTGCT | 1380
| GAATTTAATA | ATATAATTCC | TTCATCACAA | ATTACACAAA | TACCTTTAAC | AAAATCTACT | 1440
| AATCTTGGCT | CTGGAACTTC | TGTCGTTAAA | GGACCAGGAT | TTACAGGAGG | AGATATTCTT | 1500
| CGAAGAACTT | CACCTGGCCA | GATTTCAACC | TTAAGAGTAA | ATATTACTGC | ACCATTATCA | 1560
| CAAAGATATC | GGGTAAGAAT | TCGCTACGCT | TCTACCACAA | ATTTACAATT | CCATACATCA | 1620
| ATTGACGGAA | GACCTATTAA | TCAGGGGAAT | TTTTCAGCAA | CTATGAGTAG | TGGGAGTAAT | 1680
| TTACAGTCCG | GAAGCTTTAG | GACTGTAGGT | TTTACTACTC | CGTTTAACTT | TTCAAATGGA | 1740
| TCAAGTGTAT | TTACGTTAAG | TGCTCATGTC | TTCAATTCAG | GCAATGAAGT | TTATATAGAT | 1800
| CGAATTGAAT | TTGTTCCGGC | AGAAGTAACC | TTTGAGGCAG | AATATGATTT | AGAAAGAGCA | 1860
| CAAAAGGCGG | TGAATGAGCT | GTTTACTTCT | TCCAATCAAA | TCGGGTAAAA | AACAGATGTG | 1920
| ACGGATTATC | ATATCGATCG | AGTATCCAAT | TTAGTTGAGT | GTTTATCTGA | TGAATTTTGT | 1980
| CTGGATGAAA | AAAAAGAATT | GTCCGAGAAA | GTCAAACATG | CGAAGCGACT | TAGTGATGAG | 2040
| CGGAATTTAC | TTCAAGATCC | AAACTTTAGA | GGGATCAATA | GACAACTAGA | CCGTGGCTGG | 2100
| AGAGGAAGTA | CGGATATTAC | CATCCAAGGA | GGCGATGACG | TATTCAAAGA | GAATTACGTT | 2160
| ACGCTATTGG | GTACCTTTGA | TGAGTGCTAT | CCAACGTATT | TATATCAAAA | AATAGATGAG | 2220
| TCGAAATTAA | AAGCCTATAC | CCGTTACCAA | TTAAGAGGGT | ATATCGAAGA | TAGTCAAGAC | 2280
| TTAGAAATCT | ATTTAATTCG | CTACAATGCC | AAACACGAAA | CAGTAAATGT | GCCAGGTACG | 2340
| GGTTCCTTAT | GGCCGCTTTC | AGCCCCAAGT | CCAATCGGAA | AATGTGCCCA | TCATTCCCAT | 2400
| CATTTCTCCT | TGGACATTGA | TGTTGGATGT | ACAGACTTAA | ATGAGGACTT | AGGTGTATGG | 2460
| GTGATATTCA | AGATTAAGAC | GCAAGATGGC | CATGCAAGAC | TAGGAAATCT | AGAATTTCTC | 2520
| GAAGAGAAAC | CATTAGTAGG | AGAAGCACTA | GCTCGTGTGA | AAAGAGCGGA | GAAAAAATGG | 2580
| AGAGACAAAC | GTGAAAAATT | GGAATGGGAA | ACAAATATTG | TTTATAAAGA | GGCAAAAGAA | 2640
| TCTGTAGATG | CTTTATTTGT | AAACTCTCAA | TATGATAGAT | TACAAGCGGA | TACCAACATC | 2700
| GCGATGATTC | ATGCGGCAGA | TAAACGCGTT | CATAGCATTC | GAGAAGCTTA | TCTGCCTGAG | 2760
| CTGTCTGTGA | TTCCGGGTGT | CAATGCGGCT | ATTTTTGAAG | AATTAGAAGG | GCGTATTTTC | 2820
| ACTGCATTCT | CCCTATATGA | TGCGAGAAAT | GTCATTAAAA | ATGGTGATTT | TAATAATGGC | 2880
| TTATCCTGCT | GGAACGTGAA | AGGGCATGTA | GATGTAGAAG | AACAAAACAA | CCACCGTTCG | 2940
| GTCCTTGTTG | TTCCGGAATG | GGAAGCAGAA | GTGTCACAAG | AAGTTCGTGT | CTGTCCGGGT | 3000
| CGTGGCTATA | TCCTTCGTGT | CACAGCGTAC | AAGGAGGGAT | ATGGAGAAGG | TTGCGTAACC | 3060
| ATTCATGAGA | TCGAGAACAA | TACAGACGAA | CTGAAGTTTA | GCAACTGTGT | AGAAGAGGAA | 3120
| GTATATCCAA | ACAACACGGT | AACGTGTAAT | GATTATACTG | CGACTCAAGA | AGAATATGAG | 3180
| GGTACGTACA | CTTCTCGTAA | TCGAGGATAT | GACGGAGCCT | ATGAAAGCAA | TTCTTCTGTA | 3240
| CCAGCTGATT | ATGCATCAGC | CTATGAAGAA | AAAGCATATA | CAGATGGACG | AAGAGACAAT | 3300
| CCTTGTGAAT | CTAACAGAGG | ATATGGGGAT | TACACACCAC | TACCAGCTGG | CTATGTGACA | 3360
| AAAGAATTAG | AGTACTTCCC | AGAAACCGAT | AAGGTATGGA | TTGAGATCGG | AGAAACGGAA | 3420
| GGAACATTCA | TCGTGGACAG | CGTGGAATTA | CTTCTTATGG | AGGAA | | 3465

( 2 ) INFORMATION FOR SEQ ID NO:19:

( i ) SEQUENCE CHARACTERISTICS:
        ( A ) LENGTH: 1155 amino acids (B) TYPE: amino acid
(C) STRANDEDNESS: single
(D) TOPOLOGY: linear (ii) MOLECULE TYPE: protein (xi) SEQUENCE DESCRIPTION: SEQ ID NO:19:

```
Met Asp Asn Asn Pro Asn Ile Asn Glu Cys Ile Pro Tyr Asn Cys Leu
  1               5                  10                  15

Ser Asn Pro Glu Val Glu Val Leu Gly Gly Glu Arg Ile Glu Thr Gly
                 20                  25                  30

Tyr Thr Pro Ile Asp Ile Ser Leu Ser Leu Thr Gln Phe Leu Leu Ser
             35                  40                  45

Glu Phe Val Pro Gly Ala Gly Phe Val Leu Gly Leu Val Asp Ile Ile
         50                  55                  60

Trp Gly Ile Phe Gly Pro Ser Gln Trp Asp Ala Phe Leu Val Gln Ile
 65                  70                  75                  80

Glu Gln Leu Ile Asn Gln Arg Ile Glu Glu Phe Ala Arg Asn Gln Ala
                 85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Arg Ser Ile Arg Ser Pro His Leu Met Asp Ile Leu Asn Ser Ile Thr
    290                 295                 300

Ile Tyr Thr Asp Ala His Arg Gly Tyr Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
    370                 375                 380
```

```
Gly  Thr  Glu  Phe  Ala  Tyr  Gly  Thr  Ser  Ser  Asn  Leu  Pro  Ser  Ala  Val
385                      390                 395                           400

Tyr  Arg  Lys  Ser  Gly  Thr  Val  Asp  Ser  Leu  Asp  Glu  Ile  Pro  Pro  Gln
                    405                 410                      415

Asn  Asn  Asn  Val  Pro  Pro  Arg  Gln  Gly  Phe  Ser  His  Arg  Leu  Ser  His
               420                 425                           430

Val  Ser  Met  Phe  Arg  Ser  Gly  Phe  Ser  Asn  Ser  Ser  Val  Ser  Ile  Ile
          435                      440                      445

Arg  Ala  Pro  Met  Phe  Ser  Trp  Ile  His  Arg  Ser  Ala  Glu  Phe  Asn  Asn
     450                      455                 460

Ile  Ile  Pro  Ser  Ser  Gln  Ile  Thr  Gln  Ile  Pro  Leu  Thr  Lys  Ser  Thr
465                      470                 475                           480

Asn  Leu  Gly  Ser  Gly  Thr  Ser  Val  Val  Lys  Gly  Pro  Gly  Phe  Thr  Gly
                    485                 490                           495

Gly  Asp  Ile  Leu  Arg  Arg  Thr  Ser  Pro  Gly  Gln  Ile  Ser  Thr  Leu  Arg
               500                 505                      510

Val  Asn  Ile  Thr  Ala  Pro  Leu  Ser  Gln  Arg  Tyr  Arg  Val  Arg  Ile  Arg
          515                 520                      525

Tyr  Ala  Ser  Thr  Thr  Asn  Leu  Gln  Phe  His  Thr  Ser  Ile  Asp  Gly  Arg
     530                      535                 540

Pro  Ile  Asn  Gln  Gly  Asn  Phe  Ser  Ala  Thr  Met  Ser  Ser  Gly  Ser  Asn
545                      550                 555                           560

Leu  Gln  Ser  Gly  Ser  Phe  Arg  Thr  Val  Gly  Phe  Thr  Thr  Pro  Phe  Asn
                    565                 570                           575

Phe  Ser  Asn  Gly  Ser  Ser  Val  Phe  Thr  Leu  Ser  Ala  His  Val  Phe  Asn
               580                 585                      590

Ser  Gly  Asn  Glu  Val  Tyr  Ile  Asp  Arg  Ile  Glu  Phe  Val  Pro  Ala  Glu
          595                 600                      605

Val  Thr  Phe  Glu  Ala  Glu  Tyr  Asp  Leu  Glu  Arg  Ala  Gln  Lys  Ala  Val
     610                      615                 620

Asn  Glu  Leu  Phe  Thr  Ser  Ser  Asn  Gln  Ile  Gly  Leu  Lys  Thr  Asp  Val
625                      630                 635                           640

Thr  Asp  Tyr  His  Ile  Asp  Arg  Val  Ser  Asn  Leu  Val  Glu  Cys  Leu  Ser
               645                 650                      655

Asp  Glu  Phe  Cys  Leu  Asp  Glu  Lys  Lys  Glu  Leu  Ser  Glu  Lys  Val  Lys
          660                 665                      670

His  Ala  Lys  Arg  Leu  Ser  Asp  Glu  Arg  Asn  Leu  Leu  Gln  Asp  Pro  Asn
     675                      680                 685

Phe  Arg  Gly  Ile  Asn  Arg  Gln  Leu  Asp  Arg  Gly  Trp  Arg  Gly  Ser  Thr
     690                      695                 700

Asp  Ile  Thr  Ile  Gln  Gly  Gly  Asp  Asp  Val  Phe  Lys  Glu  Asn  Tyr  Val
705                      710                 715                           720

Thr  Leu  Leu  Gly  Thr  Phe  Asp  Glu  Cys  Tyr  Pro  Thr  Tyr  Leu  Tyr  Gln
                    725                 730                           735

Lys  Ile  Asp  Glu  Ser  Lys  Leu  Lys  Ala  Tyr  Thr  Arg  Tyr  Gln  Leu  Arg
               740                 745                      750

Gly  Tyr  Ile  Glu  Asp  Ser  Gln  Asp  Leu  Glu  Ile  Tyr  Leu  Ile  Arg  Tyr
          755                 760                      765

Asn  Ala  Lys  His  Glu  Thr  Val  Asn  Val  Pro  Gly  Thr  Gly  Ser  Leu  Trp
     770                      775                 780

Pro  Leu  Ser  Ala  Pro  Ser  Pro  Ile  Gly  Lys  Cys  Ala  His  His  Ser  His
785                      790                 795                           800

His  Phe  Ser  Leu  Asp  Ile  Asp  Val  Gly  Cys  Thr  Asp  Leu  Asn  Glu  Asp
                    805                 810                           815
```

```
Leu Gly Val Trp Val Ile Phe Lys Ile Lys Thr Gln Asp Gly His Ala
            820                 825                 830
Arg Leu Gly Asn Leu Glu Phe Leu Glu Glu Lys Pro Leu Val Gly Glu
        835                 840                 845
Ala Leu Ala Arg Val Lys Arg Ala Glu Lys Lys Trp Arg Asp Lys Arg
    850                 855                 860
Glu Lys Leu Glu Trp Glu Thr Asn Ile Val Tyr Lys Glu Ala Lys Glu
865                 870                 875                 880
Ser Val Asp Ala Leu Phe Val Asn Ser Gln Tyr Asp Arg Leu Gln Ala
                885                 890                 895
Asp Thr Asn Ile Ala Met Ile His Ala Ala Asp Lys Arg Val His Ser
            900                 905                 910
Ile Arg Glu Ala Tyr Leu Pro Glu Leu Ser Val Ile Pro Gly Val Asn
        915                 920                 925
Ala Ala Ile Phe Glu Glu Leu Glu Gly Arg Ile Phe Thr Ala Phe Ser
    930                 935                 940
Leu Tyr Asp Ala Arg Asn Val Ile Lys Asn Gly Asp Phe Asn Asn Gly
945                 950                 955                 960
Leu Ser Cys Trp Asn Val Lys Gly His Val Asp Val Glu Glu Gln Asn
                965                 970                 975
Asn His Arg Ser Val Leu Val Val Pro Glu Trp Glu Ala Glu Val Ser
            980                 985                 990
Gln Glu Val Arg Val Cys Pro Gly Arg Gly Tyr Ile Leu Arg Val Thr
        995                 1000                1005
Ala Tyr Lys Glu Gly Tyr Gly Glu Gly Cys Val Thr Ile His Glu Ile
    1010                1015                1020
Glu Asn Asn Thr Asp Glu Leu Lys Phe Ser Asn Cys Val Glu Glu Glu
1025                1030                1035                1040
Val Tyr Pro Asn Asn Thr Val Thr Cys Asn Asp Tyr Thr Ala Thr Gln
                1045                1050                1055
Glu Glu Tyr Glu Gly Thr Tyr Thr Ser Arg Asn Arg Gly Tyr Asp Gly
            1060                1065                1070
Ala Tyr Glu Ser Asn Ser Ser Val Pro Ala Asp Tyr Ala Ser Ala Tyr
        1075                1080                1085
Glu Glu Lys Ala Tyr Thr Asp Gly Arg Arg Asp Asn Pro Cys Glu Ser
    1090                1095                1100
Asn Arg Gly Tyr Gly Asp Tyr Thr Pro Leu Pro Ala Gly Tyr Val Thr
1105                1110                1115                1120
Lys Glu Leu Glu Tyr Phe Pro Glu Thr Asp Lys Val Trp Ile Glu Ile
                1125                1130                1135
Gly Glu Thr Glu Gly Thr Phe Ile Val Asp Ser Val Glu Leu Leu Leu
            1140                1145                1150
Met Glu Glu
    1155
```

( 2 ) INFORMATION FOR SEQ ID NO:20:

( i ) SEQUENCE CHARACTERISTICS:
        ( A ) LENGTH: 3450 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

-continued

| | | | | | |
|---|---|---|---|---|---|
| ATGGATAACA | ATCCGAACAT | CAATGAATGC | ATTCCTTATA | ATTGTTTAAG | TAACCCTGAA | 60
| GTAGAAGTAT | TAGGTGGAGA | AAGAATAGAA | ACTGGTTACA | CCCCAATCGA | TATTTCCTTG | 120
| TCGCTAACGC | AATTTCTTTT | GAGTGAATTT | GTTCCGGTG | CTGGATTTGT | GTTAGGACTA | 180
| GTTGATATAA | TATGGGGAAT | TTTTGGTCCC | TCTCAATGGG | ACGCATTTCT | TGTACAAATT | 240
| GAACAGTTAA | TTAACCAAAG | AATAGAAGAA | TTCGCTAGGA | ACCAAGCCAT | TTCTAGATTA | 300
| GAAGGACTAA | GCAATCTTTA | TCAAATTTAC | GCAGAATCTT | TTAGAGAGTG | GGAAGCGGAT | 360
| CTTAATAATG | CACAATTAAG | GGAAGATGTG | CGTATTCGAT | TTGCTAATAC | AGACGACGCT | 420
| TTAATAACAG | CAATAAATAA | TTTTACACTT | ACAAGTTTTG | AAATCCCTCT | TTTATCGGTC | 480
| TATGTTCAAG | CGGCGAATTT | ACATTATCA | CTATTAAGAG | ACGCTGTATC | GTTTGGGCAG | 540
| GGTTGGGGAC | TGGATATAGC | TACTGTTAAT | AATCATTATA | ATAGATTAAT | AAATCTTATT | 600
| CATAGATATA | CGAAACATTG | TTTGGACACA | TACAATCAAG | GATTAGAAAA | CTTAAGAGGT | 660
| ACTAATACTC | GACAATGGGC | AAGATTCAAT | CAGTTTAGGA | GAGATTTAAC | ACTTACTGTA | 720
| TTAGATATCG | TTGCTCTTTT | TCCGAACTAC | GATGTTAGAA | CATATCCAAT | TCAAACGTCA | 780
| TCCCAATTAA | CAAGGGAAAT | TTATACAAGT | TCAGTAATTG | AGGATTCTCC | AGTTTCTGCT | 840
| AATATACCTA | ATGGTTTTAA | TAGGGCGGAA | TTTGGAGTTA | GACCGCCCCA | TCTTATGGAC | 900
| TTTATGAATT | CTTTGTTTGT | AACTGCAGAG | ACTGTTAGAA | GTCAAACTGT | GTGGGGAGGA | 960
| CACTTAGTTA | GTTCACGAAA | TACGGCTGGT | AACCGTATAA | ATTTCCCTAG | TTACGGGGTC | 1020
| TTCAATCCTG | GTGGCGCCAT | TTGGATTGCA | GATGAGGATC | CACGTCCTTT | TATCGGACA | 1080
| TTATCAGATC | CTGTTTTTGT | CCGAGGAGGA | TTTGGGAATC | CTCATTATGT | ACTGGGGCTT | 1140
| AGGGGAGTAG | CATTTCAACA | AACTGGTACG | AACCACACCC | GAACATTTAG | AAATAGTGGG | 1200
| ACCATAGATT | CTCTAGATGA | AATCCCACCT | CAGGATAATA | GTGGGGCACC | TTGGAATGAT | 1260
| TATAGTCATG | TATTAAATCA | TGTTACATTT | GTACGATGGC | CAGGTGAGAT | TCAGGAAGT | 1320
| GATTCATGGA | GAGCTCCAAT | GTTTTCTTGG | ACGCACCGTA | GTGCAACCCC | TACAAATACA | 1380
| ATTGATCCGG | AGAGGATTAC | TCAAATACCA | TTGGTAAAAG | CACATACACT | TCAGTCAGGT | 1440
| ACTACTGTTG | TAAGAGGGCC | CGGGTTTACG | GGAGGAGATA | TTCTTCGACG | AACAAGTGGA | 1500
| GGACCATTTG | CTTATACTAT | TGTTAATATA | AATGGGCAAT | TACCCCAAAG | GTATCGTGCA | 1560
| AGAATACGCT | ATGCCTCTAC | TACAAATCTA | AGAATTTACG | TAACGGTTGC | AGGTGAACGG | 1620
| ATTTTTGCTG | GTCAATTTAA | CAAAACAATG | GATACCGGTG | ACCCATTAAC | ATTCCAATCT | 1680
| TTTAGTTACG | CAACTATTAA | TACAGCTTTT | ACATTCCCAA | TGAGCCAGAG | TAGTTTCACA | 1740
| GTAGGTGCTG | ATACTTTTAG | TTCAGGGAAT | GAAGTTTATA | TAGACAGATT | TGAATTGATT | 1800
| CCAGTTACTG | CAACATTTGA | AGCAGAATAT | GATTTAGAAA | GAGCACAAAA | GGCGGTGAAT | 1860
| GCGCTGTTTA | CTTCTATAAA | CCAAATAGGG | ATAAAAACAG | ATGTGACGGA | TTATCATATC | 1920
| GATCGAGTAT | CCAATTTAGT | TGAGTGTTTA | TCTGATGAAT | TTTGTCTGGA | TGAAAAAAAA | 1980
| GAATTGTCCG | AGAAAGTCAA | ACATGCGAAG | CGACTTAGTG | ATGAGCGGAA | TTTACTTCAA | 2040
| GATCCAAACT | TTAGAGGGAT | CAATAGACAA | CTAGACCGTG | GCTGGAGAGG | AAGTACGGAT | 2100
| ATTACCATCC | AAGGAGGCGA | TGACGTATTC | AAAGAGAATT | ACGTTACGCT | ATTGGGTACC | 2160
| TTTGATGAGT | GCTATCCAAC | GTATTTATAT | CAAAAAATAG | ATGAGTCGAA | ATTAAAAGCC | 2220
| TATACCCGTT | ACCAATTAAG | AGGGTATATC | GAAGATAGTC | AAGACTTAGA | AATCTATTTA | 2280
| ATTCGCTACA | ATGCCAAACA | CGAAACAGTA | AATGTGCCAG | GTACGGGTTC | CTTATGGCCG | 2340
| CTTTCAGCCC | CAAGTCCAAT | CGGAAAATGT | GCCCATCATT | CCCATCATTT | CTCCTTGGAC | 2400

-continued

| | | | | | |
|---|---|---|---|---|---|
| ATTGATGTTG | GATGTACAGA | CTTAAATGAG | GACTTAGGTG | TATGGGTGAT | ATTCAAGATT | 2460
| AAGACGCAAG | ATGGCCATGC | AAGACTAGGA | AATCTAGAAT | TTCTCGAAGA | GAAACCATTA | 2520
| GTAGGAGAAG | CACTAGCTCG | TGTGAAAAGA | GCGGAGAAAA | AATGGAGAGA | CAAACGTGAA | 2580
| AAATTGGAAT | GGGAAACAAA | TATTGTTTAT | AAAGAGGCAA | AAGAATCTGT | AGATGCTTTA | 2640
| TTTGTAAACT | CTCAATATGA | TAGATTACAA | GCGGATACCA | ACATCGCGAT | GATTCATGCG | 2700
| GCAGATAAAC | GCGTTCATAG | CATTCGAGAA | GCTTATCTGC | CTGAGCTGTC | TGTGATTCCG | 2760
| GGTGTCAATG | CGGCTATTTT | TGAAGAATTA | GAAGGGCGTA | TTTTCACTGC | ATTCTCCCTA | 2820
| TATGATGCGA | GAAATGTCAT | TAAAAATGGT | GATTTTAATA | ATGGCTTATC | CTGCTGGAAC | 2880
| GTGAAAGGGC | ATGTAGATGT | AGAAGAACAA | AACAACCACC | GTTCGGTCCT | TGTTGTTCCG | 2940
| GAATGGGAAG | CAGAAGTGTC | ACAAGAAGTT | CGTGTCTGTC | CGGGTCGTGG | CTATATCCTT | 3000
| CGTGTCACAG | CGTACAAGGA | GGGATATGGA | GAAGGTTGCG | TAACCATTCA | TGAGATCGAG | 3060
| AACAATACAG | ACGAACTGAA | GTTTAGCAAC | TGTGTAGAAG | AGGAAGTATA | TCCAAACAAC | 3120
| ACGGTAACGT | GTAATGATTA | TACTGCGACT | CAAGAAGAAT | ATGAGGGTAC | GTACACTTCT | 3180
| CGTAATCGAG | GATATGACGG | AGCCTATGAA | AGCAATTCTT | CTGTACCAGC | TGATTATGCA | 3240
| TCAGCCTATG | AAGAAAAAGC | ATATACAGAT | GGACGAAGAG | ACAATCCTTG | TGAATCTAAC | 3300
| AGAGGATATG | GGGATTACAC | ACCACTACCA | GCTGGCTATG | TGACAAAAGA | ATTAGAGTAC | 3360
| TTCCCAGAAA | CCGATAAGGT | ATGGATTGAG | ATCGGAGAAA | CGGAAGGAAC | ATTCATCGTG | 3420
| GACAGCGTGG | AATTACTTCT | TATGGAGGAA | | | | 3450

( 2 ) INFORMATION FOR SEQ ID NO:21:

( i ) SEQUENCE CHARACTERISTICS:
        ( A ) LENGTH: 1150 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:21:

```
Met Asp Asn Asn Pro Asn Ile Asn Glu Cys Ile Pro Tyr Asn Cys Leu
 1               5                  10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Leu Asn Asn Ala Gln Leu Arg Glu
        115                 120                 125

Asp Val Arg Ile Arg Phe Ala Asn Thr Asp Asp Ala Leu Ile Thr Ala
    130                 135                 140

Ile Asn Asn Phe Thr Leu Thr Ser Phe Glu Ile Pro Leu Leu Ser Val
145                 150                 155                 160

Tyr Val Gln Ala Ala Asn Leu His Leu Ser Leu Leu Arg Asp Ala Val
```

```
                              165                      170                        175
Ser  Phe  Gly  Gln  Gly  Trp  Gly  Leu  Asp  Ile  Ala  Thr  Val  Asn  Asn  His
               180                      185                      190

Tyr  Asn  Arg  Leu  Ile  Asn  Leu  Ile  His  Arg  Tyr  Thr  Lys  His  Cys  Leu
               195                      200                      205

Asp  Thr  Tyr  Asn  Gln  Gly  Leu  Glu  Asn  Leu  Arg  Gly  Thr  Asn  Thr  Arg
     210                           215                      220

Gln  Trp  Ala  Arg  Phe  Asn  Gln  Phe  Arg  Arg  Asp  Leu  Thr  Leu  Thr  Val
225                      230                      235                           240

Leu  Asp  Ile  Val  Ala  Leu  Phe  Pro  Asn  Tyr  Asp  Val  Arg  Thr  Tyr  Pro
                    245                      250                      255

Ile  Gln  Thr  Ser  Ser  Gln  Leu  Thr  Arg  Glu  Ile  Tyr  Thr  Ser  Ser  Val
               260                      265                      270

Ile  Glu  Asp  Ser  Pro  Val  Ser  Ala  Asn  Ile  Pro  Asn  Gly  Phe  Asn  Arg
          275                      280                      285

Ala  Glu  Phe  Gly  Val  Arg  Pro  Pro  His  Leu  Met  Asp  Phe  Met  Asn  Ser
     290                      295                      300

Leu  Phe  Val  Thr  Ala  Glu  Thr  Val  Arg  Ser  Gln  Thr  Val  Trp  Gly  Gly
305                      310                      315                           320

His  Leu  Val  Ser  Ser  Arg  Asn  Thr  Ala  Gly  Asn  Arg  Ile  Asn  Phe  Pro
                    325                      330                      335

Ser  Tyr  Gly  Val  Phe  Asn  Pro  Gly  Gly  Ala  Ile  Trp  Ile  Ala  Asp  Glu
               340                      345                      350

Asp  Pro  Arg  Pro  Phe  Tyr  Arg  Thr  Leu  Ser  Asp  Pro  Val  Phe  Val  Arg
          355                      360                      365

Gly  Gly  Phe  Gly  Asn  Pro  His  Tyr  Val  Leu  Gly  Leu  Arg  Gly  Val  Ala
     370                      375                      380

Phe  Gln  Gln  Thr  Gly  Thr  Asn  His  Thr  Arg  Thr  Phe  Arg  Asn  Ser  Gly
385                      390                      395                           400

Thr  Ile  Asp  Ser  Leu  Asp  Glu  Ile  Pro  Pro  Gln  Asp  Asn  Ser  Gly  Ala
                    405                      410                      415

Pro  Trp  Asn  Asp  Tyr  Ser  His  Val  Leu  Asn  His  Val  Thr  Phe  Val  Arg
                    420                      425                      430

Trp  Pro  Gly  Glu  Ile  Ser  Gly  Ser  Asp  Ser  Trp  Arg  Ala  Pro  Met  Phe
               435                      440                      445

Ser  Trp  Thr  His  Arg  Ser  Ala  Thr  Pro  Thr  Asn  Thr  Ile  Asp  Pro  Glu
     450                      455                      460

Arg  Ile  Thr  Gln  Ile  Pro  Leu  Val  Lys  Ala  His  Thr  Leu  Gln  Ser  Gly
465                      470                      475                           480

Thr  Thr  Val  Val  Arg  Gly  Pro  Gly  Phe  Thr  Gly  Gly  Asp  Ile  Leu  Arg
                    485                      490                      495

Arg  Thr  Ser  Gly  Gly  Pro  Phe  Ala  Tyr  Thr  Ile  Val  Asn  Ile  Asn  Gly
               500                      505                      510

Gln  Leu  Pro  Gln  Arg  Tyr  Arg  Ala  Arg  Ile  Arg  Tyr  Ala  Ser  Thr  Thr
               515                      520                      525

Asn  Leu  Arg  Ile  Tyr  Val  Thr  Val  Ala  Gly  Glu  Arg  Ile  Phe  Ala  Gly
     530                      535                      540

Gln  Phe  Asn  Lys  Thr  Met  Asp  Thr  Gly  Asp  Pro  Leu  Thr  Phe  Gln  Ser
545                      550                      555                           560

Phe  Ser  Tyr  Ala  Thr  Ile  Asn  Thr  Ala  Phe  Thr  Phe  Pro  Met  Ser  Gln
                    565                      570                      575

Ser  Ser  Phe  Thr  Val  Gly  Ala  Asp  Thr  Phe  Ser  Ser  Gly  Asn  Glu  Val
               580                      585                      590
```

```
Tyr Ile Asp Arg Phe Glu Leu Ile Pro Val Thr Ala Thr Phe Glu Ala
            595                 600                 605

Glu Tyr Asp Leu Glu Arg Ala Gln Lys Ala Val Asn Ala Leu Phe Thr
            610                 615                 620

Ser Ile Asn Gln Ile Gly Ile Lys Thr Asp Thr Asp Tyr His Ile
625                 630                 635                 640

Asp Arg Val Ser Asn Leu Val Glu Cys Leu Ser Asp Glu Phe Cys Leu
                645                 650                 655

Asp Glu Lys Lys Glu Leu Ser Glu Lys Val Lys His Ala Lys Arg Leu
            660                 665                 670

Ser Asp Glu Arg Asn Leu Leu Gln Asp Pro Asn Phe Arg Gly Ile Asn
            675                 680                 685

Arg Gln Leu Asp Arg Gly Trp Arg Gly Ser Thr Asp Ile Thr Ile Gln
            690                 695                 700

Gly Gly Asp Asp Val Phe Lys Glu Asn Tyr Val Thr Leu Leu Gly Thr
705                 710                 715                 720

Phe Asp Glu Cys Tyr Pro Thr Tyr Leu Tyr Gln Lys Ile Asp Glu Ser
                725                 730                 735

Lys Leu Lys Ala Tyr Thr Arg Tyr Gln Leu Arg Gly Tyr Ile Glu Asp
            740                 745                 750

Ser Gln Asp Leu Glu Ile Tyr Leu Ile Arg Tyr Asn Ala Lys His Glu
            755                 760                 765

Thr Val Asn Val Pro Gly Thr Gly Ser Leu Trp Pro Leu Ser Ala Pro
770                 775                 780

Ser Pro Ile Gly Lys Cys Ala His His Ser His His Phe Ser Leu Asp
785                 790                 795                 800

Ile Asp Val Gly Cys Thr Asp Leu Asn Glu Asp Leu Gly Val Trp Val
                805                 810                 815

Ile Phe Lys Ile Lys Thr Gln Asp Gly His Ala Arg Leu Gly Asn Leu
            820                 825                 830

Glu Phe Leu Glu Glu Lys Pro Leu Val Gly Glu Ala Leu Ala Arg Val
            835                 840                 845

Lys Arg Ala Glu Lys Lys Trp Arg Asp Lys Arg Glu Lys Leu Glu Trp
            850                 855                 860

Glu Thr Asn Ile Val Tyr Lys Glu Ala Lys Glu Ser Val Asp Ala Leu
865                 870                 875                 880

Phe Val Asn Ser Gln Tyr Asp Arg Leu Gln Ala Asp Thr Asn Ile Ala
                885                 890                 895

Met Ile His Ala Ala Asp Lys Arg Val His Ser Ile Arg Glu Ala Tyr
            900                 905                 910

Leu Pro Glu Leu Ser Val Ile Pro Gly Val Asn Ala Ala Ile Phe Glu
            915                 920                 925

Glu Leu Glu Gly Arg Ile Phe Thr Ala Phe Ser Leu Tyr Asp Ala Arg
930                 935                 940

Asn Val Ile Lys Asn Gly Asp Phe Asn Asn Gly Leu Ser Cys Trp Asn
945                 950                 955                 960

Val Lys Gly His Val Asp Val Glu Glu Gln Asn Asn His Arg Ser Val
                965                 970                 975

Leu Val Val Pro Glu Trp Glu Ala Glu Val Ser Gln Glu Val Arg Val
            980                 985                 990

Cys Pro Gly Arg Gly Tyr Ile Leu Arg Val Thr Ala Tyr Lys Glu Gly
            995                 1000                1005

Tyr Gly Glu Gly Cys Val Thr Ile His Glu Ile Glu Asn Asn Thr Asp
1010                1015                1020
```

|     |     |     |     |     |     |     |     |     |     |     |     |     |     |     |
| --- | --- | --- | --- | --- | --- | --- | --- | --- | --- | --- | --- | --- | --- | --- |
| Glu | Leu | Lys | Phe | Ser | Asn | Cys | Val | Glu | Glu | Val | Tyr | Pro | Asn | Asn |
| 1025 |     |     |     | 1030 |     |     |     | 1035 |     |     |     | 1040 |     |     |
| Thr | Val | Thr | Cys | Asn | Asp | Tyr | Thr | Ala | Thr | Gln | Glu | Glu | Tyr | Glu | Gly |
|     |     |     | 1045 |     |     |     | 1050 |     |     |     |     | 1055 |     |     |
| Thr | Tyr | Thr | Ser | Arg | Asn | Arg | Gly | Tyr | Asp | Gly | Ala | Tyr | Glu | Ser | Asn |
|     |     |     | 1060 |     |     |     | 1065 |     |     |     | 1070 |     |     |     |
| Ser | Ser | Val | Pro | Ala | Asp | Tyr | Ala | Ser | Ala | Tyr | Glu | Glu | Lys | Ala | Tyr |
|     |     | 1075 |     |     |     | 1080 |     |     |     |     | 1085 |     |     |     |
| Thr | Asp | Gly | Arg | Arg | Asp | Asn | Pro | Cys | Glu | Ser | Asn | Arg | Gly | Tyr | Gly |
|     | 1090 |     |     |     |     | 1095 |     |     |     | 1100 |     |     |     |     |
| Asp | Tyr | Thr | Pro | Leu | Pro | Ala | Gly | Tyr | Val | Thr | Lys | Glu | Leu | Glu | Tyr |
| 1105 |     |     |     | 1110 |     |     |     | 1115 |     |     |     | 1120 |     |     |
| Phe | Pro | Glu | Thr | Asp | Lys | Val | Trp | Ile | Glu | Ile | Gly | Glu | Thr | Glu | Gly |
|     |     |     | 1125 |     |     |     | 1130 |     |     |     |     | 1135 |     |     |
| Thr | Phe | Ile | Val | Asp | Ser | Val | Glu | Leu | Leu | Leu | Met | Glu | Glu |     |     |
|     |     |     | 1140 |     |     |     | 1145 |     |     |     | 1150 |     |     |     |

(2) INFORMATION FOR SEQ ID NO:22:

(i) SEQUENCE CHARACTERISTICS:
        (A) LENGTH: 3444 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

```
ATGGAGAATA ATATTCAAAA TCAATGCGTA CCTTACAATT GTTTAAATAA TCCTGAAGTA        60
GAAATATTAA ATGAAGAAAG AAGTACTGGC AGATTACCGT TAGATATATC CTTATCGCTT       120
ACACGTTTCC TTTTGAGTGA ATTTGTTCCA GGTGTGGGAG TTGCGTTTGG ATTATTTGAT       180
TTAATATGGG GTTTTATAAC TCCTTCTGAT GGAGCTTAT  TTCTTTTACA GATTGAACAA       240
TTGATTGAGC AAAGAATAGA AACATTGGAA AGGAACCGGG CAATTACTAC ATTACGAGGG       300
TTAGCAGATA GCTATGAAAT TTATATTGAA GCACTAAGAG AGTGGGAAGC AAATCCTAAT       360
AATGCACAAT TAAGGGAAGA TGTGCGTATT CGATTGCTA  ATACAGACGA CGCTTTAATA       420
ACAGCAATAA ATAATTTTAC ACTTACAAGT TTTGAAATCC CTCTTTTATC GGTCTATGTT       480
CAAGCGGCGA ATTTACATTT ATCACTATTA AGAGACGCTG TATCGTTTGG GCAGGGTTGG       540
GGACTGGATA TAGCTACTGT TAATAATCAT TATAATAGAT TAATAAATCT TATTCATAGA       600
TATACGAAAC ATTGTTTGGA CACATACAAT CAAGGATTAG AAAACTTAAG AGGTACTAAT       660
ACTCGACAAT GGGCAAGATT CAATCAGTTT AGGAGAGATT TAACACTTAC TGTATTAGAT       720
ATCGTTGCTC TTTTTCCGAA CTACGATGTT AGAACATATC CAATTCAAAC GTCATCCAA        780
TTAACAAGGG AAATTTATAC AAGTTCAGTA ATTGAGGATT CTCCAGTTTC TGCTAATATA       840
CCTAATGGTT TAATAGGGC  GGAATTTGGA GTTAGACCGC CCATCTTAT  GGACTTTATG       900
AATTCTTTGT TTGTAACTGC AGAGACTGTT AGAAGTCAAA CTGTGTGGGG AGGACACTTA       960
GTTAGTTCAC GAAATACGGC TGGTAACCGT ATAAATTTCC CTAGTTACGG GGTCTTCAAT      1020
CCTGGTGGCG CCATTTGGAT TGCAGATGAG GATCCACGTC CTTTTTATCG GACATTATCA      1080
GATCCTGTTT TTGTCCGAGG AGGATTTGGG AATCCTCATT ATGTACTGGG GCTTAGGGGA      1140
GTAGCATTTC AACAAACTGG TACGAACCAC ACCCGAACAT TTAGAAATAG TGGGACCATA      1200
GATTCTCTAG ATGAAATCCC ACCTCAGGAT AATAGTGGGG CACCTTGGAA TGATTATAGT      1260
```

| | | | | | | |
|---|---|---|---|---|---|---|
| CATGTATTAA | ATCATGTTAC | ATTTGTACGA | TGGCCAGGTG | AGATTTCAGG | AAGTGATTCA | 1320 |
| TGGAGAGCTC | CAATGTTTTC | TTGGACGCAC | CGTAGTGCAA | CCCCTACAAA | TACAATTGAT | 1380 |
| CCGGAGAGGA | TTACTCAAAT | ACCATTGGTA | AAAGCACATA | CACTTCAGTC | AGGTACTACT | 1440 |
| GTTGTAAGAG | GGCCCGGGTT | TACGGGAGGA | GATATTCTTC | GACGAACAAG | TGGAGGACCA | 1500 |
| TTTGCTTATA | CTATTGTTAA | TATAAATGGG | CAATTACCCC | AAAGGTATCG | TGCAAGAATA | 1560 |
| CGCTATGCCT | CTACTACAAA | TCTAAGAATT | TACGTAACGG | TTGCAGGTGA | ACGGATTTTT | 1620 |
| GCTGGTCAAT | TTAACAAAAC | AATGGATACC | GGTGACCCAT | TAACATTCCA | ATCTTTTAGT | 1680 |
| TACGCAACTA | TTAATACAGC | TTTTACATTC | CCAATGAGCC | AGAGTAGTTT | CACAGTAGGT | 1740 |
| GCTGATACTT | TTAGTTCAGG | GAATGAAGTT | TATATAGACA | GATTTGAATT | GATTCCAGTT | 1800 |
| ACTGCAACAT | TTGAAGCAGA | ATATGATTTA | GAAAGAGCAC | AAAAGGCGGT | GAATGCGCTG | 1860 |
| TTTACTTCTA | TAAACCAAAT | AGGGATAAAA | ACAGATGTGA | CGGATTATCA | TATCGATCGA | 1920 |
| GTATCCAATT | TAGTTGAGTG | TTTATCTGAT | GAATTTTGTC | TGGATGAAAA | AAAAGAATTG | 1980 |
| TCCGAGAAAG | TCAAACATGC | GAAGCGACTT | AGTGATGAGC | GGAATTTACT | TCAAGATCCA | 2040 |
| AACTTTAGAG | GGATCAATAG | ACAACTAGAC | CGTGGCTGGA | GAGGAAGTAC | GGATATTACC | 2100 |
| ATCCAAGGAG | GCGATGACGT | ATTCAAAGAG | AATTACGTTA | CGCTATTGGG | TACCTTTGAT | 2160 |
| GAGTGCTATC | CAACGTATTT | ATATCAAAAA | ATAGATGAGT | CGAAATTAAA | AGCCTATACC | 2220 |
| CGTTACCAAT | TAAGAGGGTA | TATCGAAGAT | AGTCAAGACT | TAGAAATCTA | TTTAATTCGC | 2280 |
| TACAATGCCA | AACACGAAAC | AGTAAATGTG | CCAGGTACGG | GTTCCTTATG | GCCGCTTTCA | 2340 |
| GCCCCAAGTC | CAATCGGAAA | ATGTGCCCAT | CATTCCATC | ATTTCTCCTT | GGACATTGAT | 2400 |
| GTTGGATGTA | CAGACTTAAA | TGAGGACTTA | GGTGTATGGG | TGATATTCAA | GATTAAGACG | 2460 |
| CAAGATGGCC | ATGCAAGACT | AGGAAATCTA | GAATTTCTCG | AAGAGAAACC | ATTAGTAGGA | 2520 |
| GAAGCACTAG | CTCGTGTGAA | AAGAGCGGAG | AAAAAATGGA | GAGACAAACG | TGAAAAATTG | 2580 |
| GAATGGGAAA | CAAATATTGT | TTATAAAGAG | GCAAAAGAAT | CTGTAGATGC | TTTATTTGTA | 2640 |
| AACTCTCAAT | ATGATAGATT | ACAAGCGGAT | ACCAACATCG | CGATGATTCA | TGCGGCAGAT | 2700 |
| AAACGCGTTC | ATAGCATTCG | AGAAGCTTAT | CTGCCTGAGC | TGTCTGTGAT | TCCGGGTGTC | 2760 |
| AATGCGGCTA | TTTTTGAAGA | ATTAGAAGGG | CGTATTTTCA | CTGCATTCTC | CCTATATGAT | 2820 |
| GCGAGAAATG | TCATTAAAAA | TGGTGATTTT | AATAATGGCT | TATCCTGCTG | GAACGTGAAA | 2880 |
| GGGCATGTAG | ATGTAGAAGA | ACAAAACAAC | CACCGTTCGG | TCCTTGTTGT | TCCGGAATGG | 2940 |
| GAAGCAGAAG | TGTCACAAGA | AGTTCGTGTC | TGTCCGGGTC | GTGGCTATAT | CCTTCGTGTC | 3000 |
| ACAGCGTACA | AGGAGGGATA | TGGAGAAGGT | TGCGTAACCA | TTCATGAGAT | CGAGAACAAT | 3060 |
| ACAGACGAAC | TGAAGTTTAG | CAACTGTGTA | GAAGAGGAAG | TATATCCAAA | CAACACGGTA | 3120 |
| ACGTGTAATG | ATTATACTGC | GACTCAAGAA | GAATATGAGG | GTACGTACAC | TTCTCGTAAT | 3180 |
| CGAGGATATG | ACGGAGCCTA | TGAAAGCAAT | TCTTCTGTAC | CAGCTGATTA | TGCATCAGCC | 3240 |
| TATGAAGAAA | AAGCATATAC | AGATGGACGA | AGAGACAATC | CTTGTGAATC | TAACAGAGGA | 3300 |
| TATGGGGATT | ACACACCACT | ACCAGCTGGC | TATGTGACAA | AAGAATTAGA | GTACTTCCCA | 3360 |
| GAAACCGATA | AGGTATGGAT | TGAGATCGGA | GAAACGGAAG | GAACATTCAT | CGTGGACAGC | 3420 |
| GTGGAATTAC | TTCTTATGGA | GGAA | | | | 3444 |

( 2 ) INFORMATION FOR SEQ ID NO:23:

( i ) SEQUENCE CHARACTERISTICS:
        ( A ) LENGTH: 1148 amino acids
        ( B ) TYPE: amino acid (C) STRANDEDNESS: single
(D) TOPOLOGY: linear (ii) MOLECULE TYPE: protein (xi) SEQUENCE DESCRIPTION: SEQ ID NO:23:

| Met | Glu | Asn | Asn | Ile | Gln | Asn | Gln | Cys | Val | Pro | Tyr | Asn | Cys | Leu | Asn |
|---|---|---|---|---|---|---|---|---|---|---|---|---|---|---|---|
| 1 | | | | 5 | | | | | 10 | | | | | 15 | |
| Asn | Pro | Glu | Val | Glu | Ile | Leu | Asn | Glu | Glu | Arg | Ser | Thr | Gly | Arg | Leu |
| | | | 20 | | | | | 25 | | | | | 30 | | |
| Pro | Leu | Asp | Ile | Ser | Leu | Ser | Leu | Thr | Arg | Phe | Leu | Leu | Ser | Glu | Phe |
| | | | 35 | | | | 40 | | | | | 45 | | | |
| Val | Pro | Gly | Val | Gly | Val | Ala | Phe | Gly | Leu | Phe | Asp | Leu | Ile | Trp | Gly |
| | | | 50 | | | | 55 | | | | | 60 | | | |
| Phe | Ile | Thr | Pro | Ser | Asp | Trp | Ser | Leu | Phe | Leu | Leu | Gln | Ile | Glu | Gln |
| 65 | | | | | 70 | | | | | 75 | | | | | 80 |
| Leu | Ile | Glu | Gln | Arg | Ile | Glu | Thr | Leu | Glu | Arg | Asn | Arg | Ala | Ile | Thr |
| | | | | 85 | | | | | 90 | | | | | 95 | |
| Thr | Leu | Arg | Gly | Leu | Ala | Asp | Ser | Tyr | Glu | Ile | Tyr | Ile | Glu | Ala | Leu |
| | | | 100 | | | | | 105 | | | | | 110 | | |
| Arg | Glu | Trp | Glu | Ala | Asn | Pro | Asn | Asn | Ala | Gln | Leu | Arg | Glu | Asp | Val |
| | | | 115 | | | | | 120 | | | | | 125 | | |
| Arg | Ile | Arg | Phe | Ala | Asn | Thr | Asp | Asp | Ala | Leu | Ile | Thr | Ala | Ile | Asn |
| | | | 130 | | | | | 135 | | | | | 140 | | |
| Asn | Phe | Thr | Leu | Thr | Ser | Phe | Glu | Ile | Pro | Leu | Leu | Ser | Val | Tyr | Val |
| 145 | | | | | 150 | | | | | 155 | | | | | 160 |
| Gln | Ala | Ala | Asn | Leu | His | Leu | Ser | Leu | Leu | Arg | Asp | Ala | Val | Ser | Phe |
| | | | | 165 | | | | | 170 | | | | | 175 | |
| Gly | Gln | Gly | Trp | Gly | Leu | Asp | Ile | Ala | Thr | Val | Asn | Asn | His | Tyr | Asn |
| | | | 180 | | | | | 185 | | | | | 190 | | |
| Arg | Leu | Ile | Asn | Leu | Ile | His | Arg | Tyr | Thr | Lys | His | Cys | Leu | Asp | Thr |
| | | | 195 | | | | | 200 | | | | | 205 | | |
| Tyr | Asn | Gln | Gly | Leu | Glu | Asn | Leu | Arg | Gly | Thr | Asn | Thr | Arg | Gln | Trp |
| | 210 | | | | | 215 | | | | | 220 | | | | |
| Ala | Arg | Phe | Asn | Gln | Phe | Arg | Arg | Asp | Leu | Thr | Leu | Thr | Val | Leu | Asp |
| 225 | | | | 230 | | | | | 235 | | | | | | 240 |
| Ile | Val | Ala | Leu | Phe | Pro | Asn | Tyr | Asp | Val | Arg | Thr | Tyr | Pro | Ile | Gln |
| | | | | 245 | | | | | 250 | | | | | 255 | |
| Thr | Ser | Ser | Gln | Leu | Thr | Arg | Glu | Ile | Tyr | Thr | Ser | Ser | Val | Ile | Glu |
| | | | 260 | | | | | 265 | | | | | 270 | | |
| Asp | Ser | Pro | Val | Ser | Ala | Asn | Ile | Pro | Asn | Gly | Phe | Asn | Arg | Ala | Glu |
| | | | 275 | | | | 280 | | | | | 285 | | | |
| Phe | Gly | Val | Arg | Pro | Pro | His | Leu | Met | Asp | Phe | Met | Asn | Ser | Leu | Phe |
| | 290 | | | | | 295 | | | | | 300 | | | | |
| Val | Thr | Ala | Glu | Thr | Val | Arg | Ser | Gln | Thr | Val | Trp | Gly | Gly | His | Leu |
| 305 | | | | | 310 | | | | | 315 | | | | | 320 |
| Val | Ser | Ser | Arg | Asn | Thr | Ala | Gly | Asn | Arg | Ile | Asn | Phe | Pro | Ser | Tyr |
| | | | | 325 | | | | | 330 | | | | | 335 | |
| Gly | Val | Phe | Asn | Pro | Gly | Gly | Ala | Ile | Trp | Ile | Ala | Asp | Glu | Asp | Pro |
| | | | 340 | | | | | 345 | | | | | 350 | | |
| Arg | Pro | Phe | Tyr | Arg | Thr | Leu | Ser | Asp | Pro | Val | Phe | Val | Arg | Gly | Gly |
| | | 355 | | | | | 360 | | | | | 365 | | | |
| Phe | Gly | Asn | Pro | His | Tyr | Val | Leu | Gly | Leu | Arg | Gly | Val | Ala | Phe | Gln |
| | | 370 | | | | | 375 | | | | | 380 | | | |
| Gln | Thr | Gly | Thr | Asn | His | Thr | Arg | Thr | Phe | Arg | Asn | Ser | Gly | Thr | Ile |

```
              385                    390                    395                    400

Asp  Ser  Leu  Asp  Glu  Ile  Pro  Pro  Gln  Asn  Ser  Gly  Ala  Pro  Trp
                           405                 410                      415

Asn  Asp  Tyr  Ser  His  Val  Leu  Asn  His  Val  Thr  Phe  Val  Arg  Trp  Pro
                      420                 425                      430

Gly  Glu  Ile  Ser  Gly  Ser  Asp  Ser  Trp  Arg  Ala  Pro  Met  Phe  Ser  Trp
                      435                 440                      445

Thr  His  Arg  Ser  Ala  Thr  Pro  Thr  Asn  Thr  Ile  Asp  Pro  Glu  Arg  Ile
            450                      455                      460

Thr  Gln  Ile  Pro  Leu  Val  Lys  Ala  His  Thr  Leu  Gln  Ser  Gly  Thr  Thr
       465                      470                      475                      480

Val  Val  Arg  Gly  Pro  Gly  Phe  Thr  Gly  Gly  Asp  Ile  Leu  Arg  Arg  Thr
                           485                      490                      495

Ser  Gly  Gly  Pro  Phe  Ala  Tyr  Thr  Ile  Val  Asn  Ile  Asn  Gly  Gln  Leu
                      500                 505                      510

Pro  Gln  Arg  Tyr  Arg  Ala  Arg  Ile  Arg  Tyr  Ala  Ser  Thr  Thr  Asn  Leu
                      515                      520                      525

Arg  Ile  Tyr  Val  Thr  Val  Ala  Gly  Glu  Arg  Ile  Phe  Ala  Gly  Gln  Phe
                 530                      535                      540

Asn  Lys  Thr  Met  Asp  Thr  Gly  Asp  Pro  Leu  Thr  Phe  Gln  Ser  Phe  Ser
       545                      550                      555                      560

Tyr  Ala  Thr  Ile  Asn  Thr  Ala  Phe  Thr  Phe  Pro  Met  Ser  Gln  Ser  Ser
                           565                 570                      575

Phe  Thr  Val  Gly  Ala  Asp  Thr  Phe  Ser  Ser  Gly  Asn  Glu  Val  Tyr  Ile
                      580                      585                      590

Asp  Arg  Phe  Glu  Leu  Ile  Pro  Val  Thr  Ala  Thr  Phe  Glu  Ala  Glu  Tyr
                 595                      600                      605

Asp  Leu  Glu  Arg  Ala  Gln  Lys  Ala  Val  Asn  Ala  Leu  Phe  Thr  Ser  Ile
       610                      615                      620

Asn  Gln  Ile  Gly  Ile  Lys  Thr  Asp  Val  Thr  Asp  Tyr  His  Ile  Asp  Arg
       625                      630                      635                      640

Val  Ser  Asn  Leu  Val  Glu  Cys  Leu  Ser  Asp  Glu  Phe  Cys  Leu  Asp  Glu
                           645                      650                      655

Lys  Lys  Glu  Leu  Ser  Glu  Lys  Val  Lys  His  Ala  Lys  Arg  Leu  Ser  Asp
                      660                      665                      670

Glu  Arg  Asn  Leu  Leu  Gln  Asp  Pro  Asn  Phe  Arg  Gly  Ile  Asn  Arg  Gln
                      675                      680                      685

Leu  Asp  Arg  Gly  Trp  Arg  Gly  Ser  Thr  Asp  Ile  Thr  Ile  Gln  Gly  Gly
            690                      695                      700

Asp  Asp  Val  Phe  Lys  Glu  Asn  Tyr  Val  Thr  Leu  Leu  Gly  Thr  Phe  Asp
       705                      710                      715                      720

Glu  Cys  Tyr  Pro  Thr  Tyr  Leu  Tyr  Gln  Lys  Ile  Asp  Glu  Ser  Lys  Leu
                           725                      730                      735

Lys  Ala  Tyr  Thr  Arg  Tyr  Gln  Leu  Arg  Gly  Tyr  Ile  Glu  Asp  Ser  Gln
                      740                      745                      750

Asp  Leu  Glu  Ile  Tyr  Leu  Ile  Arg  Tyr  Asn  Ala  Lys  His  Glu  Thr  Val
            755                      760                      765

Asn  Val  Pro  Gly  Thr  Gly  Ser  Leu  Trp  Pro  Leu  Ser  Ala  Pro  Ser  Pro
       770                      775                      780

Ile  Gly  Lys  Cys  Ala  His  His  Ser  His  His  Phe  Ser  Leu  Asp  Ile  Asp
       785                      790                      795                      800

Val  Gly  Cys  Thr  Asp  Leu  Asn  Glu  Asp  Leu  Gly  Val  Trp  Val  Ile  Phe
                           805                      810                      815
```

| | | | | | | | | | | | | | | | |
|---|---|---|---|---|---|---|---|---|---|---|---|---|---|---|---|
|Lys|Ile|Lys|Thr 820|Gln|Asp|Gly|His|Ala 825|Arg|Leu|Gly|Asn|Leu 830|Glu|Phe|
|Leu|Glu|Glu 835|Lys|Pro|Leu|Val|Gly 840|Glu|Ala|Leu|Ala|Arg 845|Val|Lys|Arg|
|Ala|Glu 850|Lys|Lys|Trp|Arg|Asp 855|Lys|Arg|Glu|Lys|Leu 860|Glu|Trp|Glu|Thr|
|Asn 865|Ile|Val|Tyr|Lys|Glu 870|Ala|Lys|Glu|Ser|Val 875|Asp|Ala|Leu|Phe|Val 880|
|Asn|Ser|Gln|Tyr|Asp 885|Arg|Leu|Gln|Ala|Asp 890|Thr|Asn|Ile|Ala|Met 895|Ile|
|His|Ala|Ala|Asp 900|Lys|Arg|Val|His|Ser 905|Ile|Arg|Glu|Ala|Tyr 910|Leu|Pro|
|Glu|Leu|Ser 915|Val|Ile|Pro|Gly|Val 920|Asn|Ala|Ala|Ile|Phe 925|Glu|Glu|Leu|
|Glu|Gly 930|Arg|Ile|Phe|Thr|Ala 935|Phe|Ser|Leu|Tyr|Asp 940|Ala|Arg|Asn|Val|
|Ile 945|Lys|Asn|Gly|Asp|Phe 950|Asn|Asn|Gly|Leu|Ser 955|Cys|Trp|Asn|Val|Lys 960|
|Gly|His|Val|Asp|Val 965|Glu|Glu|Gln|Asn|Asn 970|His|Arg|Ser|Val|Leu 975|Val|
|Val|Pro|Glu|Trp 980|Glu|Ala|Glu|Val|Ser 985|Gln|Glu|Val|Arg|Val 990|Cys|Pro|
|Gly|Arg|Gly 995|Tyr|Ile|Leu|Arg|Val 1000|Thr|Ala|Tyr|Lys|Glu 1005|Gly|Tyr|Gly|
|Glu|Gly|Cys 1010|Val|Thr|Ile|His|Glu 1015|Ile|Glu|Asn|Asn|Thr 1020|Asp|Glu|Leu|
|Lys|Phe 1025|Ser|Asn|Cys|Val|Glu 1030|Glu|Glu|Val|Tyr|Pro 1035|Asn|Asn|Thr|Val 1040|
|Thr|Cys|Asn|Asp|Tyr 1045|Thr|Ala|Thr|Gln|Glu 1050|Glu|Tyr|Glu|Gly|Thr 1055|Tyr|
|Thr|Ser|Arg|Asn|Arg 1060|Gly|Tyr|Asp|Gly|Ala 1065|Tyr|Glu|Ser|Asn|Ser 1070|Ser|
|Val|Pro|Ala|Asp 1075|Tyr|Ala|Ser|Ala|Tyr 1080|Glu|Glu|Lys|Ala|Tyr 1085|Thr|Asp|
|Gly|Arg|Arg 1090|Asp|Asn|Pro|Cys|Glu 1095|Ser|Asn|Arg|Gly|Tyr 1100|Gly|Asp|Tyr|
|Thr|Pro 1105|Leu|Pro|Ala|Gly|Tyr 1110|Val|Thr|Lys|Glu|Leu 1115|Glu|Tyr|Phe|Pro 1120|
|Glu|Thr|Asp|Lys|Val 1125|Trp|Ile|Glu|Ile|Gly 1130|Glu|Thr|Glu|Gly|Thr 1135|Phe|
|Ile|Val|Asp|Ser|Val 1140|Glu|Leu|Leu|Leu|Met 1145|Glu|Glu| | | | |

( 2 ) INFORMATION FOR SEQ ID NO:24:

( i ) SEQUENCE CHARACTERISTICS:
        ( A ) LENGTH: 3522 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

```
ATGGAAAATA ATATTCAAAA TCAATGCGTA CCTTACAATT GTTTAAATAA TCCTGAAGTA        60
GAAATACTGA ACGAAGAACG CAGCACCGGC CGCCTGCCGC TGGACATCAG CCTGAGCCTT       120
```

| | | | | | | |
|---|---|---|---|---|---|---|
| ACACGTTTCC | TTTTGAGTGA | ATTTGTTCCA | GGTGTGGGAG | TTGCGTTTGG | ATTATTTGAT | 180 |
| TTAATATGGG | GTTTTATAAC | TCCTTCTGAT | TGGAGCTTAT | TTCTTTTACA | GATTGAACAA | 240 |
| TTGATTGAGC | AAAGAATAGA | AACATTGGAA | AGGAACCGGG | CAATTACTAC | ATTACGAGGG | 300 |
| TTAGCAGATA | GCTATGAAAT | TTATATTGAA | GCACTAAGAG | AGTGGGAAGC | AAATCCTAAT | 360 |
| AATGCACAAT | TAAGGGAAGA | TGTGCGTATT | CGATTGCTA | ATACAGACGA | CGCTTTAATA | 420 |
| ACAGCAATAA | ATAATTTTAC | ACTTACAAGT | TTTGAAATCC | CTCTTTTATC | GGTCTATGTT | 480 |
| CAAGCGGCGA | ATTTACATTT | ATCACTATTA | AGAGACGCTG | TATCGTTTGG | GCAGGGTTGG | 540 |
| GGACTGGATA | TAGCTACTGT | TAATAATCAT | TATAATAGAT | TAATAAATCT | TATTCATAGA | 600 |
| TATACGAAAC | ATTGTTTGGA | CACATACAAT | CAAGGATTAG | AAAACTTAAG | AGGTACTAAT | 660 |
| ACTCGACAAT | GGGCAAGATT | CAATCAGTTT | AGGAGAGATT | TAACACTTAC | TGTATTAGAT | 720 |
| ATCGTTGCTC | TTTTTCCGAA | CTACGATGTT | AGAACATATC | CAATTCAAAC | GTCATCCAA | 780 |
| TTAACAAGGG | AAATTTATAC | AAGTTCAGTA | ATTGAGGATT | CTCCAGTTTC | TGCTAATATA | 840 |
| CCTAATGGTT | TTAATAGGGC | GGAATTTGGA | GTTAGACCGC | CCATCTTAT | GGACTTTATG | 900 |
| AATTCTTTGT | TTGTAACTGC | AGAGACTGTT | AGAAGTCAAA | CTGTGTGGGG | AGGACACTTA | 960 |
| GTTAGTTCAC | GAAATACGGC | TGGTAACCGT | ATAAATTTCC | CTAGTTACGG | GGTCTTCAAT | 1020 |
| CCTGGTGGCG | CCATTTGGAT | TGCAGATGAG | GATCCACGTC | CTTTTTATCG | GACATTATCA | 1080 |
| GATCCTGTTT | TTGTCCGAGG | AGGATTTGGG | AATCCTCATT | ATGTACTGGG | GCTTAGGGGA | 1140 |
| GTAGCATTTC | AACAAACTGG | TACGAACCAC | ACCCGAACAT | TTAGAAATAG | TGGGACCATA | 1200 |
| GATTCTCTAG | ATGAAATCCC | ACCTCAGGAT | AATAGTGGGG | CACCTTGGAA | TGATTATAGT | 1260 |
| CATGTATTAA | ATCATGTTAC | ATTTGTACGA | TGGCCAGGTG | AGATTTCAGG | AAGTGATTCA | 1320 |
| TGGAGAGCTC | CAATGTTTTC | TTGGACGCAC | CGTAGTGCAA | CCCCTACAAA | TACAATTGAT | 1380 |
| CCGGAGAGGA | TTACTCAAAT | ACCATTGGTA | AAAGCACATA | CACTTCAGTC | AGGTACTACT | 1440 |
| GTTGTAAGAG | GGCCCGGGTT | TACGGGAGGA | GATATTCTTC | GACGAACAAG | TGGAGGACCA | 1500 |
| TTTGCTTATA | CTATTGTTAA | TATAAATGGG | CAATTACCCC | AAAGGTATCG | TGCAAGAATA | 1560 |
| CGCTATGCCT | CTACTACAAA | TCTAAGAATT | TACGTAACGG | TTGCAGGTGA | ACGGATTTTT | 1620 |
| GCTGGTCAAT | TTAACAAAAC | AATGGATACC | GGTGACCCAT | TAACATTCCA | ATCTTTTAGT | 1680 |
| TACGCAACTA | TTAATACAGC | TTTTACATTC | CCAATGAGCC | AGAGTAGTTT | CACAGTAGGT | 1740 |
| GCTGATACTT | TTAGTTCAGG | GAATGAAGTT | TATATAGACA | GATTTGAATT | GATTCCAGTT | 1800 |
| ACTGCAACAT | TTGAAGCAGA | ATATGATTTA | GAAAGAGCAC | AAAAGGCGGT | GAATGCGCTG | 1860 |
| TTTACTTCTA | TAAACCAAAT | AGGGATAAAA | ACAGATGTGA | CGGATTATCA | TATTGATCAA | 1920 |
| GTATCCAATT | TAGTGGATTG | TTTATCAGAT | GAATTTTGTC | TGGATGAAAA | GCGAGAATTG | 1980 |
| TCCGAGAAAG | TCAAACATGC | GAAGCGACTC | AGTGATGAGC | GGAATTTACT | TCAAGATCCA | 2040 |
| AACTTCAAAG | GCATCAATAG | GCAACTAGAC | CGTGGTTGGA | GAGGAAGTAC | GGATATTACC | 2100 |
| ATCCAAAGAG | GAGATGACGT | ATTCAAAGAA | AATTATGTCA | CACTACCAGG | TACCTTTGAT | 2160 |
| GAGTGCTATC | CAACGTATTT | ATATCAAAAA | ATAGATGAGT | CGAAATTAAA | ACCCTATACT | 2220 |
| CGTTATCAAT | TAAGAGGGTA | TATCGAGGAT | AGTCAAGACT | TAGAAATCTA | TTTGATCCGC | 2280 |
| TATAATGCAA | AACACGAAAC | AGTAAATGTG | CTAGGTACGG | GTTCTTTATG | GCCGCTTTCA | 2340 |
| GTCCAAAGTC | CAATCAGAAA | GTGTGGAGAA | CCGAATCGAT | GCGCGCCACA | CCTTGAATGG | 2400 |
| AATCCTGATC | TAGATTGTTC | CTGCAGAGAC | GGGGAAAAAT | GTGCACATCA | TTCGCATCAT | 2460 |
| TTCTCCTTGG | ACATTGATGT | TGGATGTACA | GACTTAAATG | AGGACTTAGA | TGTATGGGTG | 2520 |

| | | | | | | |
|---|---|---|---|---|---|---|
| ATATTCAAGA | TTAAGACGCA | AGATGGCCAT | GCAAGACTAG | GAAATCTAGA | GTTTCTCGAA | 2580 |
| GAGAAACCAT | TAGTCGGGGA | AGCACTAGCT | CGTGTGAAAA | GAGCAGAGAA | AAAATGGAGA | 2640 |
| GATAAACGTG | AAAAATTGGA | ATTGGAAACA | AATATTGTTT | ATAAAGAGGC | AAAAGAATCT | 2700 |
| GTAGATGCTT | TATTTGTAAA | CTCTCAATAT | GATCAATTAC | AAGCGGATAC | GAATATTGCC | 2760 |
| ATGATTCATG | CGGCAGATAA | ACGTGTTCAT | AGAATTCGGG | AAGCGTATCT | TCCAGAGTTA | 2820 |
| TCTGTGATTC | CGGGTGTAAA | TGTAGACATT | TTCGAAGAAT | TAAAAGGGCG | TATTTTCACT | 2880 |
| GCATTCTTCC | TATATGATGC | GAGAAATGTC | ATTAAAAACG | GTGATTTCAA | TAATGGCTTA | 2940 |
| TCATGCTGGA | ACGTGAAAGG | GCATGTAGAT | GTAGAAGAAC | AAAACAACCA | CCGTTCGGTC | 3000 |
| CTTGTTGTTC | CGGAATGGGA | AGCAGAAGTG | TCACAAGAAG | TTCGTGTCTG | TCCGGGTCGT | 3060 |
| GGCTATATCC | TTCGTGTCAC | AGCGTACAAG | GAGGGATATG | GAGAAGGTTG | CGTAACCATT | 3120 |
| CATGAGATCG | AGAACAATAC | AGACGAACTG | AAGTTTAGCA | ACTGCGTAGA | AGAGGAAGTC | 3180 |
| TATCCAAACA | ACACGGTAAC | GTGTAATGAT | TATACTGCAA | ATCAAGAAGA | ATACGGGGGT | 3240 |
| GCGTACACTT | CCCGTAATCG | TGGATATGAC | GAAACTTATG | GAAGCAATTC | TTCTGTACCA | 3300 |
| GCTGATTATG | CGTCAGTCTA | TGAAGAAAAA | TCGTATACAG | ATGGACGAAG | AGACAATCCT | 3360 |
| TGTGAATCTA | ACAGAGGATA | TGGGGATTAC | ACACCACTAC | CAGCTGGCTA | TGTGACAAAA | 3420 |
| GAATTAGAGT | ACTTCCCAGA | AACCGATAAG | GTATGGATTG | AGATCGGAGA | AACGGAAGGA | 3480 |
| ACATTCATCG | TGGACAGCGT | GGAATTACTC | CTTATGGAGG | AA | | 3522 |

( 2 ) INFORMATION FOR SEQ ID NO:25:

( i ) SEQUENCE CHARACTERISTICS:
        ( A ) LENGTH: 1174 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:25:

```
Met Glu Asn Asn Ile Gln Asn Gln Cys Val Pro Tyr Asn Cys Leu Asn
 1               5                  10                  15

Asn Pro Glu Val Glu Ile Leu Asn Glu Glu Arg Ser Thr Gly Arg Leu
                20                  25                  30

Pro Leu Asp Ile Ser Leu Ser Leu Thr Arg Phe Leu Leu Ser Glu Phe
            35                  40                  45

Val Pro Gly Val Gly Val Ala Phe Gly Leu Phe Asp Leu Ile Trp Gly
        50                  55                  60

Phe Ile Thr Pro Ser Asp Trp Ser Leu Phe Leu Leu Gln Ile Glu Gln
65                  70                  75                  80

Leu Ile Glu Gln Arg Ile Glu Thr Leu Glu Arg Asn Arg Ala Ile Thr
                85                  90                  95

Thr Leu Arg Gly Leu Ala Asp Ser Tyr Glu Ile Tyr Ile Glu Ala Leu
                100                 105                 110

Arg Glu Trp Glu Ala Asn Pro Asn Asn Ala Gln Leu Arg Glu Asp Val
            115                 120                 125

Arg Ile Arg Phe Ala Asn Thr Asp Asp Ala Leu Ile Thr Ala Ile Asn
130                 135                 140

Asn Phe Thr Leu Thr Ser Phe Glu Ile Pro Leu Leu Ser Val Tyr Val
145                 150                 155                 160

Gln Ala Ala Asn Leu His Leu Ser Leu Leu Arg Asp Ala Val Ser Phe
                165                 170                 175
```

```
Gly Gln Gly Trp Gly Leu Asp Ile Ala Thr Val Asn Asn His Tyr Asn
            180                 185                 190

Arg Leu Ile Asn Leu Ile His Arg Tyr Thr Lys His Cys Leu Asp Thr
        195                 200                 205

Tyr Asn Gln Gly Leu Glu Asn Leu Arg Gly Thr Thr Arg Gln Trp
    210                 215                 220

Ala Arg Phe Asn Gln Phe Arg Arg Asp Leu Thr Leu Thr Val Leu Asp
225                 230                 235                 240

Ile Val Ala Leu Phe Pro Asn Tyr Asp Val Arg Thr Tyr Pro Ile Gln
                245                 250                 255

Thr Ser Ser Gln Leu Thr Arg Glu Ile Tyr Thr Ser Ser Val Ile Glu
            260                 265                 270

Asp Ser Pro Val Ser Ala Asn Ile Pro Asn Gly Phe Asn Arg Ala Glu
        275                 280                 285

Phe Gly Val Arg Pro Pro His Leu Met Asp Phe Met Asn Ser Leu Phe
    290                 295                 300

Val Thr Ala Glu Thr Val Arg Ser Gln Thr Val Trp Gly Gly His Leu
305                 310                 315                 320

Val Ser Ser Arg Asn Thr Ala Gly Asn Arg Ile Asn Phe Pro Ser Tyr
                325                 330                 335

Gly Val Phe Asn Pro Gly Gly Ala Ile Trp Ile Ala Asp Glu Asp Pro
            340                 345                 350

Arg Pro Phe Tyr Arg Thr Leu Ser Asp Pro Val Phe Val Arg Gly Gly
        355                 360                 365

Phe Gly Asn Pro His Tyr Val Leu Gly Leu Arg Gly Val Ala Phe Gln
    370                 375                 380

Gln Thr Gly Thr Asn His Thr Arg Thr Phe Arg Asn Ser Gly Thr Ile
385                 390                 395                 400

Asp Ser Leu Asp Glu Ile Pro Pro Gln Asp Asn Ser Gly Ala Pro Trp
                405                 410                 415

Asn Asp Tyr Ser His Val Leu Asn His Val Thr Phe Val Arg Trp Pro
            420                 425                 430

Gly Glu Ile Ser Gly Ser Asp Ser Trp Arg Ala Pro Met Phe Ser Trp
        435                 440                 445

Thr His Arg Ser Ala Thr Pro Thr Asn Thr Ile Asp Pro Glu Arg Ile
450                 455                 460

Thr Gln Ile Pro Leu Val Lys Ala His Thr Leu Gln Ser Gly Thr Thr
465                 470                 475                 480

Val Val Arg Gly Pro Gly Phe Thr Gly Gly Asp Ile Leu Arg Arg Thr
                485                 490                 495

Ser Gly Gly Pro Phe Ala Tyr Thr Ile Val Asn Ile Asn Gly Gln Leu
        500                 505                 510

Pro Gln Arg Tyr Arg Ala Arg Ile Arg Tyr Ala Ser Thr Thr Asn Leu
    515                 520                 525

Arg Ile Tyr Val Thr Val Ala Gly Glu Arg Ile Phe Ala Gly Gln Phe
530                 535                 540

Asn Lys Thr Met Asp Thr Gly Asp Pro Leu Thr Phe Gln Ser Phe Ser
545                 550                 555                 560

Tyr Ala Thr Ile Asn Thr Ala Phe Thr Phe Pro Met Ser Gln Ser Ser
                565                 570                 575

Phe Thr Val Gly Ala Asp Thr Phe Ser Ser Gly Asn Glu Val Tyr Ile
            580                 585                 590

Asp Arg Phe Glu Leu Ile Pro Val Thr Ala Thr Phe Glu Ala Glu Tyr
        595                 600                 605
```

```
Asp  Leu  Glu  Arg  Ala  Gln  Lys  Ala  Val  Asn  Ala  Leu  Phe  Thr  Ser  Ile
     610                 615                      620
Asn  Gln  Ile  Gly  Ile  Lys  Thr  Asp  Val  Thr  Asp  Tyr  His  Ile  Asp  Gln
625                      630                      635                           640
Val  Ser  Asn  Leu  Val  Asp  Cys  Leu  Ser  Asp  Glu  Phe  Cys  Leu  Asp  Glu
                    645                 650                           655
Lys  Arg  Glu  Leu  Ser  Glu  Lys  Val  Lys  His  Ala  Lys  Arg  Leu  Ser  Asp
               660                 665                           670
Glu  Arg  Asn  Leu  Leu  Gln  Asp  Pro  Asn  Phe  Lys  Gly  Ile  Asn  Arg  Gln
          675                 680                      685
Leu  Asp  Arg  Gly  Trp  Arg  Gly  Ser  Thr  Asp  Ile  Thr  Ile  Gln  Arg  Gly
     690                 695                      700
Asp  Asp  Val  Phe  Lys  Glu  Asn  Tyr  Val  Thr  Leu  Pro  Gly  Thr  Phe  Asp
705                      710                      715                           720
Glu  Cys  Tyr  Pro  Thr  Tyr  Leu  Tyr  Gln  Lys  Ile  Asp  Glu  Ser  Lys  Leu
                    725                 730                           735
Lys  Pro  Tyr  Thr  Arg  Tyr  Gln  Leu  Arg  Gly  Tyr  Ile  Glu  Asp  Ser  Gln
               740                 745                           750
Asp  Leu  Glu  Ile  Tyr  Leu  Ile  Arg  Tyr  Asn  Ala  Lys  His  Glu  Thr  Val
          755                 760                      765
Asn  Val  Leu  Gly  Thr  Gly  Ser  Leu  Trp  Pro  Leu  Ser  Val  Gln  Ser  Pro
     770                 775                      780
Ile  Arg  Lys  Cys  Gly  Glu  Pro  Asn  Arg  Cys  Ala  Pro  His  Leu  Glu  Trp
785                      790                      795                           800
Asn  Pro  Asp  Leu  Asp  Cys  Ser  Cys  Arg  Asp  Gly  Glu  Lys  Cys  Ala  His
                    805                 810                           815
His  Ser  His  His  Phe  Ser  Leu  Asp  Ile  Asp  Val  Gly  Cys  Thr  Asp  Leu
               820                 825                           830
Asn  Glu  Asp  Leu  Asp  Val  Trp  Val  Ile  Phe  Lys  Ile  Lys  Thr  Gln  Asp
          835                 840                      845
Gly  His  Ala  Arg  Leu  Gly  Asn  Leu  Glu  Phe  Leu  Glu  Glu  Lys  Pro  Leu
     850                 855                      860
Val  Gly  Glu  Ala  Leu  Ala  Arg  Val  Lys  Arg  Ala  Glu  Lys  Lys  Trp  Arg
865                      870                      875                           880
Asp  Lys  Arg  Glu  Lys  Leu  Glu  Leu  Glu  Thr  Asn  Ile  Val  Tyr  Lys  Glu
                    885                 890                           895
Ala  Lys  Glu  Ser  Val  Asp  Ala  Leu  Phe  Val  Asn  Ser  Gln  Tyr  Asp  Gln
               900                 905                           910
Leu  Gln  Ala  Asp  Thr  Asn  Ile  Ala  Met  Ile  His  Ala  Ala  Asp  Lys  Arg
          915                 920                      925
Val  His  Arg  Ile  Arg  Glu  Ala  Tyr  Leu  Pro  Glu  Leu  Ser  Val  Ile  Pro
     930                 935                      940
Gly  Val  Asn  Val  Asp  Ile  Phe  Glu  Glu  Leu  Lys  Gly  Arg  Ile  Phe  Thr
945                      950                      955                           960
Ala  Phe  Phe  Leu  Tyr  Asp  Ala  Arg  Asn  Val  Ile  Lys  Asn  Gly  Asp  Phe
                    965                 970                           975
Asn  Asn  Gly  Leu  Ser  Cys  Trp  Asn  Val  Lys  Gly  His  Val  Asp  Val  Glu
               980                 985                           990
Glu  Gln  Asn  Asn  His  Arg  Ser  Val  Leu  Val  Val  Pro  Glu  Trp  Glu  Ala
          995                 1000                     1005
Glu  Val  Ser  Gln  Glu  Val  Arg  Val  Cys  Pro  Gly  Arg  Gly  Tyr  Ile  Leu
     1010                1015                     1020
Arg  Val  Thr  Ala  Tyr  Lys  Glu  Gly  Tyr  Gly  Glu  Gly  Cys  Val  Thr  Ile
```

|  |  | 1025 |  |  |  |  | 1030 |  |  |  |  | 1035 |  |  |  |  | 1040 |
|---|---|---|---|---|---|---|---|---|---|---|---|---|---|---|---|---|---|

His Glu Ile Glu Asn Asn Thr Asp Glu Leu Lys Phe Ser Asn Cys Val
                1045                    1050                1055

Glu Glu Glu Val Tyr Pro Asn Asn Thr Val Thr Cys Asn Asp Tyr Thr
            1060                1065                1070

Ala Asn Gln Glu Glu Tyr Gly Gly Ala Tyr Thr Ser Arg Asn Arg Gly
            1075                1080                1085

Tyr Asp Glu Thr Tyr Gly Ser Asn Ser Ser Val Pro Ala Asp Tyr Ala
        1090                1095                1100

Ser Val Tyr Glu Glu Lys Ser Tyr Thr Asp Gly Arg Arg Asp Asn Pro
1105                1110                1115                1120

Cys Glu Ser Asn Arg Gly Tyr Gly Asp Tyr Thr Pro Leu Pro Ala Gly
                1125                1130                1135

Tyr Val Thr Lys Glu Leu Glu Tyr Phe Pro Glu Thr Asp Lys Val Trp
            1140                1145                1150

Ile Glu Ile Gly Glu Thr Glu Gly Thr Phe Ile Val Asp Ser Val Glu
            1155                1160                1165

Leu Leu Leu Met Glu Glu
            1170

( 2 ) INFORMATION FOR SEQ ID NO:26:

( i ) SEQUENCE CHARACTERISTICS:
        ( A ) LENGTH: 3444 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

```
ATGGAAAATA ATATTCAAAA TCAATGCGTA CCTTACAATT GTTTAAATAA TCCTGAAGTA        60
GAAATACTGA ACGAAGAACG CAGCACCGGC CGCCTGCCGC TGGACATCAG CCTGAGCCTT       120
ACACGTTTCC TTTTGAGTGA ATTTGTTCCA GGTGTGGGAG TTGCGTTTGG ATTATTTGAT       180
TTAATATGGG GTTTTATAAC TCCTTCTGAT GGAGCTTAT TTCTTTTACA GATTGAACAA        240
TTGATTGAGC AAAGAATAGA AACATTGGAA AGGAACCGGG CAATTACTAC ATTACGAGGG       300
TTAGCAGATA GCTATGAAAT TTATATTGAA GCACTAAGAG AGTGGGAAGC AAATCCTAAT       360
AATGCACAAT TAAGGGAAGA TGTGCGTATT CGATTGCTA ATACAGACGA CGCTTTAATA        420
ACAGCAATAA ATAATTTTAC ACTTACAAGT TTTGAAATCC CTCTTTTATC GGTCTATGTT       480
CAAGCGGCGA ATTTACATTT ATCACTATTA GAGACGCTG TATCGTTTGG GCAGGGTTGG        540
GGACTGGATA TAGCTACTGT TAATAATCAT TATAATAGAT TAATAAATCT TATTCATAGA       600
TATACGAAAC ATTGTTTGGA CACATACAAT CAAGGATTAG AAAACTTAAG AGGTACTAAT       660
ACTCGACAAT GGGCAAGATT CAATCAGTTT AGGAGAGATT TAACACTTAC TGTATTAGAT       720
ATCGTTGCTC TTTTTCCGAA CTACGATGTT AGAACATATC CAATTCAAAC GTCATCCAA        780
TTAACAAGGG AAATTTATAC AAGTTCAGTA ATTGAGGATT CTCCAGTTTC TGCTAATATA       840
CCTAATGGTT TTAATAGGGC GGAATTTGGA GTTAGACCGC CCATCTTAT GGACTTTATG        900
AATTCTTTGT TTGTAACTGC AGAGACTGTT AGAAGTCAAA CTGTGTGGGG AGGACACTTA       960
GTTAGTTCAC GAAATACGGC TGGTAACCGT ATAAATTTCC CTAGTTACGG GGTCTTCAAT      1020
CCTGGTGGCG CCATTTGGAT TGCAGATGAG GATCCACGTC CTTTTTATCG GACATTATCA      1080
GATCCTGTTT TTGTCCGAGG AGGATTTGGG AATCCTCATT ATGTACTGGG GCTTAGGGGA      1140
```

| | | | | | | |
|---|---|---|---|---|---|---|
| GTAGCATTTC | AACAAACTGG | TACGAACCAC | ACCCGAACAT | TTAGAAATAG | TGGGACCATA | 1200 |
| GATTCTCTAG | ATGAAATCCC | ACCTCAGGAT | AATAGTGGGG | CACCTTGGAA | TGATTATAGT | 1260 |
| CATGTATTAA | ATCATGTTAC | ATTTGTACGA | TGGCCAGGTG | AGATTTCAGG | AAGTGATTCA | 1320 |
| TGGAGAGCTC | CAATGTTTTC | TTGGACGCAC | CGTAGTGCAA | CCCCTACAAA | TACAATTGAT | 1380 |
| CCGGAGAGGA | TTACTCAAAT | ACCATTGGTA | AAAGCACATA | CACTTCAGTC | AGGTACTACT | 1440 |
| GTTGTAAGAG | GGCCCGGGTT | TACGGGAGGA | GATATTCTTC | GACGAACAAG | TGGAGGACCA | 1500 |
| TTTGCTTATA | CTATTGTTAA | TATAAATGGG | CAATTACCCC | AAAGGTATCG | TGCAAGAATA | 1560 |
| CGCTATGCCT | CTACTACAAA | TCTAAGAATT | TACGTAACGG | TTGCAGGTGA | ACGGATTTTT | 1620 |
| GCTGGTCAAT | TTAACAAAAC | AATGGATACC | GGTGACCCAT | TAACATTCCA | ATCTTTTAGT | 1680 |
| TACGCAACTA | TTAATACAGC | TTTTACATTC | CCAATGAGCC | AGAGTAGTTT | CACAGTAGGT | 1740 |
| GCTGATACTT | TTAGTTCAGG | GAATGAAGTT | TATATAGACA | GATTTGAATT | GATTCCAGTT | 1800 |
| ACTGCAACAT | TTGAAGCAGA | ATATGATTTA | GAAAGAGCAC | AAAAGGCGGT | GAATGCGCTG | 1860 |
| TTTACTTCTA | TAAACCAAAT | AGGGATAAAA | ACAGATGTGA | CGGATTATCA | TATCGATCGA | 1920 |
| GTATCCAATT | TAGTTGAGTG | TTTATCTGAT | GAATTTTGTC | TGGATGAAAA | AAAAGAATTG | 1980 |
| TCCGAGAAAG | TCAAACATGC | GAAGCGACTT | AGTGATGAGC | GGAATTTACT | TCAAGATCCA | 2040 |
| AACTTTAGAG | GGATCAATAG | ACAACTAGAC | CGTGGCTGGA | GAGGAAGTAC | GGATATTACC | 2100 |
| ATCCAAGGAG | GCGATGACGT | ATTCAAAGAG | AATTACGTTA | CGCTATTGGG | TACCTTTGAT | 2160 |
| GAGTGCTATC | CAACGTATTT | ATATCAAAAA | ATAGATGAGT | CGAAATTAAA | AGCCTATACC | 2220 |
| CGTTACCAAT | TAAGAGGGTA | TATCGAAGAT | AGTCAAGACT | TAGAAATCTA | TTTAATTCGC | 2280 |
| TACAATGCCA | AACACGAAAC | AGTAAATGTG | CCAGGTACGG | GTTCCTTATG | GCCGCTTTCA | 2340 |
| GCCCCAAGTC | CAATCGGAAA | ATGTGCCCAT | CATTCCCATC | ATTTCTCCTT | GGACATTGAT | 2400 |
| GTTGGATGTA | CAGACTTAAA | TGAGGACTTA | GGTGTATGGG | TGATATTCAA | GATTAAGACG | 2460 |
| CAAGATGGCC | ATGCAAGACT | AGGAAATCTA | GAATTTCTCG | AAGAGAAACC | ATTAGTAGGA | 2520 |
| GAAGCACTAG | CTCGTGTGAA | AAGAGCGGAG | AAAAAATGGA | GAGACAAACG | TGAAAAATTG | 2580 |
| GAATGGGAAA | CAAATATTGT | TTATAAAGAG | GCAAAGAAT | CTGTAGATGC | TTTATTTGTA | 2640 |
| AACTCTCAAT | ATGATAGATT | ACAAGCGGAT | ACCAACATCG | CGATGATTCA | TGCGGCAGAT | 2700 |
| AAACGCGTTC | ATAGCATTCG | AGAAGCTTAT | CTGCCTGAGC | TGTCTGTGAT | TCCGGGTGTC | 2760 |
| AATGCGGCTA | TTTTTGAAGA | ATTAGAAGGG | CGTATTTTCA | CTGCATTCTC | CCTATATGAT | 2820 |
| GCGAGAAATG | TCATTAAAAA | TGGTGATTTT | AATAATGGCT | TATCCTGCTG | GAACGTGAAA | 2880 |
| GGGCATGTAG | ATGTAGAAGA | ACAAAACAAC | CACCGTTCGG | TCCTTGTTGT | TCCGGAATGG | 2940 |
| GAAGCAGAAG | TGTCACAAGA | AGTTCGTGTC | TGTCCGGGTC | GTGGCTATAT | CCTTCGTGTC | 3000 |
| ACAGCGTACA | AGGAGGGATA | TGGAGAAGGT | TGCGTAACCA | TCATGAGAT | CGAGAACAAT | 3060 |
| ACAGACGAAC | TGAAGTTTAG | CAACTGTGTA | GAAGAGGAAG | TATATCCAAA | CAACACGGTA | 3120 |
| ACGTGTAATG | ATTATACTGC | GACTCAAGAA | GAATATGAGG | GTACGTACAC | TTCTCGTAAT | 3180 |
| CGAGGATATG | ACGGAGCCTA | TGAAAGCAAT | TCTTCTGTAC | CAGCTGATTA | TGCATCAGCC | 3240 |
| TATGAAGAAA | AAGCATATAC | AGATGGACGA | AGAGACAATC | CTTGTGAATC | TAACAGAGGA | 3300 |
| TATGGGGATT | ACACACCACT | ACCAGCTGGC | TATGTGACAA | AAGAATTAGA | GTACTTCCCA | 3360 |
| GAAACCGATA | AGGTATGGAT | TGAGATCGGA | GAAACGGAAG | GAACATTCAT | CGTGGACAGC | 3420 |
| GTGGAATTAC | TTCTTATGGA | GGAA | | | | 3444 |

( 2 ) INFORMATION FOR SEQ ID NO:27:

(i) SEQUENCE CHARACTERISTICS:
    (A) LENGTH: 1148 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO:27:

```
Met Glu Asn Asn Ile Gln Asn Gln Cys Val Pro Tyr Asn Cys Leu Asn
 1               5                  10                  15
Asn Pro Glu Val Glu Ile Leu Asn Glu Glu Arg Ser Thr Gly Arg Leu
             20                  25                  30
Pro Leu Asp Ile Ser Leu Ser Leu Thr Arg Phe Leu Leu Ser Glu Phe
         35                  40                  45
Val Pro Gly Val Gly Val Ala Phe Gly Leu Phe Asp Leu Ile Trp Gly
     50                  55                  60
Phe Ile Thr Pro Ser Asp Trp Ser Leu Phe Leu Leu Gln Ile Glu Gln
 65                  70                  75                  80
Leu Ile Glu Gln Arg Ile Glu Thr Leu Glu Arg Asn Arg Ala Ile Thr
                 85                  90                  95
Thr Leu Arg Gly Leu Ala Asp Ser Tyr Glu Ile Tyr Ile Glu Ala Leu
            100                 105                 110
Arg Glu Trp Glu Ala Asn Pro Asn Asn Ala Gln Leu Arg Glu Asp Val
        115                 120                 125
Arg Ile Arg Phe Ala Asn Thr Asp Asp Ala Leu Ile Thr Ala Ile Asn
130                 135                 140
Asn Phe Thr Leu Thr Ser Phe Glu Ile Pro Leu Leu Ser Val Tyr Val
145                 150                 155                 160
Gln Ala Ala Asn Leu His Leu Ser Leu Leu Arg Asp Ala Val Ser Phe
                165                 170                 175
Gly Gln Gly Trp Gly Leu Asp Ile Ala Thr Val Asn Asn His Tyr Asn
            180                 185                 190
Arg Leu Ile Asn Leu Ile His Arg Tyr Thr Lys His Cys Leu Asp Thr
        195                 200                 205
Tyr Asn Gln Gly Leu Glu Asn Leu Arg Gly Thr Asn Thr Arg Gln Trp
210                 215                 220
Ala Arg Phe Asn Gln Phe Arg Arg Asp Leu Thr Leu Thr Val Leu Asp
225                 230                 235                 240
Ile Val Ala Leu Phe Pro Asn Tyr Asp Val Arg Thr Tyr Pro Ile Gln
                245                 250                 255
Thr Ser Ser Gln Leu Thr Arg Glu Ile Tyr Thr Ser Ser Val Ile Glu
            260                 265                 270
Asp Ser Pro Val Ser Ala Asn Ile Pro Asn Gly Phe Asn Arg Ala Glu
        275                 280                 285
Phe Gly Val Arg Pro Pro His Leu Met Asp Phe Met Asn Ser Leu Phe
290                 295                 300
Val Thr Ala Glu Thr Val Arg Ser Gln Thr Val Trp Gly Gly His Leu
305                 310                 315                 320
Val Ser Ser Arg Asn Thr Ala Gly Asn Arg Ile Asn Phe Pro Ser Tyr
                325                 330                 335
Gly Val Phe Asn Pro Gly Gly Ala Ile Trp Ile Ala Asp Glu Asp Pro
            340                 345                 350
Arg Pro Phe Tyr Arg Thr Leu Ser Asp Pro Val Phe Val Arg Gly Gly
        355                 360                 365
```

```
Phe  Gly  Asn  Pro  His  Tyr  Val  Leu  Gly  Leu  Arg  Gly  Val  Ala  Phe  Gln
     370                 375                      380

Gln  Thr  Gly  Thr  Asn  His  Thr  Arg  Thr  Phe  Arg  Asn  Ser  Gly  Thr  Ile
385                      390                      395                      400

Asp  Ser  Leu  Asp  Glu  Ile  Pro  Pro  Gln  Asp  Asn  Ser  Gly  Ala  Pro  Trp
                    405                      410                          415

Asn  Asp  Tyr  Ser  His  Val  Leu  Asn  His  Val  Thr  Phe  Val  Arg  Trp  Pro
                    420                      425                     430

Gly  Glu  Ile  Ser  Gly  Ser  Asp  Ser  Trp  Arg  Ala  Pro  Met  Phe  Ser  Trp
               435                 440                      445

Thr  His  Arg  Ser  Ala  Thr  Pro  Thr  Asn  Thr  Ile  Asp  Pro  Glu  Arg  Ile
     450                      455                      460

Thr  Gln  Ile  Pro  Leu  Val  Lys  Ala  His  Thr  Leu  Gln  Ser  Gly  Thr  Thr
465                      470                      475                      480

Val  Val  Arg  Gly  Pro  Gly  Phe  Thr  Gly  Gly  Asp  Ile  Leu  Arg  Arg  Thr
                    485                      490                          495

Ser  Gly  Gly  Pro  Phe  Ala  Tyr  Thr  Ile  Val  Asn  Ile  Asn  Gly  Gln  Leu
               500                 505                      510

Pro  Gln  Arg  Tyr  Arg  Ala  Arg  Ile  Arg  Tyr  Ala  Ser  Thr  Asn  Leu
          515                      520                      525

Arg  Ile  Tyr  Val  Thr  Val  Ala  Gly  Glu  Arg  Ile  Phe  Ala  Gly  Gln  Phe
     530                      535                      540

Asn  Lys  Thr  Met  Asp  Thr  Gly  Asp  Pro  Leu  Thr  Phe  Gln  Ser  Phe  Ser
545                      550                      555                      560

Tyr  Ala  Thr  Ile  Asn  Thr  Ala  Phe  Thr  Phe  Pro  Met  Ser  Gln  Ser  Ser
                    565                      570                      575

Phe  Thr  Val  Gly  Ala  Asp  Thr  Phe  Ser  Ser  Gly  Asn  Glu  Val  Tyr  Ile
               580                 585                      590

Asp  Arg  Phe  Glu  Leu  Ile  Pro  Val  Thr  Ala  Thr  Phe  Glu  Ala  Glu  Tyr
          595                      600                      605

Asp  Leu  Glu  Arg  Ala  Gln  Lys  Ala  Val  Asn  Ala  Leu  Phe  Thr  Ser  Ile
     610                      615                      620

Asn  Gln  Ile  Gly  Ile  Lys  Thr  Asp  Val  Thr  Asp  Tyr  His  Ile  Asp  Arg
625                      630                      635                      640

Val  Ser  Asn  Leu  Val  Glu  Cys  Leu  Ser  Asp  Glu  Phe  Cys  Leu  Asp  Glu
                    645                      650                      655

Lys  Lys  Glu  Leu  Ser  Glu  Lys  Val  Lys  His  Ala  Lys  Arg  Leu  Ser  Asp
               660                 665                      670

Glu  Arg  Asn  Leu  Leu  Gln  Asp  Pro  Asn  Phe  Arg  Gly  Ile  Asn  Arg  Gln
          675                      680                      685

Leu  Asp  Arg  Gly  Trp  Arg  Gly  Ser  Thr  Asp  Ile  Thr  Ile  Gln  Gly  Gly
     690                      695                      700

Asp  Asp  Val  Phe  Lys  Glu  Asn  Tyr  Val  Thr  Leu  Leu  Gly  Thr  Phe  Asp
705                      710                      715                      720

Glu  Cys  Tyr  Pro  Thr  Tyr  Leu  Tyr  Gln  Lys  Ile  Asp  Glu  Ser  Lys  Leu
                    725                      730                      735

Lys  Ala  Tyr  Thr  Arg  Tyr  Gln  Leu  Arg  Gly  Tyr  Ile  Glu  Asp  Ser  Gln
               740                 745                      750

Asp  Leu  Glu  Ile  Tyr  Leu  Ile  Arg  Tyr  Asn  Ala  Lys  His  Glu  Thr  Val
          755                      760                      765

Asn  Val  Pro  Gly  Thr  Gly  Ser  Leu  Trp  Pro  Leu  Ser  Ala  Pro  Ser  Pro
     770                      775                      780

Ile  Gly  Lys  Cys  Ala  His  His  Ser  His  His  Phe  Ser  Leu  Asp  Ile  Asp
785                      790                      795                      800
```

| | | | | | | | | | | | | | | |
|---|---|---|---|---|---|---|---|---|---|---|---|---|---|---|
| Val | Gly | Cys | Thr | Asp<br>805 | Leu | Asn | Glu | Asp<br>810 | Leu | Gly | Val | Trp | Val<br>815 | Ile | Phe |
| Lys | Ile | Lys | Thr<br>820 | Gln | Asp | Gly | His | Ala<br>825 | Arg | Leu | Gly | Asn | Leu<br>830 | Glu | Phe |
| Leu | Glu | Glu<br>835 | Lys | Pro | Leu | Val | Gly<br>840 | Glu | Ala | Leu | Ala | Arg<br>845 | Val | Lys | Arg |
| Ala | Glu<br>850 | Lys | Lys | Trp | Arg | Asp<br>855 | Lys | Arg | Glu | Lys | Leu<br>860 | Glu | Trp | Glu | Thr |
| Asn<br>865 | Ile | Val | Tyr | Lys | Glu<br>870 | Ala | Lys | Glu | Ser | Val<br>875 | Asp | Ala | Leu | Phe | Val<br>880 |
| Asn | Ser | Gln | Tyr | Asp<br>885 | Arg | Leu | Gln | Ala | Asp<br>890 | Thr | Asn | Ile | Ala | Met<br>895 | Ile |
| His | Ala | Ala | Asp<br>900 | Lys | Arg | Val | His | Ser<br>905 | Ile | Arg | Glu | Ala | Tyr<br>910 | Leu | Pro |
| Glu | Leu | Ser<br>915 | Val | Ile | Pro | Gly | Val<br>920 | Asn | Ala | Ala | Ile | Phe<br>925 | Glu | Glu | Leu |
| Glu | Gly<br>930 | Arg | Ile | Phe | Thr | Ala<br>935 | Phe | Ser | Leu | Tyr | Asp<br>940 | Ala | Arg | Asn | Val |
| Ile<br>945 | Lys | Asn | Gly | Asp | Phe<br>950 | Asn | Asn | Gly | Leu | Ser<br>955 | Cys | Trp | Asn | Val | Lys<br>960 |
| Gly | His | Val | Asp | Val<br>965 | Glu | Glu | Gln | Asn | Asn<br>970 | His | Arg | Ser | Val | Leu<br>975 | Val |
| Val | Pro | Glu | Trp<br>980 | Glu | Ala | Glu | Val | Ser<br>985 | Gln | Glu | Val | Arg | Val<br>990 | Cys | Pro |
| Gly | Arg | Gly<br>995 | Tyr | Ile | Leu | Arg | Val<br>1000 | Thr | Ala | Tyr | Lys | Glu<br>1005 | Gly | Tyr | Gly |
| Glu | Gly<br>1010 | Cys | Val | Thr | Ile | His<br>1015 | Glu | Ile | Glu | Asn | Asn<br>1020 | Thr | Asp | Glu | Leu |
| Lys<br>1025 | Phe | Ser | Asn | Cys | Val<br>1030 | Glu | Glu | Val | Tyr | Pro<br>1035 | Asn | Asn | Thr | Val<br>1040 |
| Thr | Cys | Asn | Asp | Tyr<br>1045 | Thr | Ala | Thr | Gln | Glu<br>1050 | Glu | Tyr | Glu | Gly | Thr<br>1055 | Tyr |
| Thr | Ser | Arg | Asn<br>1060 | Arg | Gly | Tyr | Asp | Gly<br>1065 | Ala | Tyr | Glu | Ser | Asn<br>1070 | Ser | Ser |
| Val | Pro | Ala | Asp<br>1075 | Tyr | Ala | Ser | Ala<br>1080 | Tyr | Glu | Glu | Lys | Ala<br>1085 | Tyr | Thr | Asp |
| Gly | Arg<br>1090 | Arg | Asp | Asn | Pro | Cys<br>1095 | Glu | Ser | Asn | Arg | Gly<br>1100 | Tyr | Gly | Asp | Tyr |
| Thr<br>1105 | Pro | Leu | Pro | Ala | Gly<br>1110 | Tyr | Val | Thr | Lys | Glu<br>1115 | Leu | Glu | Tyr | Phe | Pro<br>1120 |
| Glu | Thr | Asp | Lys | Val<br>1125 | Trp | Ile | Glu | Ile | Gly<br>1130 | Glu | Thr | Glu | Gly | Thr<br>1135 | Phe |
| Ile | Val | Asp | Ser | Val<br>1140 | Glu | Leu | Leu | Leu | Met<br>1145 | Glu | Glu |

( 2 ) INFORMATION FOR SEQ ID NO:28:

( i ) SEQUENCE CHARACTERISTICS:
        ( A ) LENGTH: 3522 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

-continued

| | | | | | | |
|---|---|---|---|---|---|---|
| ATGGAAAATA | ATATTCAAAA | TCAATGCGTA | CCTTACAATT | GTTTAAATAA | TCCTGAAGTA | 60 |
| GAAATACTGA | ACGAAGAACG | CAGCACCGGC | CGCCTGCCGC | TGGACATCAG | CCTGAGCCTT | 120 |
| ACACGTTTCC | TTTTGAGTGA | ATTTGTTCCA | GGTGTGGGAG | TTGCGTTTGG | ATTATTTGAT | 180 |
| TTAATATGGG | GTTTTATAAC | TCCTTCTGAT | TGGAGCTTAT | TTCTTTTACA | GATTGAACAA | 240 |
| TTGATTGAGC | AAAGAATAGA | AACATTGGAA | AGGAACCGGG | CAATTACTAC | ATTACGAGGG | 300 |
| TTAGCAGATA | GCTATGAAAT | TTATATTGAA | GCACTAAGAG | AGTGGGAAGC | AAATCCTAAT | 360 |
| AATGCACAAT | TAAGGGAAGA | TGTGCGTATT | CGATTGCTA | ATACAGACGA | CGCTTTAATA | 420 |
| ACAGCAATAA | ATAATTTTAC | ACTTACAAGT | TTTGAAATCC | CTCTTTTATC | GGTCTATGTT | 480 |
| CAAGCGGCGA | ATTTACATTT | ATCACTATTA | AGAGACGCTG | TATCGTTTGG | GCAGGGTTGG | 540 |
| GGACTGGATA | TAGCTACTGT | TAATAATCAT | TATAATAGAT | TAATAAATCT | TATTCATAGA | 600 |
| TATACGAAAC | ATTGTTTGGA | CACATACAAT | CAAGGATTAG | AAAACTTAAG | AGGTACTAAT | 660 |
| ACTCGACAAT | GGGCAAGATT | CAATCAGTTT | AGGAGAGATT | TAACACTTAC | TGTATTAGAT | 720 |
| ATCGTTGCTC | TTTTTCCGAA | CTACGATGTT | AGAACATATC | CAATTCAAAC | GTCATCCCAA | 780 |
| TTAACAAGGG | AAATTTATAC | AAGTTCAGTA | ATTGAGGATT | CTCCAGTTTC | TGCTAATATA | 840 |
| CCTAATGGTT | TTAATAGGGC | GGAATTTGGA | GTTAGACCGC | CCCATCTTAT | GGACTTTATG | 900 |
| AATTCTTTGT | TTGTAACTGC | AGAGACTGTT | AGAAGTCAAA | CTGTGTGGGG | AGGACACTTA | 960 |
| GTTAGTTCAC | GAAATACGGC | TGGTAACCGT | ATAAATTTCC | CTAGTTACGG | GGTCTTCAAT | 1020 |
| CCTGGTGGCG | CCATTTGGAT | TGCAGATGAG | GATCCACGTC | CTTTTTATCG | GACATTATCA | 1080 |
| GATCCTGTTT | TTGTCCGAGG | AGGATTTGGG | AATCCTCATT | ATGTACTGGG | GCTTAGGGGA | 1140 |
| GTAGCATTTC | AACAAACTGG | TACGAACCAC | ACCCGAACAT | TTAGAAATAG | TGGGACCATA | 1200 |
| GATTCTCTAG | ATGAAATCCC | ACCTCAGGAT | AATAGTGGGG | CACCTTGGAA | TGATTATAGT | 1260 |
| CATGTATTAA | ATCATGTTAC | ATTTGTACGA | TGGCCAGGTG | AGATTTCAGG | AAGTGATTCA | 1320 |
| TGGAGAGCTC | CAATGTTTTC | TTGGACGCAC | CGTAGTGCAA | CCCCTACAAA | TACAATTGAT | 1380 |
| CCGGAGAGGA | TTACTCAAAT | ACCATTGGTA | AAAGCACATA | CACTTCAGTC | AGGTACTACT | 1440 |
| GTTGTAAGAG | GGCCCGGGTT | TACGGGAGGA | GATATTCTTC | GACGAACAAG | TGGAGGACCA | 1500 |
| TTTGCTTATA | CTATTGTTAA | TATAAATGGG | CAATTACCCC | AAAGGTATCG | TGCAAGAATA | 1560 |
| CGCTATGCCT | CTACTACAAA | TCTAAGAATT | TACGTAACGG | TTGCAGGTGA | ACGGATTTT | 1620 |
| GCTGGTCAAT | TTAACAAAAC | AATGGATACC | GGTGACCCAT | TAACATTCCA | ATCTTTTAGT | 1680 |
| TACGCAACTA | TTAATACAGC | TTTTACATTC | CCAATGAGCC | AGAGTAGTTT | CACAGTAGGT | 1740 |
| GCTGATACTT | TTAGTTCAGG | GAATGAAGTT | TATATAGACA | GATTGAATT | GATTCCAGTT | 1800 |
| ACTGCAACAT | TTGAAGCAGA | ATATGATTTA | GAAAGAGCAC | AAAAGGCGGT | GAATGCGCTG | 1860 |
| TTTACTTCTA | TAAACCAAAT | AGGGATAAAA | ACAGATGTGA | CGGATTATCA | TATCGATCGA | 1920 |
| GTGTCCAATT | TAGTTACGTA | TTTATCGGAT | GAATTTTGTC | TGGATGAAAA | GCGAGAATTG | 1980 |
| TCCGAGAAAG | TCAAACATGC | GAAGCGACTC | AGTGATGAAC | GCAATTTACT | CCAAGATTCA | 2040 |
| AATTTCAAAG | ACATTAATAG | GCAACCAGAA | CGTGGGTGGG | GCGGAAGTAC | AGGGATTACC | 2100 |
| ATCCAAGGAG | GGGATGACGT | ATTTAAAGAA | AATTACGTCA | CACTATCAGG | TACCTTTGAT | 2160 |
| GAGTGCTATC | CAACATATTT | GTATCAAAAA | ATCGATGAAT | CAAAATTAAA | AGCCTTTACC | 2220 |
| CGTTATCAAT | TAAGAGGGTA | TATCGAAGAT | AGTCAAGACT | TAGAAATCTA | TTTAATTCGC | 2280 |
| TACAATGCAA | AACATGAAAC | AGTAAATGTG | CCAGGTACGG | GTTCCTTATG | GCCGCTTTCA | 2340 |
| GCCCAAAGTC | CAATCGGAAA | GTGTGGAGAG | CCGAATCGAT | GCGCGCCACA | CCTTGAATGG | 2400 |

-continued

| | | | | |
|---|---|---|---|---|
| AATCCTGACT | TAGATTGTTC | GTGTAGGGAT | GGAGAAAAGT | GTGCCCATCA | TTCGCATCAT | 2460 |
| TTCTCCTTAG | ACATTGATGT | AGGATGTACA | GACTTAAATG | AGGACCTAGG | TGTATGGGTG | 2520 |
| ATCTTTAAGA | TTAAGACGCA | AGATGGGCAC | GCAAGACTAG | GGAATCTAGA | GTTTCTCGAA | 2580 |
| GAGAAACCAT | TAGTAGGAGA | AGCGCTAGCT | CGTGTGAAAA | GAGCGGAGAA | AAAATGGAGA | 2640 |
| GACAAACGTG | AAAAATTGGA | ATGGGAAACA | AATATCGTTT | ATAAAGAGGC | AAAAGAATCT | 2700 |
| GTAGATGCTT | TATTTGTAAA | CTCTCAATAT | GATCAATTAC | AAGCGGATAC | GAATATTGCC | 2760 |
| ATGATTCATG | CGGCAGATAA | ACGTGTTCAT | AGCATTCGAG | AAGCTTATCT | GCCTGAGCTG | 2820 |
| TCTGTGATTC | CGGGTGTCAA | TGCGGCTATT | TTTGAAGAAT | TAGAAGGGCG | TATTTTCACT | 2880 |
| GCATTCTCCC | TATATGATGC | GAGAAATGTC | ATTAAAAATG | GTGATTTTAA | TAATGGCTTA | 2940 |
| TCCTGCTGGA | ACGTGAAAGG | GCATGTAGAT | GTAGAAGAAC | AAAACAACCA | CCGTTCGGTC | 3000 |
| CTTGTTGTTC | CGGAATGGGA | AGCAGAAGTG | TCACAAGAAG | TTCGTGTCTG | TCCGGGTCGT | 3060 |
| GGCTATATCC | TTCGTGTCAC | AGCGTACAAG | GAGGGATATG | GAGAAGGTTG | CGTAACCATT | 3120 |
| CATGAGATCG | AGAACAATAC | AGACGAACTG | AAGTTTAGCA | ACTGTGTAGA | AGAGGAAGTA | 3180 |
| TATCCAAACA | ACACGGTAAC | GTGTAATGAT | TATACTGCGA | CTCAAGAAGA | ATATGAGGGT | 3240 |
| ACGTACACTT | CTCGTAATCG | AGGATATGAC | GGAGCCTATG | AAAGCAATTC | TTCTGTACCA | 3300 |
| GCTGATTATG | CATCAGCCTA | TGAAGAAAAA | GCATATACAG | ATGGACGAAG | AGACAATCCT | 3360 |
| TGTGAATCTA | ACAGAGGATA | TGGGGATTAC | ACACCACTAC | CAGCTGGCTA | TGTGACAAAA | 3420 |
| GAATTAGAGT | ACTTCCCAGA | AACCGATAAG | GTATGGATTG | AGATCGGAGA | AACGGAAGGA | 3480 |
| ACATTCATCG | TGGACAGCGT | GGAATTACTT | CTTATGGAGG | AA | | 3522 |

( 2 ) INFORMATION FOR SEQ ID NO:29:

( i ) SEQUENCE CHARACTERISTICS:
        ( A ) LENGTH: 1174 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:29:

```
Met Glu Asn Asn Ile Gln Asn Gln Cys Val Pro Tyr Asn Cys Leu Asn
  1               5                  10                  15

Asn Pro Glu Val Glu Ile Leu Asn Glu Glu Arg Ser Thr Gly Arg Leu
             20                  25                  30

Pro Leu Asp Ile Ser Leu Ser Leu Thr Arg Phe Leu Leu Ser Glu Phe
         35                  40                  45

Val Pro Gly Val Gly Val Ala Phe Gly Leu Phe Asp Leu Ile Trp Gly
     50                  55                  60

Phe Ile Thr Pro Ser Asp Trp Ser Leu Phe Leu Leu Gln Ile Glu Gln
 65                  70                  75                  80

Leu Ile Glu Gln Arg Ile Glu Thr Leu Glu Arg Asn Arg Ala Ile Thr
                 85                  90                  95

Thr Leu Arg Gly Leu Ala Asp Ser Tyr Glu Ile Tyr Ile Glu Ala Leu
            100                 105                 110

Arg Glu Trp Glu Ala Asn Pro Asn Asn Ala Gln Leu Arg Glu Asp Val
        115                 120                 125

Arg Ile Arg Phe Ala Asn Thr Asp Asp Ala Leu Ile Thr Ala Ile Asn
    130                 135                 140

Asn Phe Thr Leu Thr Ser Phe Glu Ile Pro Leu Leu Ser Val Tyr Val
145                 150                 155                 160
```

-continued

Gln Ala Ala Asn Leu His Leu Ser Leu Leu Arg Asp Ala Val Ser Phe
                165                 170                 175

Gly Gln Gly Trp Gly Leu Asp Ile Ala Thr Val Asn Asn His Tyr Asn
            180                 185                 190

Arg Leu Ile Asn Leu Ile His Arg Tyr Thr Lys His Cys Leu Asp Thr
        195                 200                 205

Tyr Asn Gln Gly Leu Glu Asn Leu Arg Gly Thr Asn Thr Arg Gln Trp
    210                 215                 220

Ala Arg Phe Asn Gln Phe Arg Arg Asp Leu Thr Leu Thr Val Leu Asp
225                 230                 235                 240

Ile Val Ala Leu Phe Pro Asn Tyr Asp Val Arg Thr Tyr Pro Ile Gln
                245                 250                 255

Thr Ser Ser Gln Leu Thr Arg Glu Ile Tyr Thr Ser Ser Val Ile Glu
            260                 265                 270

Asp Ser Pro Val Ser Ala Asn Ile Pro Asn Gly Phe Asn Arg Ala Glu
        275                 280                 285

Phe Gly Val Arg Pro Pro His Leu Met Asp Phe Met Asn Ser Leu Phe
    290                 295                 300

Val Thr Ala Glu Thr Val Arg Ser Gln Thr Val Trp Gly Gly His Leu
305                 310                 315                 320

Val Ser Ser Arg Asn Thr Ala Gly Asn Arg Ile Asn Phe Pro Ser Tyr
                325                 330                 335

Gly Val Phe Asn Pro Gly Gly Ala Ile Trp Ile Ala Asp Glu Asp Pro
            340                 345                 350

Arg Pro Phe Tyr Arg Thr Leu Ser Asp Pro Val Phe Val Arg Gly Gly
        355                 360                 365

Phe Gly Asn Pro His Tyr Val Leu Gly Leu Arg Gly Val Ala Phe Gln
    370                 375                 380

Gln Thr Gly Thr Asn His Thr Arg Thr Phe Arg Asn Ser Gly Thr Ile
385                 390                 395                 400

Asp Ser Leu Asp Glu Ile Pro Pro Gln Asp Asn Ser Gly Ala Pro Trp
                405                 410                 415

Asn Asp Tyr Ser His Val Leu Asn His Val Thr Phe Val Arg Trp Pro
            420                 425                 430

Gly Glu Ile Ser Gly Ser Asp Ser Trp Arg Ala Pro Met Phe Ser Trp
        435                 440                 445

Thr His Arg Ser Ala Thr Pro Thr Asn Thr Ile Asp Pro Glu Arg Ile
    450                 455                 460

Thr Gln Ile Pro Leu Val Lys Ala His Thr Leu Gln Ser Gly Thr Thr
465                 470                 475                 480

Val Val Arg Gly Pro Gly Phe Thr Gly Gly Asp Ile Leu Arg Arg Thr
                485                 490                 495

Ser Gly Gly Pro Phe Ala Tyr Thr Ile Val Asn Ile Asn Gly Gln Leu
            500                 505                 510

Pro Gln Arg Tyr Arg Ala Arg Ile Arg Tyr Ala Ser Thr Thr Asn Leu
        515                 520                 525

Arg Ile Tyr Val Thr Val Ala Gly Glu Arg Ile Phe Ala Gly Gln Phe
    530                 535                 540

Asn Lys Thr Met Asp Thr Gly Asp Pro Leu Thr Phe Gln Ser Phe Ser
545                 550                 555                 560

Tyr Ala Thr Ile Asn Thr Ala Phe Thr Phe Pro Met Ser Gln Ser Ser
                565                 570                 575

Phe Thr Val Gly Ala Asp Thr Phe Ser Ser Gly Asn Glu Val Tyr Ile

```
                                580                         585                         590
    Asp   Arg   Phe   Glu   Leu   Ile   Pro   Val   Thr   Ala   Thr   Phe   Glu   Ala   Glu   Tyr
                      595                         600                         605
    Asp   Leu   Glu   Arg   Ala   Gln   Lys   Ala   Val   Asn   Ala   Leu   Phe   Thr   Ser   Ile
                610                         615                         620
    Asn   Gln   Ile   Gly   Ile   Lys   Thr   Asp   Val   Thr   Asp   Tyr   His   Ile   Asp   Arg
    625                         630                         635                         640
    Val   Ser   Asn   Leu   Val   Thr   Tyr   Leu   Ser   Asp   Glu   Phe   Cys   Leu   Asp   Glu
                            645                         650                         655
    Lys   Arg   Glu   Leu   Ser   Glu   Lys   Val   Lys   His   Ala   Lys   Arg   Leu   Ser   Asp
                            660                         665                         670
    Glu   Arg   Asn   Leu   Leu   Gln   Asp   Ser   Asn   Phe   Lys   Asp   Ile   Asn   Arg   Gln
                675                         680                         685
    Pro   Glu   Arg   Gly   Trp   Gly   Gly   Ser   Thr   Gly   Ile   Thr   Ile   Gln   Gly   Gly
                690                         695                         700
    Asp   Asp   Val   Phe   Lys   Glu   Asn   Tyr   Val   Thr   Leu   Ser   Gly   Thr   Phe   Asp
    705                         710                         715                         720
    Glu   Cys   Tyr   Pro   Thr   Tyr   Leu   Tyr   Gln   Lys   Ile   Asp   Glu   Ser   Lys   Leu
                            725                         730                         735
    Lys   Ala   Phe   Thr   Arg   Tyr   Gln   Leu   Arg   Gly   Tyr   Ile   Glu   Asp   Ser   Gln
                            740                         745                         750
    Asp   Leu   Glu   Ile   Tyr   Leu   Ile   Arg   Tyr   Asn   Ala   Lys   His   Glu   Thr   Val
                            755                         760                         765
    Asn   Val   Pro   Gly   Thr   Gly   Ser   Leu   Trp   Pro   Leu   Ser   Ala   Gln   Ser   Pro
                770                         775                         780
    Ile   Gly   Lys   Cys   Gly   Glu   Pro   Asn   Arg   Cys   Ala   Pro   His   Leu   Glu   Trp
    785                         790                         795                         800
    Asn   Pro   Asp   Leu   Asp   Cys   Ser   Cys   Arg   Asp   Gly   Glu   Lys   Cys   Ala   His
                            805                         810                         815
    His   Ser   His   His   Phe   Ser   Leu   Asp   Ile   Asp   Val   Gly   Cys   Thr   Asp   Leu
                            820                         825                         830
    Asn   Glu   Asp   Leu   Gly   Val   Trp   Val   Ile   Phe   Lys   Ile   Lys   Thr   Gln   Asp
                            835                         840                         845
    Gly   His   Ala   Arg   Leu   Gly   Asn   Leu   Glu   Phe   Leu   Glu   Glu   Lys   Pro   Leu
                850                         855                         860
    Val   Gly   Glu   Ala   Leu   Ala   Arg   Val   Lys   Arg   Ala   Glu   Lys   Lys   Trp   Arg
    865                         870                         875                         880
    Asp   Lys   Arg   Glu   Lys   Leu   Glu   Trp   Glu   Thr   Asn   Ile   Val   Tyr   Lys   Glu
                            885                         890                         895
    Ala   Lys   Glu   Ser   Val   Asp   Ala   Leu   Phe   Val   Asn   Ser   Gln   Tyr   Asp   Gln
                            900                         905                         910
    Leu   Gln   Ala   Asp   Thr   Asn   Ile   Ala   Met   Ile   His   Ala   Ala   Asp   Lys   Arg
                            915                         920                         925
    Val   His   Ser   Ile   Arg   Glu   Ala   Tyr   Leu   Pro   Glu   Leu   Ser   Val   Ile   Pro
                930                         935                         940
    Gly   Val   Asn   Ala   Ala   Ile   Phe   Glu   Glu   Leu   Glu   Gly   Arg   Ile   Phe   Thr
    945                         950                         955                         960
    Ala   Phe   Ser   Leu   Tyr   Asp   Ala   Arg   Asn   Val   Ile   Lys   Asn   Gly   Asp   Phe
                            965                         970                         975
    Asn   Asn   Gly   Leu   Ser   Cys   Trp   Asn   Val   Lys   Gly   His   Val   Asp   Val   Glu
                            980                         985                         990
    Glu   Gln   Asn   Asn   His   Arg   Ser   Val   Leu   Val   Val   Pro   Glu   Trp   Glu   Ala
                995                         1000                        1005
```

Glu Val Ser Gln Glu Val Arg Val Cys Pro Gly Arg Gly Tyr Ile Leu
            1010                1015                1020

Arg Val Thr Ala Tyr Lys Glu Gly Tyr Gly Glu Gly Cys Val Thr Ile
1025                1030                1035                1040

His Glu Ile Glu Asn Asn Thr Asp Glu Leu Lys Phe Ser Asn Cys Val
            1045                1050                1055

Glu Glu Glu Val Tyr Pro Asn Asn Thr Val Thr Cys Asn Asp Tyr Thr
            1060                1065                1070

Ala Thr Gln Glu Glu Tyr Glu Gly Thr Tyr Thr Ser Arg Asn Arg Gly
            1075                1080                1085

Tyr Asp Gly Ala Tyr Glu Ser Asn Ser Ser Val Pro Ala Asp Tyr Ala
            1090                1095                1100

Ser Ala Tyr Glu Glu Lys Ala Tyr Thr Asp Gly Arg Arg Asp Asn Pro
1105                1110                1115                1120

Cys Glu Ser Asn Arg Gly Tyr Gly Asp Tyr Thr Pro Leu Pro Ala Gly
            1125                1130                1135

Tyr Val Thr Lys Glu Leu Glu Tyr Phe Pro Glu Thr Asp Lys Val Trp
            1140                1145                1150

Ile Glu Ile Gly Glu Thr Glu Gly Thr Phe Ile Val Asp Ser Val Glu
            1155                1160                1165

Leu Leu Leu Met Glu Glu
            1170

( 2 ) INFORMATION FOR SEQ ID NO:30:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:30:

Xaa Xaa Ile Asp Xaa Xaa Glu Xaa Xaa Xaa Xaa Xaa
                    5                   10

( 2 ) INFORMATION FOR SEQ ID NO:31:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:31:

Tyr Pro Asn Asn Thr Val Thr Cys
                    5

( 2 ) INFORMATION FOR SEQ ID NO:32:

( i ) SEQUENCE CHARACTERISTICS:
        ( A ) LENGTH: 1184 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:32:

Cys Arg Tyr Ile Phe Ala Met Pro Glu Pro Met Glu Asn Asn Ile Gln
1               5                   10                  15

```
Asn Gln Cys Val Pro Tyr Asn Cys Leu Asn Asn Pro Glu Val Glu Ile
             20                  25                      30
Leu Asn Glu Glu Arg Ser Thr Gly Arg Leu Pro Leu Asp Ile Ser Leu
         35                  40                  45
Ser Leu Thr Arg Phe Leu Leu Ser Glu Phe Val Pro Gly Val Gly Val
     50                  55                  60
Ala Phe Gly Leu Phe Asp Leu Ile Trp Gly Phe Ile Thr Pro Ser Asp
 65                      70                  75                  80
Trp Ser Leu Phe Leu Leu Gln Ile Glu Gln Leu Ile Glu Gln Arg Ile
                 85                  90                      95
Glu Thr Leu Glu Arg Asn Arg Ala Ile Thr Thr Leu Arg Gly Leu Ala
             100                 105                     110
Asp Ser Tyr Glu Ile Tyr Ile Glu Ala Leu Arg Glu Trp Glu Ala Asn
         115                 120                     125
Pro Asn Asn Ala Gln Leu Arg Glu Asp Val Arg Ile Arg Phe Ala Asn
     130                 135                     140
Thr Asp Asp Ala Leu Ile Thr Ala Ile Asn Asn Phe Thr Leu Thr Ser
145                     150                 155                 160
Phe Glu Ile Pro Leu Leu Ser Val Tyr Val Gln Ala Ala Asn Leu His
                 165                 170                     175
Leu Ser Leu Leu Arg Asp Ala Val Ser Phe Gly Gln Gly Trp Gly Leu
             180                 185                     190
Asp Ile Ala Thr Val Asn Asn His Tyr Asn Arg Leu Ile Asn Leu Ile
         195                 200                     205
His Arg Tyr Thr Lys His Cys Leu Asp Thr Tyr Asn Gln Gly Leu Glu
     210                 215                     220
Asn Leu Arg Gly Thr Asn Thr Arg Gln Trp Ala Arg Phe Asn Gln Phe
225                     230                 235                 240
Arg Arg Asp Leu Thr Leu Thr Val Leu Asp Ile Val Ala Leu Phe Pro
                 245                 250                     255
Asn Tyr Asp Val Arg Thr Tyr Pro Ile Gln Thr Ser Ser Gln Leu Thr
             260                 265                     270
Arg Glu Ile Tyr Thr Ser Ser Val Ile Glu Asp Ser Pro Val Ser Ala
         275                 280                     285
Asn Ile Pro Asn Gly Phe Asn Arg Ala Glu Phe Gly Val Arg Pro Pro
     290                 295                     300
His Leu Met Asp Phe Met Asn Ser Leu Phe Val Thr Ala Glu Thr Val
305                     310                 315                 320
Arg Ser Gln Thr Val Trp Gly Gly His Leu Val Ser Ser Arg Asn Thr
                 325                 330                     335
Ala Gly Asn Arg Ile Asn Phe Pro Ser Tyr Gly Val Phe Asn Pro Gly
             340                 345                     350
Gly Ala Ile Trp Ile Ala Asp Glu Asp Pro Arg Pro Phe Tyr Arg Thr
         355                 360                     365
Leu Ser Asp Pro Val Phe Val Arg Gly Gly Phe Gly Asn Pro His Tyr
     370                 375                     380
Val Leu Gly Leu Arg Gly Val Ala Phe Gln Gln Thr Gly Thr Asn His
385                     390                 395                 400
Thr Arg Thr Phe Arg Asn Ser Gly Thr Ile Asp Ser Leu Asp Glu Ile
                 405                 410                     415
Pro Pro Gln Asp Asn Ser Gly Ala Pro Trp Asn Asp Tyr Ser His Val
             420                 425                     430
Leu Asn His Val Thr Phe Val Arg Trp Pro Gly Glu Ile Ser Gly Ser
```

|   |   |   |   |   | 435 |   |   |   |   | 440 |   |   |   |   | 445 |   |   |
|---|---|---|---|---|---|---|---|---|---|---|---|---|---|---|---|---|---|

Asp Ser Trp Arg Ala Pro Met Phe Ser Trp Thr His Arg Ser Ala Thr
450                     455                     460

Pro Thr Asn Thr Ile Asp Pro Glu Arg Ile Thr Gln Ile Pro Leu Val
465                 470                 475                 480

Lys Ala His Thr Leu Gln Ser Gly Thr Thr Val Val Arg Gly Pro Gly
                485                 490                 495

Phe Thr Gly Gly Asp Ile Leu Arg Arg Thr Ser Gly Gly Pro Phe Ala
            500                 505                 510

Tyr Thr Ile Val Asn Ile Asn Gly Gln Leu Pro Gln Arg Tyr Arg Ala
        515                 520                 525

Arg Ile Arg Tyr Ala Ser Thr Thr Asn Leu Arg Ile Tyr Val Thr Val
530                 535                 540

Ala Gly Glu Arg Ile Phe Ala Gly Gln Phe Asn Lys Thr Met Asp Thr
545                 550                 555                 560

Gly Asp Pro Leu Thr Phe Gln Ser Phe Ser Tyr Ala Thr Ile Asn Thr
                565                 570                 575

Ala Phe Thr Phe Pro Met Ser Gln Ser Ser Phe Thr Val Gly Ala Asp
            580                 585                 590

Thr Phe Ser Ser Gly Asn Glu Val Tyr Ile Asp Arg Phe Glu Leu Ile
        595                 600                 605

Pro Val Thr Ala Thr Phe Glu Ala Glu Tyr Asp Leu Glu Arg Ala Gln
610                 615                 620

Lys Ala Val Asn Ala Leu Phe Thr Ser Ile Asn Gln Ile Gly Ile Lys
625                 630                 635                 640

Thr Asp Val Thr Asp Tyr His Ile Asp Gln Val Ser Asn Leu Val Asp
                645                 650                 655

Cys Leu Ser Asp Glu Phe Cys Leu Asp Glu Lys Arg Glu Leu Ser Glu
            660                 665                 670

Lys Val Lys His Ala Lys Arg Leu Ser Asp Glu Arg Asn Leu Leu Gln
        675                 680                 685

Asp Pro Asn Phe Lys Gly Ile Asn Arg Gln Leu Asp Arg Gly Trp Arg
690                 695                 700

Gly Ser Thr Asp Ile Thr Ile Gln Arg Gly Asp Asp Val Phe Lys Glu
705                 710                 715                 720

Asn Tyr Val Thr Leu Pro Gly Thr Phe Asp Glu Cys Tyr Pro Thr Tyr
                725                 730                 735

Leu Tyr Gln Lys Ile Asp Glu Ser Lys Leu Lys Pro Tyr Thr Arg Tyr
            740                 745                 750

Gln Leu Arg Gly Tyr Ile Glu Asp Ser Gln Asp Leu Glu Ile Tyr Leu
        755                 760                 765

Ile Arg Tyr Asn Ala Lys His Glu Thr Val Asn Val Leu Gly Thr Gly
770                 775                 780

Ser Leu Trp Pro Leu Ser Val Gln Ser Pro Ile Arg Lys Cys Gly Glu
785                 790                 795                 800

Pro Asn Arg Cys Ala Pro His Leu Glu Trp Asn Pro Asp Leu Asp Cys
                805                 810                 815

Ser Cys Arg Asp Gly Glu Lys Cys Ala His His Ser His His Phe Ser
            820                 825                 830

Leu Asp Ile Asp Val Gly Cys Thr Asp Leu Asn Glu Asp Leu Asp Val
        835                 840                 845

Trp Val Ile Phe Lys Ile Lys Thr Gln Asp Gly His Ala Arg Leu Gly
850                 855                 860

```
Asn  Leu  Glu  Phe  Leu  Glu  Glu  Lys  Pro  Leu  Val  Gly  Glu  Ala  Leu  Ala
865                 870                 875                           880

Arg  Val  Lys  Arg  Ala  Glu  Lys  Lys  Trp  Arg  Asp  Lys  Arg  Glu  Lys  Leu
                    885                      890                     895

Glu  Leu  Glu  Thr  Asn  Ile  Val  Tyr  Lys  Glu  Ala  Lys  Glu  Ser  Val  Asp
                900                      905                      910

Ala  Leu  Phe  Val  Asn  Ser  Gln  Tyr  Asp  Gln  Leu  Gln  Ala  Asp  Thr  Asn
              915                     920                      925

Ile  Ala  Met  Ile  His  Ala  Ala  Asp  Lys  Arg  Val  His  Arg  Ile  Arg  Glu
              930                     935                      940

Ala  Tyr  Leu  Pro  Glu  Leu  Ser  Val  Ile  Pro  Gly  Val  Asn  Val  Asp  Ile
945                      950                      955                           960

Phe  Glu  Glu  Leu  Lys  Gly  Arg  Ile  Phe  Thr  Ala  Phe  Phe  Leu  Tyr  Asp
                    965                      970                     975

Ala  Arg  Asn  Val  Ile  Lys  Asn  Gly  Asp  Phe  Asn  Asn  Gly  Leu  Ser  Cys
              980                     985                      990

Trp  Asn  Val  Lys  Gly  His  Val  Asp  Val  Glu  Glu  Gln  Asn  Asn  His  Arg
         995                     1000                       1005

Ser  Val  Leu  Val  Val  Pro  Glu  Trp  Glu  Ala  Glu  Val  Ser  Gln  Glu  Val
         1010                    1015                      1020

Arg  Val  Cys  Pro  Gly  Arg  Gly  Tyr  Ile  Leu  Arg  Val  Thr  Ala  Tyr  Lys
1025                     1030                     1035                          1040

Glu  Gly  Tyr  Gly  Glu  Gly  Cys  Val  Thr  Ile  His  Glu  Ile  Glu  Asn  Asn
                    1045                    1050                     1055

Thr  Asp  Glu  Leu  Lys  Phe  Ser  Asn  Cys  Val  Glu  Glu  Glu  Val  Tyr  Pro
              1060                     1065                     1070

Asn  Asn  Thr  Val  Thr  Cys  Asn  Asp  Tyr  Thr  Ala  Asn  Gln  Glu  Glu  Tyr
         1075                     1080                     1085

Gly  Gly  Ala  Tyr  Thr  Ser  Arg  Asn  Arg  Gly  Tyr  Asp  Glu  Thr  Tyr  Gly
         1090                     1095                     1100

Ser  Asn  Ser  Ser  Val  Pro  Ala  Asp  Tyr  Ala  Ser  Val  Tyr  Glu  Glu  Lys
1105                     1110                     1115                          1120

Ser  Tyr  Thr  Asp  Gly  Arg  Arg  Asp  Asn  Pro  Cys  Glu  Ser  Asn  Arg  Gly
                    1125                     1130                         1135

Tyr  Gly  Asp  Tyr  Thr  Pro  Leu  Pro  Ala  Gly  Tyr  Val  Thr  Lys  Glu  Leu
              1140                     1145                     1150

Glu  Tyr  Phe  Pro  Glu  Thr  Asp  Lys  Val  Trp  Ile  Glu  Ile  Gly  Glu  Thr
              1155                     1160                     1165

Glu  Gly  Thr  Phe  Ile  Val  Asp  Ser  Val  Glu  Leu  Leu  Leu  Met  Glu  Glu
              1170                     1175                     1180
```

( 2 ) INFORMATION FOR SEQ ID NO:33:

( i ) SEQUENCE CHARACTERISTICS:
        ( A ) LENGTH: 1165 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:33:

```
Cys  Arg  Tyr  Ile  Ala  Asx  Met  Pro  Glu  Pro  Met  Asp  Asn  Asn  Pro  Asn
1                   5                   10                      15

Ile  Asn  Glu  Cys  Ile  Pro  Tyr  Asn  Cys  Leu  Ser  Asn  Pro  Glu  Val  Glu
              20                      25                      30

Val  Leu  Gly  Gly  Glu  Arg  Ile  Glu  Thr  Gly  Tyr  Thr  Pro  Ile  Asp  Ile
```

|     |     |     |     | 35  |     |     |     | 40  |     |     |     | 45  |     |     |
| --- | --- | --- | --- | --- | --- | --- | --- | --- | --- | --- | --- | --- | --- | --- |
| Ser | Leu | Ser | Leu | Thr | Gln | Phe | Leu | Leu | Ser | Glu | Phe | Val | Pro | Gly | Ala |
|     | 50  |     |     |     |     | 55  |     |     |     |     | 60  |     |     |     |     |
| Gly | Phe | Val | Leu | Gly | Leu | Val | Asp | Ile | Ile | Trp | Gly | Ile | Phe | Gly | Pro |
| 65  |     |     |     |     | 70  |     |     |     |     | 75  |     |     |     |     | 80  |
| Ser | Gln | Trp | Asp | Ala | Phe | Leu | Val | Gln | Ile | Glu | Gln | Leu | Ile | Asn | Gln |
|     |     |     |     | 85  |     |     |     |     | 90  |     |     |     |     | 95  |     |
| Arg | Ile | Glu | Glu | Phe | Ala | Arg | Asn | Gln | Ala | Ile | Ser | Arg | Leu | Glu | Gly |
|     |     |     | 100 |     |     |     |     | 105 |     |     |     |     | 110 |     |     |
| Leu | Ser | Asn | Leu | Tyr | Gln | Ile | Tyr | Ala | Glu | Ser | Phe | Arg | Glu | Trp | Glu |
|     |     | 115 |     |     |     |     | 120 |     |     |     |     | 125 |     |     |     |
| Ala | Asp | Pro | Thr | Asn | Pro | Ala | Leu | Arg | Glu | Glu | Met | Arg | Ile | Gln | Phe |
|     | 130 |     |     |     |     | 135 |     |     |     |     | 140 |     |     |     |     |
| Asn | Asp | Met | Asn | Ser | Ala | Leu | Thr | Thr | Ala | Ile | Pro | Leu | Phe | Ala | Val |
| 145 |     |     |     |     | 150 |     |     |     |     | 155 |     |     |     |     | 160 |
| Gln | Asn | Tyr | Gln | Val | Pro | Leu | Leu | Ser | Val | Tyr | Val | Gln | Ala | Ala | Asn |
|     |     |     |     | 165 |     |     |     |     | 170 |     |     |     |     | 175 |     |
| Leu | His | Leu | Ser | Val | Leu | Arg | Asp | Val | Ser | Val | Phe | Gly | Gln | Arg | Trp |
|     |     |     | 180 |     |     |     |     | 185 |     |     |     |     | 190 |     |     |
| Gly | Phe | Asp | Ala | Ala | Thr | Ile | Asn | Ser | Arg | Tyr | Asn | Asp | Leu | Thr | Arg |
|     |     | 195 |     |     |     |     | 200 |     |     |     |     | 205 |     |     |     |
| Leu | Ile | Gly | Asn | Tyr | Thr | Asp | His | Ala | Val | Arg | Trp | Tyr | Asn | Thr | Gly |
|     | 210 |     |     |     |     | 215 |     |     |     |     | 220 |     |     |     |     |
| Leu | Glu | Arg | Val | Trp | Gly | Pro | Asp | Ser | Arg | Asp | Trp | Ile | Arg | Tyr | Asn |
| 225 |     |     |     |     | 230 |     |     |     |     | 235 |     |     |     |     | 240 |
| Gln | Phe | Arg | Arg | Glu | Leu | Thr | Leu | Thr | Val | Leu | Asp | Ile | Val | Ser | Leu |
|     |     |     |     | 245 |     |     |     |     | 250 |     |     |     |     | 255 |     |
| Phe | Pro | Asn | Tyr | Asp | Ser | Arg | Thr | Tyr | Pro | Ile | Arg | Thr | Val | Ser | Gln |
|     |     |     | 260 |     |     |     |     | 265 |     |     |     |     | 270 |     |     |
| Leu | Thr | Arg | Glu | Ile | Tyr | Thr | Asn | Pro | Val | Leu | Glu | Asn | Phe | Asp | Gly |
|     |     | 275 |     |     |     |     | 280 |     |     |     |     | 285 |     |     |     |
| Ser | Phe | Arg | Gly | Ser | Ala | Gln | Gly | Ile | Glu | Gly | Ser | Ile | Arg | Ser | Pro |
|     | 290 |     |     |     |     | 295 |     |     |     |     | 300 |     |     |     |     |
| His | Leu | Met | Asp | Ile | Leu | Asn | Ser | Ile | Thr | Ile | Tyr | Thr | Asp | Ala | His |
| 305 |     |     |     |     | 310 |     |     |     |     | 315 |     |     |     |     | 320 |
| Arg | Gly | Glu | Tyr | Tyr | Trp | Ser | Gly | His | Gln | Ile | Met | Ala | Ser | Pro | Val |
|     |     |     |     | 325 |     |     |     |     | 330 |     |     |     |     | 335 |     |
| Gly | Phe | Ser | Gly | Pro | Glu | Phe | Thr | Phe | Pro | Leu | Tyr | Gly | Thr | Met | Gly |
|     |     |     | 340 |     |     |     |     | 345 |     |     |     |     | 350 |     |     |
| Asn | Ala | Ala | Pro | Gln | Gln | Arg | Ile | Val | Ala | Gln | Leu | Gly | Gln | Gly | Val |
|     |     | 355 |     |     |     |     | 360 |     |     |     |     | 365 |     |     |     |
| Tyr | Arg | Thr | Leu | Ser | Ser | Thr | Leu | Tyr | Arg | Arg | Pro | Phe | Asn | Ile | Gly |
|     | 370 |     |     |     |     | 375 |     |     |     |     | 380 |     |     |     |     |
| Ile | Asn | Asn | Gln | Gln | Leu | Ser | Val | Leu | Asp | Gly | Thr | Glu | Phe | Ala | Tyr |
| 385 |     |     |     |     | 390 |     |     |     |     | 395 |     |     |     |     | 400 |
| Gly | Thr | Ser | Ser | Asn | Leu | Pro | Ser | Ala | Val | Tyr | Arg | Lys | Ser | Gly | Thr |
|     |     |     |     | 405 |     |     |     |     | 410 |     |     |     |     | 415 |     |
| Val | Asp | Ser | Leu | Asp | Glu | Ile | Pro | Pro | Gln | Asn | Asn | Asn | Val | Pro | Pro |
|     |     |     | 420 |     |     |     |     | 425 |     |     |     |     | 430 |     |     |
| Arg | Gln | Gly | Phe | Ser | His | Arg | Leu | Ser | His | Val | Ser | Met | Phe | Arg | Ser |
|     |     | 435 |     |     |     |     | 440 |     |     |     |     | 445 |     |     |     |
| Gly | Phe | Ser | Asn | Ser | Ser | Val | Ser | Ile | Ile | Arg | Ala | Pro | Met | Phe | Ser |
|     | 450 |     |     |     |     | 455 |     |     |     |     | 460 |     |     |     |     |

| Trp | Ile | His | Arg | Ser | Ala | Glu | Phe | Asn | Asn | Ile | Ile | Pro | Ser | Ser | Gln |
| 465 | | | | 470 | | | | | 475 | | | | | | 480 |
| Ile | Thr | Gln | Ile | Pro | Leu | Thr | Lys | Ser | Thr | Asn | Leu | Gly | Ser | Gly | Thr |
| | | | | 485 | | | | | 490 | | | | | 495 | |
| Ser | Val | Val | Lys | Gly | Pro | Gly | Phe | Thr | Gly | Gly | Asp | Ile | Leu | Arg | Arg |
| | | | 500 | | | | | 505 | | | | | 510 | | |
| Thr | Ser | Pro | Gly | Gln | Ile | Ser | Thr | Leu | Arg | Val | Asn | Ile | Thr | Ala | Pro |
| | | 515 | | | | | 520 | | | | | 525 | | | |
| Leu | Ser | Gln | Arg | Tyr | Arg | Val | Arg | Ile | Arg | Tyr | Ala | Ser | Thr | Thr | Asn |
| 530 | | | | | 535 | | | | | 540 | | | | | |
| Leu | Gln | Phe | His | Thr | Ser | Ile | Asp | Gly | Arg | Pro | Ile | Asn | Gln | Gly | Asn |
| 545 | | | | | 550 | | | | | 555 | | | | | 560 |
| Phe | Ser | Ala | Thr | Met | Ser | Ser | Gly | Ser | Asn | Leu | Gln | Ser | Gly | Ser | Phe |
| | | | | 565 | | | | | 570 | | | | | 575 | |
| Arg | Thr | Val | Gly | Phe | Thr | Thr | Pro | Phe | Asn | Phe | Ser | Asn | Gly | Ser | Ser |
| | | | 580 | | | | | 585 | | | | | 590 | | |
| Val | Phe | Thr | Leu | Ser | Ala | His | Val | Phe | Asn | Ser | Gly | Asn | Glu | Val | Tyr |
| | | 595 | | | | | 600 | | | | | 605 | | | |
| Ile | Asp | Arg | Ile | Glu | Phe | Val | Pro | Ala | Glu | Val | Thr | Phe | Glu | Ala | Glu |
| | 610 | | | | | 615 | | | | | 620 | | | | |
| Tyr | Asp | Leu | Glu | Arg | Ala | Gln | Lys | Ala | Val | Asn | Glu | Leu | Phe | Thr | Ser |
| 625 | | | | | 630 | | | | | 635 | | | | | 640 |
| Ser | Asn | Gln | Ile | Gly | Leu | Lys | Thr | Asp | Val | Thr | Asp | Tyr | His | Ile | Asp |
| | | | | 645 | | | | | 650 | | | | | 655 | |
| Gln | Val | Ser | Asn | Leu | Val | Glu | Cys | Leu | Ser | Asp | Glu | Phe | Cys | Leu | Asp |
| | | | 660 | | | | | 665 | | | | | 670 | | |
| Glu | Lys | Lys | Glu | Leu | Ser | Glu | Lys | Val | Lys | His | Ala | Lys | Arg | Leu | Ser |
| | | 675 | | | | | 680 | | | | | 685 | | | |
| Asp | Glu | Arg | Asn | Leu | Leu | Gln | Asp | Pro | Asn | Phe | Arg | Gly | Ile | Asn | Arg |
| | 690 | | | | | 695 | | | | | 700 | | | | |
| Gln | Leu | Asp | Arg | Gly | Trp | Arg | Gly | Ser | Thr | Asp | Ile | Thr | Ile | Gln | Gly |
| 705 | | | | | 710 | | | | | 715 | | | | | 720 |
| Gly | Asp | Asp | Val | Phe | Lys | Glu | Asn | Tyr | Val | Thr | Leu | Leu | Gly | Thr | Phe |
| | | | | 725 | | | | | 730 | | | | | 735 | |
| Asp | Glu | Cys | Tyr | Pro | Thr | Tyr | Leu | Tyr | Gln | Lys | Ile | Asp | Glu | Ser | Lys |
| | | | 740 | | | | | 745 | | | | | 750 | | |
| Leu | Lys | Ala | Tyr | Thr | Arg | Tyr | Gln | Leu | Arg | Gly | Tyr | Ile | Glu | Asp | Ser |
| | | | 755 | | | | | 760 | | | | | 765 | | |
| Gln | Asp | Leu | Glu | Ile | Tyr | Leu | Ile | Arg | Tyr | Asn | Ala | Lys | His | Glu | Thr |
| | 770 | | | | | 775 | | | | | 780 | | | | |
| Val | Asn | Val | Pro | Gly | Thr | Gly | Ser | Leu | Trp | Pro | Leu | Ser | Ala | Pro | Ser |
| 785 | | | | | 790 | | | | | 795 | | | | | 800 |
| Pro | Ile | Gly | Lys | Cys | Ala | His | His | Ser | His | His | Phe | Ser | Leu | Asp | Ile |
| | | | | 805 | | | | | 810 | | | | | 815 | |
| Asp | Val | Gly | Cys | Thr | Asp | Leu | Asn | Glu | Asp | Leu | Gly | Val | Trp | Val | Ile |
| | | | 820 | | | | | 825 | | | | | 830 | | |
| Phe | Lys | Ile | Lys | Thr | Gln | Asp | Gly | His | Ala | Arg | Leu | Gly | Asn | Leu | Glu |
| | | 835 | | | | | 840 | | | | | 845 | | | |
| Phe | Leu | Glu | Glu | Lys | Pro | Leu | Val | Gly | Glu | Ala | Leu | Ala | Arg | Val | Lys |
| | 850 | | | | | 855 | | | | | 860 | | | | |
| Arg | Ala | Glu | Lys | Lys | Trp | Arg | Asp | Lys | Arg | Glu | Lys | Leu | Glu | Trp | Glu |
| 865 | | | | | 870 | | | | | 875 | | | | | 880 |
| Thr | Asn | Ile | Val | Tyr | Lys | Glu | Ala | Lys | Glu | Ser | Val | Asp | Ala | Leu | Phe |
| | | | | 885 | | | | | 890 | | | | | 895 | |

```
Val  Asn  Ser  Gln  Tyr  Asp  Arg  Leu  Gln  Ala  Asp  Thr  Asn  Ile  Ala  Met
               900                      905                          910

Ile  His  Ala  Ala  Asp  Lys  Arg  Val  His  Ser  Ile  Arg  Glu  Ala  Tyr  Leu
          915                      920                      925

Pro  Glu  Leu  Ser  Val  Ile  Pro  Gly  Val  Asn  Ala  Ala  Ile  Phe  Glu  Glu
     930                      935                      940

Leu  Glu  Gly  Arg  Ile  Phe  Thr  Ala  Phe  Ser  Leu  Tyr  Asp  Ala  Arg  Asn
945                      950                      955                          960

Val  Ile  Lys  Asn  Gly  Asp  Phe  Asn  Asn  Gly  Leu  Ser  Cys  Trp  Asn  Val
               965                      970                          975

Lys  Gly  His  Val  Asp  Val  Glu  Glu  Gln  Asn  Asn  His  Arg  Ser  Val  Leu
          980                      985                      990

Val  Val  Pro  Glu  Trp  Glu  Ala  Glu  Val  Ser  Gln  Glu  Val  Arg  Val  Cys
          995                      1000                     1005

Pro  Gly  Arg  Gly  Tyr  Ile  Leu  Arg  Val  Thr  Ala  Tyr  Lys  Glu  Gly  Tyr
          1010                     1015                     1020

Gly  Glu  Gly  Cys  Val  Thr  Ile  His  Glu  Ile  Glu  Asn  Asn  Thr  Asp  Glu
1025                     1030                     1035                          1040

Leu  Lys  Phe  Ser  Asn  Cys  Val  Glu  Glu  Val  Tyr  Pro  Asn  Asn  Thr
                    1045                     1050                     1055

Val  Thr  Cys  Asn  Asp  Tyr  Thr  Ala  Thr  Gln  Glu  Glu  Tyr  Glu  Gly  Thr
               1060                     1065                     1070

Tyr  Thr  Ser  Arg  Asn  Arg  Gly  Tyr  Asp  Gly  Ala  Tyr  Glu  Ser  Asn  Ser
          1075                     1080                     1085

Ser  Val  Pro  Ala  Asp  Tyr  Ala  Ser  Ala  Tyr  Glu  Glu  Lys  Ala  Tyr  Thr
          1090                     1095                     1100

Asp  Gly  Arg  Arg  Asp  Asn  Pro  Cys  Glu  Ser  Asn  Arg  Gly  Tyr  Gly  Asp
1105                     1110                     1115                          1120

Tyr  Thr  Pro  Leu  Pro  Ala  Gly  Tyr  Val  Thr  Lys  Glu  Leu  Glu  Tyr  Phe
               1125                     1130                          1135

Pro  Glu  Thr  Asp  Lys  Val  Trp  Ile  Glu  Ile  Gly  Glu  Thr  Glu  Gly  Thr
               1140                     1145                     1150

Phe  Ile  Val  Asp  Ser  Val  Glu  Leu  Leu  Leu  Met  Glu  Glu
               1155                     1160                1165
```

( 2 ) INFORMATION FOR SEQ ID NO:34:

( i ) SEQUENCE CHARACTERISTICS:
        ( A ) LENGTH: 1188 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:34:

```
Ala  Asx  Cys  Pro  Glu  Pro  Met  Asp  Asn  Asn  Pro  Asn  Ile  Asn  Glu  Cys
1                   5                     10                          15

Ile  Pro  Tyr  Asn  Cys  Leu  Ser  Asn  Pro  Glu  Val  Glu  Val  Leu  Gly  Gly
               20                     25                      30

Glu  Arg  Ile  Glu  Thr  Gly  Tyr  Thr  Pro  Ile  Asp  Ile  Ser  Leu  Ser  Leu
          35                     40                      45

Thr  Gln  Phe  Leu  Leu  Ser  Glu  Phe  Val  Pro  Gly  Ala  Gly  Phe  Val  Leu
     50                      55                      60

Gly  Leu  Val  Asp  Ile  Ile  Trp  Gly  Ile  Phe  Gly  Pro  Ser  Gln  Trp  Asp
65                      70                      75                           80
```

| | | | | | | | | | | | | | | |
|---|---|---|---|---|---|---|---|---|---|---|---|---|---|---|
| Ala | Phe | Leu | Val | Gln 85 | Ile | Glu | Gln | Leu 90 | Ile | Asn | Gln | Arg | Ile 95 | Glu |
| Phe | Ala | Arg | Asn 100 | Gln | Ala | Ile | Ser 105 | Arg | Leu | Glu | Gly | Leu 110 | Ser | Asn | Leu |
| Tyr | Gln | Ile 115 | Tyr | Ala | Glu | Ser | Phe 120 | Arg | Glu | Trp | Glu | Ala 125 | Asp | Pro | Thr |
| Asn | Pro 130 | Ala | Leu | Arg | Glu | Glu 135 | Met | Arg | Ile | Gln | Phe 140 | Asn | Asp | Met | Asn |
| Ser 145 | Ala | Leu | Thr | Thr | Ala 150 | Ile | Pro | Leu | Phe | Ala 155 | Val | Gln | Asn | Tyr | Gln 160 |
| Val | Pro | Leu | Leu | Ser 165 | Val | Tyr | Val | Gln | Ala 170 | Ala | Asn | Leu | His | Leu 175 | Ser |
| Val | Leu | Arg | Asp 180 | Val | Ser | Val | Phe | Gly 185 | Gln | Arg | Trp | Gly | Phe 190 | Asp | Ala |
| Ala | Thr | Ile 195 | Asn | Ser | Arg | Tyr | Asn 200 | Asp | Leu | Thr | Arg | Leu 205 | Ile | Gly | Asn |
| Tyr | Thr 210 | Asp | Tyr | Ala | Val | Arg 215 | Trp | Tyr | Asn | Thr | Gly 220 | Leu | Glu | Arg | Val |
| Trp 225 | Gly | Pro | Asp | Ser | Arg 230 | Asp | Trp | Val | Arg | Tyr 235 | Asn | Gln | Phe | Arg | Arg 240 |
| Glu | Leu | Thr | Leu | Thr 245 | Val | Leu | Asp | Ile | Val 250 | Ala | Leu | Phe | Pro | Asn 255 | Tyr |
| Asp | Ser | Arg | Arg 260 | Tyr | Pro | Ile | Arg | Thr 265 | Val | Ser | Gln | Leu | Thr 270 | Arg | Glu |
| Ile | Tyr | Thr 275 | Asn | Pro | Val | Leu | Glu 280 | Asn | Phe | Asp | Gly | Ser 285 | Phe | Arg | Gly |
| Ser | Ala 290 | Gln | Gly | Ile | Glu | Arg 295 | Ser | Ile | Arg | Ser | Pro 300 | His | Leu | Met | Asp |
| Ile 305 | Leu | Asn | Ser | Ile | Thr 310 | Ile | Tyr | Thr | Asp | Ala 315 | His | Arg | Gly | Tyr | Tyr 320 |
| Tyr | Trp | Ser | Gly | His 325 | Gln | Ile | Met | Ala | Ser 330 | Pro | Val | Gly | Phe | Ser 335 | Gly |
| Pro | Glu | Phe | Thr 340 | Phe | Pro | Leu | Tyr | Gly 345 | Thr | Met | Gly | Asn | Ala 350 | Ala | Pro |
| Gln | Gln | Arg 355 | Ile | Val | Ala | Gln | Leu 360 | Gly | Gln | Gly | Val | Tyr 365 | Arg | Thr | Leu |
| Ser | Ser 370 | Thr | Leu | Tyr | Arg | Arg 375 | Pro | Phe | Asn | Ile | Gly 380 | Ile | Asn | Asn | Gln |
| Gln 385 | Leu | Ser | Val | Leu | Asp 390 | Gly | Thr | Glu | Phe | Ala 395 | Tyr | Gly | Thr | Ser | Ser 400 |
| Asn | Leu | Pro | Ser | Ala 405 | Val | Tyr | Arg | Lys | Ser 410 | Gly | Thr | Val | Asp | Ser 415 | Leu |
| Asp | Glu | Ile | Pro 420 | Pro | Gln | Asn | Asn | Asn 425 | Val | Pro | Pro | Arg | Gln 430 | Gly | Phe |
| Ser | His | Arg 435 | Leu | Ser | His | Val | Ser 440 | Met | Phe | Arg | Ser | Gly 445 | Phe | Ser | Asn |
| Ser | Ser 450 | Val | Ser | Ile | Ile | Arg 455 | Ala | Pro | Met | Phe | Ser 460 | Trp | Ile | His | Arg |
| Ser 465 | Ala | Glu | Phe | Asn | Asn 470 | Ile | Ile | Ala | Ser | Asp 475 | Ser | Ile | Thr | Gln | Ile 480 |
| Pro | Ala | Val | Lys | Gly 485 | Asn | Phe | Leu | Phe | Asn 490 | Gly | Ser | Val | Ile | Ser 495 | Gly |
| Pro | Gly | Phe | Thr 500 | Gly | Gly | Asp | Leu | Val 505 | Arg | Leu | Asn | Ser | Ser 510 | Gly | Asn |

```
Asn  Ile  Gln  Asn  Arg  Gly  Tyr  Ile  Glu  Val  Pro  Ile  His  Phe  Pro  Ser
          515                 520                 525

Thr  Ser  Thr  Arg  Tyr  Arg  Val  Arg  Val  Arg  Tyr  Ala  Ser  Val  Thr  Pro
     530                 535                 540

Ile  His  Leu  Asn  Val  Asn  Trp  Gly  Asn  Ser  Ser  Ile  Phe  Ser  Asn  Thr
545                 550                 555                                560

Val  Pro  Ala  Thr  Ala  Thr  Ser  Leu  Asp  Asn  Leu  Gln  Ser  Ser  Asp  Phe
               565                 570                                575

Gly  Tyr  Phe  Glu  Ser  Ala  Asn  Ala  Phe  Thr  Ser  Ser  Leu  Gly  Asn  Ile
          580                      585                      590

Val  Gly  Val  Arg  Asn  Phe  Ser  Gly  Thr  Ala  Gly  Val  Ile  Ile  Asp  Arg
               595                 600                      605

Phe  Glu  Phe  Ile  Pro  Val  Thr  Ala  Thr  Leu  Glu  Ala  Glu  Tyr  Asn  Leu
     610                      615                 620

Glu  Arg  Ala  Gln  Lys  Ala  Val  Asn  Ala  Leu  Phe  Thr  Ser  Thr  Asn  Gln
625                      630                      635                      640

Leu  Gly  Leu  Lys  Thr  Asn  Val  Thr  Asp  Tyr  His  Ile  Asp  Gln  Val  Ser
               645                      650                      655

Asn  Leu  Val  Thr  Tyr  Leu  Ser  Asp  Glu  Phe  Cys  Leu  Asp  Glu  Lys  Arg
               660                 665                      670

Glu  Leu  Ser  Glu  Lys  Val  Lys  His  Ala  Lys  Arg  Leu  Ser  Asp  Glu  Arg
          675                 680                      685

Asn  Leu  Leu  Gln  Asp  Ser  Asn  Phe  Lys  Asp  Ile  Asn  Arg  Gln  Pro  Glu
     690                 695                 700

Arg  Gly  Trp  Gly  Gly  Ser  Thr  Gly  Ile  Thr  Ile  Gln  Gly  Gly  Asp  Asp
705                      710                 715                      720

Val  Phe  Lys  Glu  Asn  Tyr  Val  Thr  Leu  Ser  Gly  Thr  Phe  Asp  Glu  Cys
               725                 730                      735

Tyr  Pro  Thr  Tyr  Leu  Tyr  Gln  Lys  Ile  Asp  Glu  Ser  Lys  Leu  Lys  Ala
               740                 745                 750

Phe  Thr  Arg  Tyr  Gln  Leu  Arg  Gly  Tyr  Ile  Glu  Asp  Ser  Gln  Asp  Leu
          755                 760                 765

Glu  Ile  Tyr  Leu  Ile  Arg  Tyr  Asn  Ala  Lys  His  Glu  Thr  Val  Asn  Val
770                      775                      780

Pro  Gly  Thr  Gly  Ser  Leu  Trp  Pro  Leu  Ser  Ala  Gln  Ser  Pro  Ile  Gly
785                      790                 795                           800

Lys  Cys  Gly  Glu  Pro  Asn  Arg  Cys  Ala  Pro  His  Leu  Glu  Trp  Asn  Pro
               805                 810                      815

Asp  Leu  Asp  Cys  Ser  Cys  Arg  Asp  Gly  Glu  Lys  Cys  Ala  His  His  Ser
               820                 825                      830

His  His  Phe  Ser  Leu  Asp  Ile  Asp  Val  Gly  Cys  Thr  Asp  Leu  Asn  Glu
          835                 840                 845

Asp  Leu  Gly  Val  Trp  Val  Ile  Phe  Lys  Ile  Lys  Thr  Gln  Asp  Gly  His
     850                      855                 860

Ala  Arg  Leu  Gly  Asn  Leu  Glu  Phe  Leu  Glu  Glu  Lys  Pro  Leu  Val  Gly
865                      870                 875                           880

Glu  Ala  Leu  Ala  Arg  Val  Lys  Arg  Ala  Glu  Lys  Lys  Trp  Arg  Asp  Lys
                    885                      890                      895

Arg  Glu  Lys  Leu  Glu  Trp  Glu  Thr  Asn  Ile  Val  Tyr  Lys  Glu  Ala  Lys
               900                 905                      910

Glu  Ser  Val  Asp  Ala  Leu  Phe  Val  Asn  Ser  Gln  Tyr  Asp  Gln  Leu  Gln
          915                 920                      925

Ala  Asp  Thr  Asn  Ile  Ala  Met  Ile  His  Ala  Ala  Asp  Lys  Arg  Val  His
```

|  | 930 | | | | 935 | | | | 940 | | | |
|---|---|---|---|---|---|---|---|---|---|---|---|---|

Ser Ile Arg Glu Ala Tyr Leu Pro Glu Leu Ser Val Ile Pro Gly Val
945                     950                     955                     960

Asn Ala Ala Ile Phe Glu Glu Leu Glu Gly Arg Ile Phe Thr Ala Phe
                965                     970                     975

Ser Leu Tyr Asp Ala Arg Asn Val Ile Lys Asn Gly Asp Phe Asn Asn
            980                     985                     990

Gly Leu Ser Cys Trp Asn Val Lys Gly His Val Asp Val Glu Glu Gln
        995                     1000                    1005

Asn Asn His Arg Ser Val Leu Val Val Pro Glu Trp Glu Ala Glu Val
        1010                    1015                    1020

Ser Gln Glu Val Arg Val Cys Pro Gly Arg Gly Tyr Ile Leu Arg Val
1025                    1030                    1035                    1040

Thr Ala Tyr Lys Glu Gly Tyr Gly Glu Gly Cys Val Thr Ile His Glu
            1045                    1050                    1055

Ile Glu Asn Asn Thr Asp Glu Leu Lys Phe Ser Asn Cys Val Glu Glu
            1060                    1065                    1070

Glu Val Tyr Pro Asn Asn Thr Val Thr Cys Asn Asp Tyr Thr Ala Thr
            1075                    1080                    1085

Gln Glu Glu Tyr Glu Gly Thr Tyr Thr Ser Arg Asn Arg Gly Tyr Asp
            1090                    1095                    1100

Gly Ala Tyr Glu Ser Asn Ser Ser Val Pro Ala Asp Tyr Ala Ser Ala
1105                    1110                    1115                    1120

Tyr Glu Glu Lys Ala Tyr Thr Asp Gly Arg Arg Asp Asn Pro Cys Glu
            1125                    1130                    1135

Ser Asn Arg Gly Tyr Gly Asp Tyr Thr Pro Leu Pro Ala Gly Tyr Val
            1140                    1145                    1150

Thr Lys Glu Leu Glu Tyr Phe Pro Glu Thr Asp Lys Val Trp Ile Glu
            1155                    1160                    1165

Ile Gly Glu Thr Glu Gly Thr Phe Ile Val Asp Ser Val Glu Leu Leu
            1170                    1175                    1180

Leu Met Glu Glu
1185

( 2 ) INFORMATION FOR SEQ ID NO:35:

( i ) SEQUENCE CHARACTERISTICS:
        ( A ) LENGTH: 1148 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:35:

Met Glu Asn Asn Ile Gln Asn Gln Cys Val Pro Tyr Asn Cys Leu Asn
1                   5                       10                      15

Asn Pro Glu Val Glu Ile Leu Asn Glu Glu Arg Ser Thr Gly Arg Leu
                20                      25                      30

Pro Leu Asp Ile Ser Leu Ser Leu Thr Arg Phe Leu Leu Ser Glu Phe
            35                      40                      45

Val Pro Gly Val Gly Val Ala Phe Gly Leu Phe Asp Leu Ile Trp Gly
        50                      55                      60

Phe Ile Thr Pro Ser Asp Trp Ser Leu Phe Leu Leu Gln Ile Glu Gln
65                      70                      75                      80

Leu Ile Glu Gln Arg Ile Glu Thr Leu Glu Arg Asn Arg Ala Ile Thr
                85                      90                      95

```
Thr  Leu  Arg  Gly  Leu  Ala  Asp  Ser  Tyr  Glu  Ile  Tyr  Ile  Glu  Ala  Leu
               100                      105                      110

Arg  Glu  Trp  Glu  Ala  Asn  Pro  Asn  Asn  Ala  Gln  Leu  Arg  Glu  Asp  Val
          115                      120                      125

Arg  Ile  Arg  Phe  Ala  Asn  Thr  Asp  Asp  Ala  Leu  Ile  Thr  Ala  Ile  Asn
     130                      135                      140

Asn  Phe  Thr  Leu  Thr  Ser  Phe  Glu  Ile  Pro  Leu  Leu  Ser  Val  Tyr  Val
145                      150                      155                      160

Gln  Ala  Ala  Asn  Leu  His  Leu  Ser  Leu  Leu  Arg  Asp  Ala  Val  Ser  Phe
                    165                      170                      175

Gly  Gln  Gly  Trp  Gly  Leu  Asp  Ile  Ala  Thr  Val  Asn  Asn  His  Tyr  Asn
               180                      185                      190

Arg  Leu  Ile  Asn  Leu  Ile  His  Arg  Tyr  Thr  Lys  His  Cys  Leu  Asp  Thr
          195                      200                      205

Tyr  Asn  Gln  Gly  Leu  Glu  Asn  Leu  Arg  Gly  Thr  Asn  Thr  Arg  Gln  Trp
     210                      215                      220

Ala  Arg  Phe  Asn  Gln  Phe  Arg  Arg  Asp  Leu  Thr  Leu  Thr  Val  Leu  Asp
225                      230                      235                      240

Ile  Val  Ala  Leu  Phe  Pro  Asn  Tyr  Asp  Val  Arg  Thr  Tyr  Pro  Ile  Gln
                    245                      250                      255

Thr  Ser  Ser  Gln  Leu  Thr  Arg  Glu  Ile  Tyr  Thr  Ser  Ser  Val  Ile  Glu
               260                      265                      270

Asp  Ser  Pro  Val  Ser  Ala  Asn  Ile  Pro  Asn  Gly  Phe  Asn  Arg  Ala  Glu
          275                      280                      285

Phe  Gly  Val  Arg  Pro  Pro  His  Leu  Met  Asp  Phe  Met  Asn  Ser  Leu  Phe
     290                      295                      300

Val  Thr  Ala  Glu  Thr  Val  Arg  Ser  Gln  Thr  Val  Trp  Gly  Gly  His  Leu
305                      310                      315                      320

Val  Ser  Ser  Arg  Asn  Thr  Ala  Gly  Asn  Arg  Ile  Asn  Phe  Pro  Ser  Tyr
                    325                      330                      335

Gly  Val  Phe  Asn  Pro  Gly  Gly  Ala  Ile  Trp  Ile  Ala  Asp  Glu  Asp  Pro
               340                      345                      350

Arg  Pro  Phe  Tyr  Arg  Thr  Leu  Ser  Asp  Pro  Val  Phe  Val  Arg  Gly  Gly
          355                      360                      365

Phe  Gly  Asn  Pro  His  Tyr  Val  Leu  Gly  Leu  Arg  Gly  Val  Ala  Phe  Gln
     370                      375                      380

Gln  Thr  Gly  Thr  Asn  His  Thr  Arg  Thr  Phe  Arg  Asn  Ser  Gly  Thr  Ile
385                      390                      395                      400

Asp  Ser  Leu  Asp  Glu  Ile  Pro  Pro  Gln  Asp  Asn  Ser  Gly  Ala  Pro  Trp
                    405                      410                      415

Asn  Asp  Tyr  Ser  His  Val  Leu  Asn  His  Val  Thr  Phe  Val  Arg  Trp  Pro
               420                      425                      430

Gly  Glu  Ile  Ser  Gly  Ser  Asp  Ser  Trp  Arg  Ala  Pro  Met  Phe  Ser  Trp
          435                      440                      445

Thr  His  Arg  Ser  Ala  Thr  Pro  Thr  Asn  Thr  Ile  Asp  Pro  Glu  Arg  Ile
     450                      455                      460

Thr  Gln  Ile  Pro  Leu  Val  Lys  Ala  His  Thr  Leu  Gln  Ser  Gly  Thr  Thr
465                      470                      475                      480

Val  Val  Arg  Gly  Pro  Gly  Phe  Thr  Gly  Gly  Asp  Ile  Leu  Arg  Arg  Thr
                    485                      490                      495

Ser  Gly  Gly  Pro  Phe  Ala  Tyr  Thr  Ile  Val  Asn  Ile  Asn  Gly  Gln  Leu
               500                      505                      510

Pro  Gln  Arg  Tyr  Arg  Ala  Arg  Ile  Arg  Tyr  Ala  Ser  Thr  Thr  Asn  Leu
```

-continued

|  |  | 515 |  |  |  | 520 |  |  |  | 525 |  |  |
|---|---|---|---|---|---|---|---|---|---|---|---|---|
| Arg | Ile 530 | Tyr | Val | Thr | Val 535 | Ala | Gly | Glu | Arg | Ile 540 | Ala | Gly | Gln | Phe |
| Asn 545 | Lys | Thr | Met | Asp | Thr 550 | Gly | Asp | Pro | Leu | Thr 555 | Phe | Gln | Ser | Phe | Ser 560 |
| Tyr | Ala | Thr | Ile | Asn 565 | Thr | Ala | Phe | Thr | Phe 570 | Pro | Met | Ser | Gln | Ser 575 | Ser |
| Phe | Thr | Val | Gly 580 | Ala | Asp | Thr | Phe | Ser 585 | Ser | Gly | Asn | Glu | Val 590 | Tyr | Ile |
| Asp | Arg | Phe 595 | Glu | Leu | Ile | Pro | Val 600 | Thr | Ala | Thr | Phe | Glu 605 | Ala | Glu | Tyr |
| Asp | Leu 610 | Glu | Arg | Ala | Gln | Lys 615 | Ala | Val | Asn | Glu | Leu 620 | Phe | Thr | Ser | Ser |
| Asn 625 | Gln | Ile | Gly | Leu | Lys 630 | Thr | Asp | Val | Thr | Asp 635 | Tyr | His | Ile | Asp | Arg 640 |
| Val | Ser | Asn | Leu | Val 645 | Glu | Cys | Leu | Ser | Asp 650 | Glu | Phe | Cys | Leu | Asp 655 | Glu |
| Lys | Lys | Glu | Leu 660 | Ser | Glu | Lys | Val | Lys 665 | His | Ala | Lys | Arg | Leu 670 | Ser | Asp |
| Glu | Arg | Asn 675 | Leu | Leu | Gln | Asp | Pro 680 | Asn | Phe | Arg | Gly | Ile 685 | Asn | Arg | Gln |
| Leu | Asp 690 | Arg | Gly | Trp | Arg | Gly 695 | Ser | Thr | Asp | Ile | Thr 700 | Ile | Gln | Gly | Gly |
| Asp 705 | Asp | Val | Phe | Lys | Glu 710 | Asn | Tyr | Val | Thr | Leu 715 | Leu | Gly | Thr | Phe | Asp 720 |
| Glu | Cys | Tyr | Pro | Thr 725 | Tyr | Leu | Tyr | Gln | Lys 730 | Ile | Asp | Glu | Ser | Lys 735 | Leu |
| Lys | Ala | Tyr | Thr 740 | Arg | Tyr | Gln | Leu | Arg 745 | Gly | Tyr | Ile | Glu | Asp 750 | Ser | Gln |
| Asp | Leu | Glu 755 | Ile | Tyr | Leu | Ile | Arg 760 | Tyr | Asn | Ala | Lys | His 765 | Glu | Thr | Val |
| Asn | Val 770 | Pro | Gly | Thr | Gly | Ser 775 | Leu | Trp | Pro | Leu | Ser 780 | Ala | Pro | Ser | Pro |
| Ile 785 | Gly | Lys | Cys | Ala | His 790 | His | Ser | His | His | Phe 795 | Ser | Leu | Asp | Ile | Asp 800 |
| Val | Gly | Cys | Thr | Asp 805 | Leu | Asn | Glu | Asp | Leu 810 | Gly | Val | Trp | Val | Ile 815 | Phe |
| Lys | Ile | Lys | Thr 820 | Gln | Asp | Gly | His | Ala 825 | Arg | Leu | Gly | Asn | Leu 830 | Glu | Phe |
| Leu | Glu | Glu 835 | Lys | Pro | Leu | Val | Gly 840 | Glu | Ala | Leu | Ala | Arg 845 | Val | Lys | Arg |
| Ala | Glu 850 | Lys | Lys | Trp | Arg | Asp 855 | Lys | Arg | Glu | Lys | Leu 860 | Glu | Trp | Glu | Thr |
| Asn 865 | Ile | Val | Tyr | Lys | Glu 870 | Ala | Lys | Glu | Ser | Val 875 | Asp | Ala | Leu | Phe | Val 880 |
| Asn | Ser | Gln | Tyr | Asp 885 | Arg | Leu | Gln | Ala | Asp 890 | Thr | Asn | Ile | Ala | Met 895 | Ile |
| His | Ala | Ala | Asp 900 | Lys | Arg | Val | His | Ser 905 | Ile | Arg | Glu | Ala | Tyr 910 | Leu | Pro |
| Glu | Leu | Ser 915 | Val | Ile | Pro | Gly | Val 920 | Asn | Ala | Ala | Ile | Phe 925 | Glu | Glu | Leu |
| Glu | Gly 930 | Arg | Ile | Phe | Thr | Ala 935 | Phe | Ser | Leu | Tyr | Asp 940 | Ala | Arg | Asn | Val |

```
Ile Lys Asn Gly Asp Phe Asn Asn Gly Leu Ser Cys Trp Asn Val Lys
945                 950                 955                 960

Gly His Val Asp Val Glu Glu Gln Asn Asn His Arg Ser Val Leu Val
                965                 970                 975

Val Pro Glu Trp Glu Ala Glu Val Ser Gln Glu Val Arg Val Cys Pro
            980                 985                 990

Gly Arg Gly Tyr Ile Leu Arg Val Thr Ala Tyr Lys Glu Gly Tyr Gly
        995                 1000                1005

Glu Gly Cys Val Thr Ile His Glu Ile Glu Asn Asn Thr Asp Glu Leu
    1010                1015                1020

Lys Phe Ser Asn Cys Val Glu Glu Val Tyr Pro Asn Asn Thr Val
1025                1030                1035                1040

Thr Cys Asn Asp Tyr Thr Ala Thr Gln Glu Glu Tyr Glu Gly Thr Tyr
                1045                1050                1055

Thr Ser Arg Asn Arg Gly Tyr Asp Gly Ala Tyr Glu Ser Asn Ser Ser
                1060                1065                1070

Val Pro Ala Asp Tyr Ala Ser Ala Tyr Glu Glu Lys Ala Tyr Thr Asp
            1075                1080                1085

Gly Arg Arg Asp Asn Pro Cys Glu Ser Asn Arg Gly Tyr Gly Asp Tyr
    1090                1095                1100

Thr Pro Leu Pro Ala Gly Tyr Val Thr Lys Glu Leu Glu Tyr Phe Pro
1105                1110                1115                1120

Glu Thr Asp Lys Val Trp Ile Glu Ile Gly Glu Thr Glu Gly Thr Phe
                1125                1130                1135

Ile Val Asp Ser Val Glu Leu Leu Leu Met Glu Glu
                1140                1145
```

( 2 ) INFORMATION FOR SEQ ID NO:36:

( i ) SEQUENCE CHARACTERISTICS:
        ( A ) LENGTH: 1175 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:36:

```
Met Glu Asn Asn Ile Gln Asn Gln Cys Val Pro Tyr Asn Cys Leu Asn
1               5                   10                  15

Asn Pro Glu Val Glu Ile Leu Asn Glu Glu Arg Ser Thr Gly Arg Leu
            20                  25                  30

Pro Leu Asp Ile Ser Leu Ser Leu Thr Arg Phe Leu Leu Ser Glu Phe
        35                  40                  45

Val Pro Gly Val Gly Val Ala Phe Gly Leu Phe Asp Leu Ile Trp Gly
    50                  55                  60

Phe Ile Thr Pro Ser Asp Trp Ser Leu Phe Leu Leu Gln Ile Glu Gln
65                  70                  75                  80

Leu Ile Glu Gln Arg Ile Glu Thr Leu Glu Arg Asn Arg Ala Ile Thr
                85                  90                  95

Thr Leu Arg Gly Leu Ala Asp Ser Tyr Glu Ile Tyr Ile Glu Ala Leu
            100                 105                 110

Arg Glu Trp Glu Ala Asn Pro Asn Asn Ala Gln Leu Arg Glu Asp Val
        115                 120                 125

Arg Ile Arg Phe Ala Asn Thr Asp Asp Ala Leu Ile Thr Ala Ile Asn
    130                 135                 140

Asn Phe Thr Leu Thr Ser Phe Glu Ile Pro Leu Leu Ser Val Tyr Val
```

-continued

```
            145                 150                 155                 160
Gln Ala Ala Asn Leu His Leu Ser Leu Leu Arg Asp Ala Val Ser Phe
                165                 170                 175
Gly Gln Gly Trp Gly Leu Asp Ile Ala Thr Val Asn Asn His Tyr Asn
            180                 185                 190
Arg Leu Ile Asn Leu Ile His Arg Tyr Thr Lys His Cys Leu Asp Thr
            195                 200                 205
Tyr Asn Gln Gly Leu Glu Asn Leu Arg Gly Thr Asn Thr Arg Gln Trp
    210                 215                 220
Ala Arg Phe Asn Gln Phe Arg Arg Asp Leu Thr Leu Thr Val Leu Asp
225                 230                 235                 240
Ile Val Ala Leu Phe Pro Asn Tyr Asp Val Arg Thr Tyr Pro Ile Gln
                245                 250                 255
Thr Ser Ser Gln Leu Thr Arg Glu Ile Tyr Thr Ser Ser Val Ile Glu
                260                 265                 270
Asp Ser Pro Val Ser Ala Asn Ile Pro Asn Gly Phe Asn Arg Ala Glu
            275                 280                 285
Phe Gly Val Arg Pro Pro His Leu Met Asp Phe Met Asn Ser Leu Phe
            290                 295                 300
Val Thr Ala Glu Thr Val Arg Ser Gln Thr Val Trp Gly Gly His Leu
305                 310                 315                 320
Val Ser Ser Arg Asn Thr Ala Gly Asn Arg Ile Asn Phe Pro Ser Tyr
                325                 330                 335
Gly Val Phe Asn Pro Gly Gly Ala Ile Trp Ile Ala Asp Glu Asp Pro
            340                 345                 350
Arg Pro Phe Tyr Arg Thr Leu Ser Asp Pro Val Phe Val Arg Gly Gly
            355                 360                 365
Phe Gly Asn Pro His Tyr Val Leu Gly Leu Arg Gly Val Ala Phe Gln
    370                 375                 380
Gln Thr Gly Thr Asn His Thr Arg Thr Phe Arg Asn Ser Gly Thr Ile
385                 390                 395                 400
Asp Ser Leu Asp Glu Ile Pro Pro Gln Asp Asn Ser Gly Ala Pro Trp
                405                 410                 415
Asn Asp Tyr Ser His Val Leu Asn His Val Thr Phe Val Arg Trp Pro
            420                 425                 430
Gly Glu Ile Ser Gly Ser Asp Ser Trp Arg Ala Pro Met Phe Ser Trp
            435                 440                 445
Thr His Arg Ser Ala Thr Pro Thr Asn Thr Ile Asp Pro Glu Arg Ile
    450                 455                 460
Thr Gln Ile Pro Leu Val Lys Ala His Thr Leu Gln Ser Gly Thr Thr
465                 470                 475                 480
Val Val Arg Gly Pro Gly Phe Thr Gly Gly Asp Ile Leu Arg Arg Thr
                485                 490                 495
Ser Gly Gly Pro Phe Ala Tyr Thr Ile Val Asn Ile Asn Gly Gln Leu
            500                 505                 510
Pro Gln Arg Tyr Arg Ala Arg Ile Arg Tyr Ala Ser Thr Thr Asn Leu
            515                 520                 525
Arg Ile Tyr Val Thr Val Ala Gly Glu Arg Ile Phe Ala Gly Gln Phe
    530                 535                 540
Asn Lys Thr Met Asp Thr Gly Asp Pro Leu Thr Phe Gln Ser Phe Ser
545                 550                 555                 560
Tyr Ala Thr Ile Asn Thr Ala Phe Thr Phe Pro Met Ser Gln Ser Ser
                565                 570                 575
```

| Phe | Thr | Val | Gly | Ala | Asp | Thr | Phe | Ser | Ser | Gly | Asn | Glu | Val | Tyr | Ile |
|---|---|---|---|---|---|---|---|---|---|---|---|---|---|---|---|
| | | | 580 | | | | | 585 | | | | | | 590 | |

Asp Arg Phe Glu Leu Ile Pro Val Thr Ala Thr Leu Glu Ala Glu Tyr
595                    600                 605

Asn Leu Glu Arg Ala Gln Ala Val Asn Ala Leu Phe Thr Ser Pro
610                    615                 620

Asn Gln Leu Gly Ile Lys Thr Asn Val Thr Asp Tyr His Ile Asp Gln
625                    630                 635                 640

Val Ser Asn Leu Val Thr Cys Leu Ser Asp Glu Phe Cys Leu Asp Glu
                       645                 650                 655

Lys Arg Glu Leu Ser Glu Lys Val Lys His Ala Asn Gly Leu Ser Asp
                       660                 665                 670

Glu Arg Asn Leu Leu Gln Asp Ser Asn Phe Lys Asp Ile Asn Arg Gln
                       675                 680                 685

Pro Asp Arg Gly Trp Gly Gly Ser Thr Gly Ile Thr Ile Gln Arg Gly
                       690                 695                 700

Asp Asp Val Phe Lys Glu Asn Tyr Val Thr Leu Pro Gly Thr Phe Asp
705                    710                 715                 720

Glu Cys Tyr Leu Thr Tyr Leu Tyr Gln Lys Ile Asp Glu Ser Lys Leu
                       725                 730                 735

Lys Pro Tyr Thr Arg Tyr Glu Leu Arg Gly Tyr Ile Glu Asp Ser Gln
                       740                 745                 750

Asp Leu Glu Ile Tyr Leu Ile Arg Tyr Asn Ala Lys His Glu Thr Val
                       755                 760                 765

Asn Val Leu Gly Thr Gly Ser Leu Trp Arg Leu Ser Phe Glu Ser Ser
                       770                 775                 780

Ile Arg Lys Cys Gly Glu Pro Asn Arg Cys Ala Pro His Leu Glu Trp
785                    790                 795                 800

Asn Pro Asp Leu Asp Cys Ser Cys Arg Asp Gly Glu Lys Cys Ala His
                       805                 810                 815

His Ser His His Phe Ser Leu Asp Ile Asp Val Gly Cys Ile Asp Leu
                       820                 825                 830

Asn Glu Asp Leu Asp Val Trp Val Ile Phe Lys Ile Lys Thr Gln Asp
                       835                 840                 845

Gly His Glu Arg Leu Gly Ile Leu Glu Phe Leu Glu Gly Arg Ala Pro
                       850                 855                 860

Leu Val Gly Glu Ala Leu Ala Arg Val Lys Arg Ala Glu Lys Lys Trp
865                    870                 875                 880

Arg Asp Lys Arg Glu Lys Leu Gln Leu Glu Thr Asn Ile Val Tyr Lys
                       885                 890                 895

Glu Ala Lys Glu Ser Val Asp Ala Leu Phe Val Asn Ser Gln Tyr Asp
                       900                 905                 910

Gln Leu Gln Ala Asp Thr Asn Ile Ala Met Ile His Thr Ala Asp Lys
                       915                 920                 925

Arg Val His Arg Ile Gln Glu Ala Tyr Leu Pro Glu Leu Ser Val Ile
                       930                 935                 940

Pro Gly Val Asn Val Gly Ile Phe Glu Glu Leu Lys Gly Arg Ile Phe
945                    950                 955                 960

Thr Ala Phe Phe Leu Tyr Asp Ala Arg Asn Val Ile Lys Asn Gly Asp
                       965                 970                 975

Phe Asn Asn Gly Leu Ser Cys Trp Asn Val Lys Gly His Val Asp Val
                       980                 985                 990

Glu Glu Gln Asn Asn Gln Arg Ser Val Leu Val Val Pro Glu Trp Glu
                       995                 1000                1005

Ala Glu Val Ser Gln Glu Val Arg Val Cys Pro Gly Arg Gly Tyr Ile
        1010                1015                1020

Leu Arg Val Thr Ala Tyr Lys Glu Gly Tyr Gly Thr Gly Cys Val Thr
1025                1030                1035                1040

Ile His Glu Ile Glu Asn Asn Thr Asp Glu Leu Lys Phe Ser Asn Phe
                1045                1050                1055

Val Glu Glu Glu Val Tyr Pro Asn Asn Thr Val Thr Cys Asn Asp Tyr
            1060                1065                1070

Thr Ala Asn Gln Glu Glu Tyr Gly Gly Ala Tyr Thr Ser Cys Asn Arg
        1075                1080                1085

Gly Tyr Asp Glu Thr Tyr Gly Ser Asn Tyr Ser Val Pro Ala Asp Tyr
        1090                1095                1100

Ala Ser Val Tyr Glu Glu Lys Ala Tyr Thr Asp Gly Arg Arg Asp Asn
1105                1110                1115                1120

Pro Cys Glu Ser Asn Arg Gly Tyr Gly Asp Tyr Thr Pro Leu Pro Ala
                1125                1130                1135

Gly Tyr Val Thr Lys Gln Leu Glu Tyr Phe Pro Glu Thr Asp Lys Val
                1140                1145                1150

Trp Ile Glu Ile Gly Glu Thr Glu Gly Thr Phe Ile Val Asp Ser Val
                1155                1160                1165

Glu Leu Leu Leu Met Glu Glu
        1170            1175

( 2 ) INFORMATION FOR SEQ ID NO:37:

( i ) SEQUENCE CHARACTERISTICS:
        ( A ) LENGTH: 1148 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:37:

Met Glu Asn Asn Ile Gln Asn Gln Cys Val Pro Tyr Asn Cys Leu Asn
1               5                   10                  15

Asn Pro Glu Val Glu Ile Leu Asn Glu Glu Arg Ser Thr Gly Arg Leu
            20                  25                  30

Pro Leu Asp Ile Ser Leu Ser Leu Thr Arg Phe Leu Leu Ser Glu Phe
        35                  40                  45

Val Pro Gly Val Gly Val Ala Phe Gly Leu Phe Asp Leu Ile Trp Gly
    50                  55                  60

Phe Ile Thr Pro Ser Asp Trp Ser Leu Phe Leu Leu Gln Ile Glu Gln
65                  70                  75                  80

Leu Ile Glu Gln Arg Ile Glu Thr Leu Glu Arg Asn Arg Ala Ile Thr
                85                  90                  95

Thr Leu Arg Gly Leu Ala Asp Ser Tyr Glu Ile Tyr Ile Glu Ala Leu
            100                 105                 110

Arg Glu Trp Glu Ala Asn Pro Asn Asn Ala Gln Leu Arg Glu Asp Val
            115                 120                 125

Arg Ile Arg Phe Ala Asn Thr Asp Asp Ala Leu Ile Thr Ala Ile Asn
        130                 135                 140

Asn Phe Thr Leu Thr Ser Phe Glu Ile Pro Leu Leu Ser Val Tyr Val
145                 150                 155                 160

Gln Ala Ala Asn Leu His Leu Ser Leu Leu Arg Asp Ala Val Ser Phe
                165                 170                 175

```
Gly Gln Gly Trp Gly Leu Asp Ile Ala Thr Val Asn Asn His Tyr Asn
            180                 185                 190

Arg Leu Ile Asn Leu Ile His Arg Tyr Thr Lys His Cys Leu Asp Thr
        195                 200                 205

Tyr Asn Gln Gly Leu Glu Asn Leu Arg Gly Thr Thr Arg Gln Trp
    210                 215                 220

Ala Arg Phe Asn Gln Phe Arg Arg Asp Leu Thr Leu Thr Val Leu Asp
225                 230                 235                 240

Ile Val Ala Leu Phe Pro Asn Tyr Asp Val Arg Thr Tyr Pro Ile Gln
                245                 250                 255

Thr Ser Ser Gln Leu Thr Arg Glu Ile Tyr Thr Ser Ser Val Ile Glu
                260                 265                 270

Asp Ser Pro Val Ser Ala Asn Ile Pro Asn Gly Phe Asn Arg Ala Glu
        275                 280                 285

Phe Gly Val Arg Pro Pro His Leu Met Asp Phe Met Asn Ser Leu Phe
    290                 295                 300

Val Thr Ala Glu Thr Val Arg Ser Gln Thr Val Trp Gly Gly His Leu
305                 310                 315                 320

Val Ser Ser Arg Asn Thr Ala Gly Asn Arg Ile Asn Phe Pro Ser Tyr
                325                 330                 335

Gly Val Phe Asn Pro Gly Gly Ala Ile Trp Ile Ala Asp Glu Asp Pro
                340                 345                 350

Arg Pro Phe Tyr Arg Thr Leu Ser Asp Pro Val Phe Val Arg Gly Gly
            355                 360                 365

Phe Gly Asn Pro His Tyr Val Leu Gly Leu Arg Gly Val Ala Phe Gln
    370                 375                 380

Gln Thr Gly Thr Asn His Thr Arg Thr Phe Arg Asn Ser Gly Thr Ile
385                 390                 395                 400

Asp Ser Leu Asp Glu Ile Pro Pro Gln Asp Asn Ser Gly Ala Pro Trp
                405                 410                 415

Asn Asp Tyr Ser His Val Leu Asn His Val Thr Phe Val Arg Trp Pro
            420                 425                 430

Gly Glu Ile Ser Gly Ser Asp Ser Trp Arg Ala Pro Met Phe Ser Trp
            435                 440                 445

Thr His Arg Ser Ala Thr Pro Thr Asn Thr Ile Asp Pro Glu Arg Ile
450                 455                 460

Thr Gln Ile Pro Leu Val Lys Ala His Thr Leu Gln Ser Gly Thr Thr
465                 470                 475                 480

Val Val Arg Gly Pro Gly Phe Thr Gly Gly Asp Ile Leu Arg Arg Thr
                485                 490                 495

Ser Gly Gly Pro Phe Ala Tyr Thr Ile Val Asn Ile Asn Gly Gln Leu
            500                 505                 510

Pro Gln Arg Tyr Arg Ala Arg Ile Arg Tyr Ala Ser Thr Thr Asn Leu
        515                 520                 525

Arg Ile Tyr Val Thr Val Ala Gly Glu Arg Ile Phe Ala Gly Gln Phe
    530                 535                 540

Asn Lys Thr Met Asp Thr Gly Asp Pro Leu Thr Phe Gln Ser Phe Ser
545                 550                 555                 560

Tyr Ala Thr Ile Asn Thr Ala Phe Thr Phe Pro Met Ser Gln Ser Ser
                565                 570                 575

Phe Thr Val Gly Ala Asp Thr Phe Ser Ser Gly Asn Glu Val Tyr Ile
            580                 585                 590

Asp Arg Phe Glu Leu Ile Pro Val Thr Ala Thr Phe Glu Ala Glu Tyr
            595                 600                 605
```

```
Asp  Leu  Glu  Arg  Ala  Gln  Lys  Ala  Val  Asn  Glu  Leu  Phe  Thr  Ser  Ile
     610                     615                    620
Asn  Gln  Ile  Gly  Leu  Lys  Thr  Asp  Val  Thr  Asp  Tyr  His  Ile  Asp  Arg
625                      630                    635                         640
Val  Ser  Asn  Leu  Val  Glu  Cys  Leu  Ser  Asp  Glu  Phe  Cys  Leu  Asp  Glu
                    645                    650                         655
Lys  Glu  Glu  Leu  Ser  Glu  Lys  Val  Lys  His  Ala  Lys  Arg  Leu  Ser  Asp
                    660                    665                    670
Glu  Arg  Asn  Leu  Leu  Gln  Asp  Pro  Asn  Phe  Arg  Gly  Ile  Asn  Arg  Gln
          675                    680                    685
Leu  Asp  Arg  Gly  Trp  Arg  Gly  Ser  Thr  Asp  Ile  Thr  Ile  Gln  Gly  Gly
     690                     695                    700
Asp  Asp  Val  Phe  Lys  Glu  Asn  Tyr  Val  Thr  Leu  Ser  Gly  Thr  Phe  Asp
705                      710                    715                         720
Glu  Cys  Tyr  Pro  Thr  Tyr  Leu  Tyr  Gln  Lys  Ile  Asp  Glu  Ser  Lys  Leu
                    725                    730                         735
Lys  Ala  Tyr  Thr  Arg  Tyr  Gln  Leu  Arg  Gly  Tyr  Ile  Glu  Asp  Ser  Gln
                    740                    745                    750
Asp  Leu  Glu  Ile  Tyr  Leu  Ile  Arg  Tyr  Asn  Ala  Lys  His  Glu  Thr  Val
               755                    760                    765
Asn  Val  Pro  Gly  Thr  Gly  Ser  Leu  Trp  Pro  Leu  Ser  Val  Gln  Ser  Pro
     770                     775                    780
Ile  Gly  Lys  Cys  Ala  His  His  Ser  His  His  Phe  Ser  Leu  Asp  Ile  Asp
785                      790                    795                         800
Val  Gly  Cys  Thr  Asp  Leu  Asn  Glu  Asp  Leu  Gly  Val  Trp  Val  Ile  Phe
                    805                    810                         815
Lys  Ile  Lys  Thr  Gln  Asp  Gly  His  Ala  Arg  Leu  Gly  Asn  Leu  Glu  Phe
                    820                    825                    830
Leu  Glu  Glu  Lys  Pro  Leu  Val  Gly  Glu  Ala  Leu  Ala  Arg  Val  Lys  Arg
               835                    840                    845
Ala  Glu  Lys  Lys  Trp  Arg  Asp  Lys  Arg  Glu  Lys  Leu  Glu  Trp  Glu  Thr
     850                     855                    860
Asn  Ile  Val  Tyr  Lys  Glu  Ala  Lys  Glu  Ser  Val  Asp  Ala  Leu  Phe  Val
865                      870                    875                         880
Asn  Ser  Gln  Tyr  Asp  Arg  Leu  Gln  Ala  Asp  Thr  Asn  Ile  Ala  Met  Ile
                    885                    890                         895
His  Ala  Ala  Asp  Lys  Arg  Val  His  Ser  Ile  Arg  Glu  Ala  Tyr  Leu  Pro
                    900                    905                    910
Glu  Leu  Ser  Val  Ile  Pro  Gly  Val  Asn  Ala  Asp  Ile  Phe  Glu  Glu  Leu
               915                    920                    925
Glu  Gly  Arg  Ile  Phe  Thr  Ala  Phe  Ser  Leu  Tyr  Asp  Ala  Arg  Asn  Val
     930                     935                    940
Ile  Lys  Asn  Gly  Asp  Phe  Asn  Asn  Gly  Leu  Ser  Cys  Trp  Asn  Val  Lys
945                      950                    955                         960
Gly  His  Val  Asp  Val  Glu  Glu  Gln  Asn  Asn  His  Arg  Ser  Val  Leu  Val
                    965                    970                         975
Val  Pro  Glu  Trp  Glu  Ala  Glu  Val  Ser  Gln  Glu  Val  Arg  Val  Cys  Pro
                    980                    985                    990
Gly  Arg  Gly  Tyr  Ile  Leu  Arg  Val  Thr  Ala  Tyr  Lys  Glu  Gly  Tyr  Gly
          995                    1000                   1005
Glu  Gly  Cys  Val  Thr  Ile  His  Glu  Ile  Glu  Asn  Asn  Thr  Asp  Glu  Leu
     1010                    1015                   1020
Lys  Phe  Ser  Asn  Cys  Val  Glu  Glu  Glu  Val  Tyr  Pro  Asn  Asn  Thr  Val
```

-continued

```
        1025                    1030                    1035                    1040
    Thr Cys Asn Asp Tyr Thr Ala Thr Gln Glu Glu Tyr Glu Gly Thr Tyr
                    1045                    1050                    1055
    Thr Ser Arg Asn Arg Gly Tyr Asp Gly Ala Tyr Glu Ser Asn Ser Ser
                    1060                    1065                    1070
    Val Pro Ala Asp Tyr Ala Ser Ala Tyr Glu Glu Lys Ala Tyr Thr Asp
                    1075                    1080                    1085
    Gly Arg Arg Asp Asn Pro Cys Glu Ser Asn Arg Gly Tyr Gly Asp Tyr
                    1090                    1095                    1100
    Thr Pro Leu Pro Ala Gly Tyr Val Thr Lys Glu Leu Glu Tyr Phe Pro
    1105                    1110                    1115                    1120
    Glu Thr Asp Lys Val Trp Ile Glu Ile Gly Glu Thr Glu Gly Thr Phe
                    1125                    1130                    1135
    Ile Val Asp Ser Val Glu Leu Leu Leu Met Glu Glu
                    1140                    1145
```

( 2 ) INFORMATION FOR SEQ ID NO:38:

( i ) SEQUENCE CHARACTERISTICS:
      ( A ) LENGTH: 1148 amino acids
      ( B ) TYPE: amino acid
      ( C ) STRANDEDNESS: single
      ( D ) TOPOLOGY: linear ( i i ) MOLECULE TYPE: protein ( x i ) SEQUENCE DESCRIPTION: SEQ ID NO:38:

```
    Met Glu Asn Asn Ile Gln Asn Gln Cys Val Pro Tyr Asn Cys Leu Asn
    1                   5                   10                  15
    Asn Pro Glu Val Glu Ile Leu Asn Glu Glu Arg Ser Thr Gly Arg Leu
                    20                      25                      30
    Pro Leu Asp Ile Ser Leu Ser Leu Thr Arg Phe Leu Leu Ser Glu Phe
                    35                      40                      45
    Val Pro Gly Val Gly Val Ala Phe Gly Leu Phe Asp Leu Ile Trp Gly
                    50                      55                      60
    Phe Ile Thr Pro Ser Asp Trp Ser Leu Phe Leu Leu Gln Ile Glu Gln
    65                      70                      75                      80
    Leu Ile Glu Gln Arg Ile Glu Thr Leu Glu Arg Asn Arg Ala Ile Thr
                    85                      90                      95
    Thr Leu Arg Gly Leu Ala Asp Ser Tyr Glu Ile Tyr Ile Glu Ala Leu
                    100                     105                     110
    Arg Glu Trp Glu Ala Asn Pro Asn Asn Ala Gln Leu Arg Glu Asp Val
                    115                     120                     125
    Arg Ile Arg Phe Ala Asn Thr Asp Asp Ala Leu Ile Thr Ala Ile Asn
                    130                     135                     140
    Asn Phe Thr Leu Thr Ser Phe Glu Ile Pro Leu Leu Ser Val Tyr Val
    145                     150                     155                     160
    Gln Ala Ala Asn Leu His Leu Ser Leu Leu Arg Asp Ala Val Ser Phe
                    165                     170                     175
    Gly Gln Gly Trp Gly Leu Asp Ile Ala Thr Val Asn Asn His Tyr Asn
                    180                     185                     190
    Arg Leu Ile Asn Leu Ile His Arg Tyr Thr Lys His Cys Leu Asp Thr
                    195                     200                     205
    Tyr Asn Gln Gly Leu Glu Asn Leu Arg Gly Thr Asn Thr Arg Gln Trp
                    210                     215                     220
    Ala Arg Phe Asn Gln Phe Arg Arg Asp Leu Thr Leu Thr Val Leu Asp
    225                     230                     235                     240
```

-continued

| | | | | | | | | | | | | | | |
|---|---|---|---|---|---|---|---|---|---|---|---|---|---|---|
|Ile|Val|Ala|Leu|Phe 245|Pro|Asn|Tyr|Asp|Val 250|Arg|Thr|Tyr|Pro|Ile 255|Gln|
|Thr|Ser|Ser|Gln 260|Leu|Thr|Arg|Glu|Ile 265|Tyr|Thr|Ser|Ser|Val 270|Ile|Glu|
|Asp|Ser|Pro 275|Val|Ser|Ala|Asn|Ile 280|Pro|Asn|Gly|Phe|Asn 285|Arg|Ala|Glu|
|Phe|Gly 290|Val|Arg|Pro|Pro|His 295|Leu|Met|Asp|Phe|Met 300|Asn|Ser|Leu|Phe|
|Val 305|Thr|Ala|Glu|Thr|Val 310|Arg|Ser|Gln|Thr|Val 315|Trp|Gly|Gly|His|Leu 320|
|Val|Ser|Ser|Arg|Asn 325|Thr|Ala|Gly|Asn|Arg 330|Ile|Asn|Phe|Pro|Ser 335|Tyr|
|Gly|Val|Phe|Asn 340|Pro|Gly|Gly|Ala|Ile 345|Trp|Ile|Ala|Asp|Glu 350|Asp|Pro|
|Arg|Pro|Phe 355|Tyr|Arg|Thr|Leu|Ser 360|Asp|Pro|Val|Phe|Val 365|Arg|Gly|Gly|
|Phe|Gly 370|Asn|Pro|His|Tyr|Val 375|Leu|Gly|Leu|Arg|Gly 380|Val|Ala|Phe|Gln|
|Gln 385|Thr|Gly|Thr|Asn|His 390|Thr|Arg|Thr|Phe|Arg 395|Asn|Ser|Gly|Thr|Ile 400|
|Asp|Ser|Leu|Asp|Glu 405|Ile|Pro|Pro|Gln|Asp 410|Asn|Ser|Gly|Ala|Pro 415|Trp|
|Asn|Asp|Tyr|Ser 420|His|Val|Leu|Asn|His 425|Val|Thr|Phe|Val|Arg 430|Trp|Pro|
|Gly|Glu|Ile 435|Ser|Gly|Ser|Asp|Ser 440|Trp|Arg|Ala|Pro|Met 445|Phe|Ser|Trp|
|Thr|His 450|Arg|Ser|Ala|Thr|Pro 455|Thr|Asn|Thr|Ile|Asp 460|Pro|Glu|Arg|Ile|
|Thr 465|Gln|Ile|Pro|Leu|Val 470|Lys|Ala|His|Thr|Leu 475|Gln|Ser|Gly|Thr|Thr 480|
|Val|Val|Arg|Gly|Pro 485|Gly|Phe|Thr|Gly|Gly 490|Asp|Ile|Leu|Arg|Arg 495|Thr|
|Ser|Gly|Gly|Pro 500|Phe|Ala|Tyr|Thr|Ile 505|Val|Asn|Ile|Asn|Gly 510|Gln|Leu|
|Pro|Gln|Arg 515|Tyr|Arg|Ala|Arg|Ile 520|Arg|Tyr|Ala|Ser|Thr 525|Thr|Asn|Leu|
|Arg|Ile|Tyr 530|Val|Thr|Val|Ala 535|Gly|Glu|Arg|Ile|Phe 540|Ala|Gly|Gln|Phe|
|Asn|Lys|Thr|Met|Asp|Thr 550|Gly|Asp|Pro|Leu|Thr 555|Phe|Gln|Ser|Phe|Ser 560|
|545| | | | | | | | | | | | | | | |
|Tyr|Ala|Thr|Ile|Asn 565|Thr|Ala|Phe|Thr|Phe 570|Pro|Met|Ser|Gln|Ser 575|Ser|
|Phe|Thr|Val|Gly 580|Ala|Asp|Thr|Phe|Ser 585|Ser|Gly|Asn|Glu|Val 590|Tyr|Ile|
|Asp|Arg|Phe 595|Glu|Leu|Ile|Pro|Val 600|Thr|Ala|Thr|Phe|Glu 605|Ala|Glu|Tyr|
|Asp|Leu|Glu 610|Arg|Ala|Gln|Lys|Ala 615|Val|Asn|Glu|Leu|Phe 620|Thr|Ser|Thr|
|Asn 625|Gln|Ile|Gly|Leu|Lys 630|Thr|Asp|Val|Thr|Asp 635|Tyr|His|Ile|Asp|Arg 640|
|Val|Ser|Asn|Leu|Val 645|Glu|Cys|Leu|Ser|Asp 650|Glu|Phe|Cys|Leu|Asp 655|Glu|
|Lys|Glu|Glu|Leu|Ser|Glu|Lys|Val|Lys|His|Ala|Lys|Arg|Leu|Ser|Asp|

|   |   |   | 660 |   |   |   | 665 |   |   |   | 670 |   |   |   |
|---|---|---|---|---|---|---|---|---|---|---|---|---|---|---|

Glu Arg Asn Leu Leu Gln Asp Pro Asn Phe Arg Gly Ile Asn Arg Gln
        675                 680                 685

Leu Asp Arg Gly Trp Arg Gly Ser Thr Asp Ile Thr Ile Gln Gly Gly
        690                 695                 700

Asp Asp Val Phe Lys Glu Asn Tyr Val Thr Leu Ser Gly Thr Phe Asp
705                 710                 715                 720

Glu Cys Tyr Pro Thr Tyr Leu Tyr Gln Lys Ile Asp Glu Ser Lys Leu
                725                 730                 735

Lys Ala Tyr Thr Arg Tyr Gln Leu Arg Gly Tyr Ile Glu Asp Ser Gln
                740                 745                 750

Asp Leu Glu Ile Tyr Leu Ile Arg Tyr Asn Ala Lys His Glu Thr Val
            755                 760                 765

Asn Val Pro Gly Thr Gly Ser Leu Trp Pro Leu Ser Val Gln Ser Pro
        770                 775                 780

Ile Gly Lys Cys Ala His Ser His His Phe Ser Leu Asp Ile Asp
785                 790                 795                 800

Val Gly Cys Thr Asp Leu Asn Glu Asp Leu Gly Val Trp Val Ile Phe
                805                 810                 815

Lys Ile Lys Thr Gln Asp Gly His Ala Arg Leu Gly Asn Leu Glu Phe
                820                 825                 830

Leu Glu Glu Lys Pro Leu Val Gly Glu Ala Leu Ala Arg Val Lys Arg
            835                 840                 845

Ala Glu Lys Lys Trp Arg Asp Lys Arg Glu Lys Leu Glu Trp Glu Thr
        850                 855                 860

Asn Ile Val Tyr Lys Glu Ala Lys Glu Ser Val Asp Ala Leu Phe Val
865                 870                 875                 880

Asn Ser Gln Tyr Asp Arg Leu Gln Ala Asp Thr Asn Ile Ala Met Ile
                885                 890                 895

His Ala Ala Asp Lys Arg Val His Ser Ile Arg Glu Ala Tyr Leu Pro
                900                 905                 910

Glu Leu Ser Val Ile Pro Gly Val Asn Ala Asp Ile Phe Glu Glu Leu
            915                 920                 925

Glu Gly Arg Ile Phe Thr Ala Phe Ser Leu Tyr Asp Ala Arg Asn Val
        930                 935                 940

Ile Lys Asn Gly Asp Phe Asn Asn Gly Leu Ser Cys Trp Asn Val Lys
945                 950                 955                 960

Gly His Val Asp Val Glu Glu Gln Asn His Arg Ser Val Leu Val
                965                 970                 975

Val Pro Glu Trp Glu Ala Glu Val Ser Gln Glu Val Arg Val Cys Pro
            980                 985                 990

Gly Arg Gly Tyr Ile Leu Arg Val Thr Ala Tyr Lys Glu Gly Tyr Gly
        995                 1000                1005

Glu Gly Cys Val Thr Ile His Glu Ile Glu Asn Asn Thr Asp Glu Leu
        1010                1015                1020

Lys Phe Ser Asn Cys Val Glu Glu Val Tyr Pro Asn Asn Thr Val
1025                1030                1035                1040

Thr Cys Asn Asp Tyr Thr Ala Thr Gln Glu Glu Tyr Glu Gly Thr Tyr
                1045                1050                1055

Thr Ser Arg Asn Arg Gly Tyr Asp Gly Ala Tyr Glu Ser Asn Ser Ser
                1060                1065                1070

Val Pro Ala Asp Tyr Ala Ser Ala Tyr Glu Glu Lys Ala Tyr Thr Asp
        1075                1080                1085

| | | | | | | | | | | | | |
|---|---|---|---|---|---|---|---|---|---|---|---|---|
| Gly | Arg<br>1090 | Arg | Asp | Asn | Pro | Cys<br>1095 | Glu | Ser | Asn | Arg | Gly<br>1100 | Tyr | Gly | Asp | Tyr |
| Thr<br>1105 | Pro | Leu | Pro | Ala | Gly<br>1110 | Tyr | Val | Thr | Lys | Glu<br>1115 | Leu | Glu | Tyr | Phe | Pro<br>1120 |
| Glu | Thr | Asp | Lys | Val<br>1125 | Trp | Ile | Glu | Ile | Gly<br>1130 | Glu | Thr | Glu | Gly | Thr<br>1135 | Phe |
| Ile | Val | Asp | Ser<br>1140 | Val | Glu | Leu | Leu | Leu<br>1145 | Met | Glu | Glu |

We claim:

1. A method for improving *Bacillus thuringiensis* δ-endotoxin expression in a Pseudomonad comprising transforming said Pseudomonad with a gene encoding a *Bacillus thuringiensis* toxin wherein said *Bacillus thuringiensis* toxin is a chimeric toxin comprising a cryIF core N-terminal toxin portion and a C-terminal protoxin portion from a cryIA(b) toxin or a cryIA(c)/cryIA(b) chimeric toxin.

2. The method, according to claim 1, wherein said Pseudomonad is a *Pseudomonas fluorescens*.

3. The method, according to claim 1, wherein said Pseudomonad is transformed with a nucleotide sequence encoding a chimeric *Bacillus thuringiensis* toxin of approximately 1150 to 1200 amino acids, wherein said toxin comprises a cryIF core N-terminal sequence of at least about 590 amino acids and no more than about 1100 amino acids, and wherein said cryIA(b) or cryIA(c)/cryIA(b) protoxin portion comprises at least 100 amino acids at the C-terminus of said toxin.

4. The method, according to claim 3, wherein the transition from cryIF core N-terminal toxin portion to heterologous protoxin portion occurs after the sequence shown in SEQ ID NO. 30 and before the end of the peptide sequence of SEQ ID NO. 31.

5. The method, according to claim 4, wherein said core toxin portion comprises the first about 601 amino acids of a cryIF toxin and wherein said heterologous protoxin portion comprises the cryIA(b) or cryIA(c)/cryIA(b) amino acid sequence which follows the peptide sequence shown in SEQ ID NO. 31.

6. The method, according to claim 1, wherein said heterologous protoxin portion is that of a cryIA(b) toxin.

7. The method, according to claim 6, wherein said Pseudomonad is transformed with a polynucleotide comprising DNA which encodes the amino acid sequence of SEQ ID NO. 23.

8. The method, according to claim 7, wherein said DNA consists of the sequence of SEQ ID. NO. 22.

9. The method, according to claim 1, wherein said heterologous protoxin portion is that of a cryIA(c)/cryIA(b) chimeric toxin.

10. The method, according to claim 9, wherein said Pseudomonad is transformed with a polynucleotide comprising DNA which encodes the amino acid sequence of SEQ ID NO. 29.

11. The method, according to claim 10, wherein said DNA consists of the sequence of SEQ ID. NO. 28.

12. The method, according to claim 1, wherein said gene has been modified so as to utilize a higher percentage of codons which are favored by Pseudomonads.

13. The method, according to claim 12, wherein said Pseudomonad is transformed with a polynucleotide sequence comprising DNA which encodes the amino acid sequence of SEQ ID NO. 27.

14. The method, according to claim 13, wherein said DNA consists of the sequence of SEQ ID NO. 26.

15. The method according to claim 1, wherein said Pseudomonad is transformed with a gene which encodes an amino acid sequence selected from the group consisting of SEQ ID NO. 35, SEQ ID NO. 36, SEQ ID NO. 37, and SEQ ID NO. 38.

16. The method, according to claim 15, wherein said amino acid sequence is shown in SEQ ID NO. 35.

17. The method, according to claim 15, wherein said amino acid sequence is shown in SEQ ID NO. 36.

18. The method, according to claim 15, wherein said amino acid sequence is shown in SEQ ID NO. 37.

19. The method, according to claim 15, wherein said amino acid sequence is shown in SEQ ID NO. 38.

20. Treated, substantially intact cells containing an intracellular toxin, which toxin is a result of expression of a *Bacillus thuringiensis* gene encoding a toxin active against lepidopteran pests wherein said toxin is a chimeric toxin comprising a cryIF core N-terminal toxin portion and a protoxin portion from a cryIA(b) or a cryIA(c)/cryIA(b) chimeric toxin, wherein said cells are treated by chemical or physical means to prolong the insecticidal activity when said cells are applied to the environment of a target insect.

21. A process for controlling lepidopteran pests comprising contacting said pest with a lepidopteran-controlling effective amount of a substantially pure chimeric *Bacillus thuringiensis* toxin comprising a cryIF core N-terminal toxin portion and a C-terminal protoxin portion from a cryIA(b) toxin or cryIA(b)/cryIA(c) chimeric toxin.

* * * * *

UNITED STATES PATENT AND TRADEMARK OFFICE
CERTIFICATE OF CORRECTION

PATENT NO. : 5,840,554

DATED : November 24, 1998

INVENTOR(S) : Mark Thompson and George E. Schwab

It is certified that error appears in the above-identified patent and that said Letters Patent is hereby corrected as shown below:

Title page, item [54]

"β-ENDOTOXIN EXPRESSION IN *PSEUDOMONAS FLUORESCENS*"

should read

--DELTA-ENDOTOXIN EXPRESSION IN *PSEUDOMONAS FLUORESCENS*--

Column 1, lines 1-2, title:

"β-ENDOTOXIN EXPRESSION IN *PSEUDOMONAS FLUORESCENS*"

should read

--DELTA-ENDOTOXIN EXPRESSION IN *PSEUDOMONAS FLUORESCENS*--

Column 7, line 64: "Chambers el al." should read --Chambers *et al.*--; and line 67: "Geiser et al" should read --Geiser *et al.*--.

Column 10, line 54: "Agrobactenium" should read --Agrobacterium--; and line 60: "syningae" should read --syringae--.

Column 11, line 1: "*Ktuyveromyces*" should read --*Kluyveromyces*--.

Column 13, line 48: "560 mg" should read --500 mg--; and lines 53-54: should read --Add a few drops of 6 N $H_2SO_4$ to retard precipitation.--.

UNITED STATES PATENT AND TRADEMARK OFFICE
CERTIFICATE OF CORRECTION

PATENT NO. : 5,840,554

DATED : November 24, 1998

INVENTOR(S) : Mark Thompson and George E. Schwab

It is certified that error appears in the above-identified patent and that said Letters Patent is hereby corrected as shown below:

Column 16, line 67: "plasmnid" should read --plasmid--.

Column 19, line 49: "et al" should read --et al.--.

Signed and Sealed this

Thirteenth Day of April, 1999

Attest:

Q. TODD DICKINSON

Attesting Officer

Acting Commissioner of Patents and Trademarks